US008980875B2

(12) United States Patent
Mailliet et al.

(10) Patent No.: US 8,980,875 B2
(45) Date of Patent: *Mar. 17, 2015

(54) PLATINUM-N-HETEROCYCLIC CARBENE DERIVATIVES, PREPARATION THEREOF AND THERAPEUTIC USE THEREOF

(71) Applicants: Sanofi, Paris (FR); Centre National de la Recherche Scientifique, Paris cedex 16 (FR)

(72) Inventors: Patrick Mailliet, Fontenay sous Bois (FR); Angela Marinetti, Gif sur Yvette (FR); Myriem Skander, Gif sur Yvette (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/923,540

(22) Filed: Jun. 21, 2013

(65) Prior Publication Data

US 2013/0338128 A1    Dec. 19, 2013

Related U.S. Application Data

(60) Division of application No. 12/874,815, filed on Sep. 2, 2010, now Pat. No. 8,481,522, which is a continuation of application No. PCT/FR2009/000220, filed on Mar. 2, 2009.

(30) Foreign Application Priority Data

Mar. 3, 2008   (FR) ...................... 08 01155

(51) Int. Cl.
*A61K 31/555* (2006.01)
*C07F 15/00* (2006.01)

(52) U.S. Cl.
CPC ........... *C07F 15/0086* (2013.01); *A61K 31/555* (2013.01)
USPC ...................................................... 514/184

(58) Field of Classification Search
CPC ..................................................... A61K 31/555
USPC ......................................................... 514/184
See application file for complete search history.

(56) References Cited

U.S. PATENT DOCUMENTS 7,019,145 B2    3/2006 Buisine et al.
8,481,522 B2 *  7/2013 Mailliet et al. ................ 514/184

FOREIGN PATENT DOCUMENTS

WO   WO 02/098888   12/2002

OTHER PUBLICATIONS

PLATINOL-AQ (cisplatin injection) package insert. Revised Apr. 2006.*
Almeida et al., Detection of oxaliplatin-induced DNA crosslinks in vitro and in cancer patients using the alkaline comet assay, DNA Repair, 2006, vol. 5, pp. 219-225.
Antilla et al., Copper—Diamine-Catalyzed N-Arylation of Pyrroles, Pyrazoles, Indazoles, Imidazoles, and Triazoles, J. Organ. Chem., 2004, vol. 69, pp. 5578-5587.
Arduengo et al., A Stable Crystalline Carbene, J. Am. Chem Soc., 1991, vol. 113, pp. 361-363.
Barnard et al., Mitochondrial permeability transition induced by dinuclear gold(I)-carbene complexes: potential new antimitochondrial antitumour agents, Journal of Inorganic Biochemistry, 98, 2004, vol. 10, 1642-1647.
Benjes et al., Alkylation of 4(5)-Substituted Imidazoles, Heterocycles, 1994, vol. 37(2), 735-738.

(Continued)

*Primary Examiner* — Joseph Kosack
(74) *Attorney, Agent, or Firm* — Young & Thompson

(57) ABSTRACT

The invention relates to the platinum N-heterocycle derivatives of general formula (I)

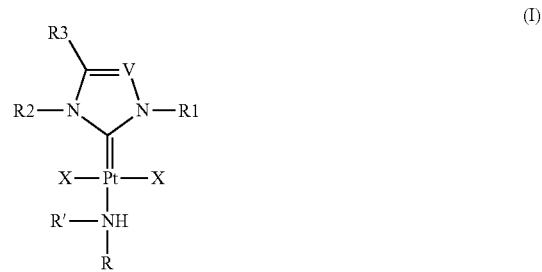

in which—$R_1$ and/or $R_2$ are, independently of one another, an aryl or aralkyl group, each optionally substituted, a linear or branched C1-C6 alkyl group, a monocyclic C3-C7 cycloalkyl group or a linear or branched C2-C6 alkenyl group, or else R' is a hydrogen atom and R is a group selected from the following groups: cycloalkyl or heterocycloalkyl, which is monocyclic or bicyclic and has from 3 to 8 carbon atoms, or benzyl, which is optionally substituted, or else R and R' form, together with NH, a C3-C8 monocyclic or bicyclic heterocycloalkyl, V is a nitrogen atom or a C—$R_4$ radical, $R_3$ and/or $R_4$ are hydrogen or a phenyl group or $R_3$ and $R_4$ may also together form a C3-C6 alkylene radical or a C3-C6 heteroalkylene radical with one or more nitrogenous heteroatoms, it being possible for the carbon atoms of the heteroalkylene radical to be modified in the form of a carbonyl radical, and X is iodine, bromine, chlorine or a nitrato (—$ONO_2$) group.

2 Claims, 3 Drawing Sheets

(56) References Cited

OTHER PUBLICATIONS

Berthon-Gelloz et al., Synthetic and structural studies of NHC-Pt(dvtms) complexes and their application as alkene hydrosilylation catalysts (NHC=N-heterocyclic carbene, dvtms=divinyltetramethylsiloxane), J. Organ. Chem., 2005, vol. 690, pp. 6156-6168.

Biffis et al., Highly Efficient Alkyne Hydroarylation with Chelating Dicarbene Palladium (II) and Platinum(II) Complexes, Adv. Synth. Catal., 2007, pp. 189-196, vol. 350, No. 1.

Brissy et al., N-Heterocyclic Carbenes in the Synthesis of Axially Chiral Square-Planar Platinum Complexes, Organometallics, 2007, vol. 26(24), 5782-5785.

Cavallo et al., Steric and electronic effects in the bonding of N-heterocyclic ligands to transition metals, J. Organ. Chem., 2005, vol. 690, pp. 5407-5413.

Collibee et al., The Unusual Cyclization of Benzil Monohydrazones to 4,5-Diphenylimidazoles Tetrahedron Letters, 1985, vol. 26, No. 13, pp. 1595-1596.

Fantasia et al., Electronic Properties of N-Heterocyclic Carbene (NHC) Ligands: Synthetic, Structural, and Spectroscopic Studies of (NHC) Platinum(II) Complexes, Organometallics, 2007, pp. 5880-5889, vol. 26, No. 24.

Foley et al., Continuous Culture of Human Lymphoblasts from Peripheral Blood of a Child with Acute Leukemia, Cancer, 1965, vol. 18, pp. 522-529.

Ghezzi et al., Uptake of antitumor platinum(II)-complexes by cancer cells, assayed by inductively coupled plasma mass spectrometry (ICP-MS), J. Inorg. Bio., 2004, pp. 73-78, vol. 98, No. 1.

Gleiter et al., on Stabilizing a Singlet Methylene, J. Am. Chem. Soc., 1968, vol. 90, pp. 5457-5460.

Grimmett et al., Hetarenes. Five-Membered Hetarenes with Two Nitrogen or Phosphorus Atoms, Imidazoles, Science of Synthesis, 2002, vol. 12, 325-528.

Grubbs et al., The development of L2X2Ru=CHR Olefin Metathesis Catalysts: An Organometallic Success story, Acc. Chem. Res., 2001, vol. 34, pp. 18-29.

Helleman et al., Mismatch repair and treatment resistance in ovarian cancer, BMC Cancer, 2006, vol. 6:201, pp. 1-10.

Herrmann et al., Metallkomplexe heterocyclisher Carbene—ein neues Katalysator-Strukturprinzip in der homogenen Katalyse, Angew. Chem., 1995, vol. 107, No. 21, pp. 2602-2605.

Herrmann et al.. N-Heterocyclic Carbenes: A New Concept in Organometallic Catalysis, Angew. Chem. Int. Ed., 2002, vol. 41, pp. 1290-1309.

Hu et al., Group 11 Metal Complexes of N-Heterocyclic Carbene Ligands: Nature of the Metal—Carbene Bond, Organometallics, 2004, vol. 23, pp. 755-764.

International Search Report for WO2009118475 dated Oct. 1, 2009.

Kascatan-Nebioglu et al., Synthesis from Caffeine of a Mixed N-Heterocyclic Carbene-Silver Acetate Complex Active against Resistant Respiratory Pathogens, J. Med. Chem., 2006, vol. 49, pp. 6811-6818.

Kelland et al., Mechanism-related Circumvention of Acquired cis-Diamminedichloroplatinum(II) Resistance Using Two Pairs of Human Ovarian Carcinoma Cell Lines by Ammine/Amine Platinum(IV) Dicarboxylates, Cancer Res., 1992, vol. 52, pp. 3857-3864.

Kilpelainen et al., Dissolution of Wood in Ionic Liquids, J. Agric. Food Chem. 2007, vol. 55, pp. 9142-9148.

Kovala-Demertzi et al., Platinum (II) and palladium(II) complexes with 2-Acetyl pyridine 4N-ethyl thiosemicarbazone able to overcome the cis-Platin resistance, BioMetals, 2003, pp. 411-418, vol. 16, No. 3.

Letaief et al., Nanohybrid materials from the intercalation of imidazolium ionic liquids in kaolinite, J. Mat. Chem., 2007, vol. 17(15), pp. 1476-1486.

Magill et al., Palladium (II) complexes containing mono-, bi- and tridentate carbene ligands. Synthesis, characterisation and application as catalysts in C—C coupling reactions, J. Organ. Chem., 2001, vol. 617-618, pp. 546-560.

Mamenta et al., Enhanced Replicative Bypass of Platinum-DNA Adducts in Cisplatin-resistant Human Ovarian Carcinoma Cell Lines, Cancer Res., 1994, vol. 54, pp. 3500-3505.

Marko et al., Highly Active and Selective Platinum (0)—Carbene Complexes. Efficient, Catalytic Hydrosilylation of Functionalised Olefins, Advance Synthesis and Catalysis, 2004, vol. 346(12), pp. 1429-1434.

Ofele et al., 1,3-Dimethyl-4-Imidazolinyliden-(2)-Pentacarbonylchrom. Ein Neuer Ubergangsmetall-Carben-Complex, J. Organomet Chem. 1968, vol. 12, p. 42.

O'Neill, et al, Cellular pharmacology of cis and trans pairs of platinum complexes in cisplatin-sensitive and—resistant human ovarian carcinoma cells, Chemico-Biological Interactions, 1999, vol. 123, pp. 11-29.

Perez et al., Antitumor and Cellular Pharmacological Properties of a Novel Platinum(IV) Complex: trans-[PtCl2 (OH)2(Dimethylamine)(Isopropylamine)], Molecular Pharmacology, 2003, vol. 63, pp. 933-944.

Ray et al., Anticancer and Antimicrobial Metallopharmaceutical Agents Based on Palladium, Gold, and Silver N-Heterocyclic Carbene Complexes, J. Am. Chem. Soc., 2007, pp. 15042-15053, vol. 129, No. 48.

Raynaud et al., Intracellular metabolism of the orally active platinum drug JM216: influence of glutathione levels, British Journal of Cancer, 1996, vol. 74, pp. 380-386.

Restriction Requirement as mailed from US Patent and Trademark Office in U.S. Appl. No. 12/874,815, filed Feb. 7, 2012.

Sharp et al., Lack of a role for MRP1 in platinum drug resistance in human ovarian cancer cell lines, British Journal of Cancer, 1998, vol. 78(2), pp. 175-180.

Wanzlick et al., Direct Synthesis of a Mercury Salt-Carbene Complex, Angew. Chem. Internat. Edit., 1968, vol. 7, No. 2, pp. 141.

Woynarowski et al., Oxaliplatin-Induced Damage of Cellular DNA, Molecular Pharmacology, 2000, vol. 58, pp. 920-927.

* cited by examiner

PLATINUM-N-HETEROCYCLIC CARBENE DERIVATIVES, PREPARATION THEREOF AND THERAPEUTIC USE THEREOF

The present invention relates to platinum derivatives bearing a heterocyclic carbene ligand, abbreviated to N-heterocyclic carbene-platinum or NHC-Pt derivatives, their preparation and their therapeutic application.

Some platinum derivatives are well known as anticancer agents. The anticancer properties of the first among them, cisplatin, were discovered in 1965. Cisplatin was approved by the FDA in 1978, and then followed the approvals given, still by the FDA, to carboplatin in 1989 and to oxaliplatin in 2002, and finally satraplatin and picoplatin are currently the subject of marketing authorization applications to the FDA. Platinum exists, in the majority of these derivatives, in its oxidation state II, it is always coordinated with two amine ligands and, depending on the case, with chloride ligands for cisplatin or with an organic dicarboxylic acid derivative such as 1,1-cyclobutanedicarboxylic acid (called "CBDCA") for carboplatin, or oxalic acid for oxaliplatin. Picoplatin is also a derivative of platinum II bearing two nitrogen-containing ligands, one of which is α-picoline. Satraplatin consists of a platinum IV bonded still to two nitrogen-containing ligands, to two chlorides and to two acetate groups.

These compounds may be represented by the following formulae

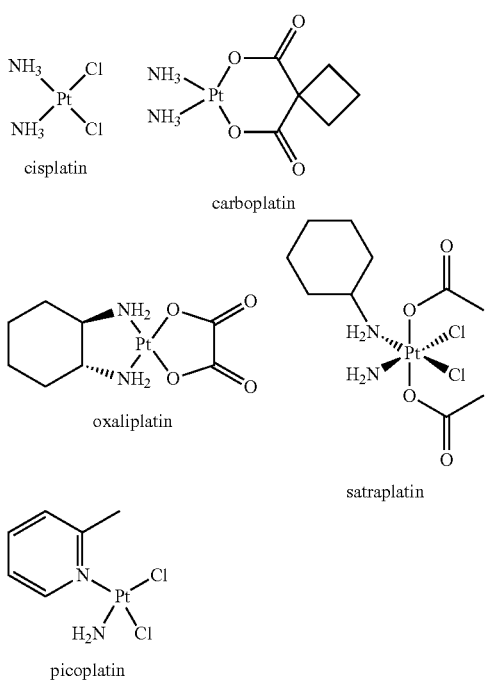

Among the various ligands recently developed in organometallic chemistry, carbenes rich in electrons and more specifically N-heterocyclic carbenes are very promising. The first NHC complexes were studied around the end of the 1960s by Öfele (*J. Organomet. Chem.* 1968, 12, P-42) and Wanzlick (*Angew. Chem. Int. Ed. Engl.* 1968, 7, 141), but it was only from 1991 that these compounds were developed on a major scale by virtue of the work by Arduengo which made it possible to isolate the first stable diaminocarbene (*J. Am. Chem. Soc.* 1991, 113, 361).

N-heterocyclic carbenes are neutral compounds possessing a divalent carbon with six valence electrons, which is located between two nitrogens. They are accessible, inter alia, from the corresponding imidazolium salts or olefins called "Wanzlick dimers". From an electron point of view, a carbene is composed of a σ orbital located in the plane of the ring and a $p_\pi$ orbital perpendicular thereto. In the case of diaminocarbenes, the presence of nitrogens in a promotes an electron spin singlet state where the two electrons are in the σ orbital (Gleiter, R. et al.; *J. Am. Chem. Soc.* 1968, 90, 5457).

NHCs form very stable complexes with transition metals. These are Fischer-type complexes in which the metal-NHC bond is characterized by a strong σ donation from the carbene to the metal and a weak π retrodonation (Hu, X. et al.; *Organometallics* 2004, 23, 755; L. Cavallo et al. *J. Organomet. Chem.* 2005, 690, 5407).

The first applications in organometallic catalysis involved Heck and Suzuki type C—C coupling reactions. For these reactions, the palladium-carbene complexes are extremely advantageous catalysts because of the high stability of the metal-NHC bond and because they are easy to prepare (Herrmann, W. A. et al.; *Angew. Chem.* 1995, 107, 2602). NHC complexes have very often proved more efficient in homogeneous catalysis than similar complexes bearing phosphines. The best known example relates to olefin metathesis reactions. Indeed, the work by Grubbs (*Acc. Chem. Res.* 2001, 34, 18) involving the replacement of phosphine ligands by NHCs has made it possible to obtain ruthenium catalysts, called "second generation Grubbs catalysts", which are highly efficient because of their high functional group tolerance and their mild reaction conditions. Numerous other applications exist in organometallic catalysis and there are currently a wide variety of metal-NHC complexes. Indeed, the easily modulable structure of N-heterocyclic carbenes makes it possible to quite easily introduce chiral groups, functional groups, to perform immobilizations on a support, to create chelating bidentate ligands, and the like (Herrmann, W. A.; *Angew. Chem. Int. Ed.* 2002, 41, 1290).

A few examples of application of carbenic complexes in the biomedical field exist in the literature. Silver(I) complexes containing a bis-carbene ligand, or a caffeine derivative (Youngs, W. J. et al.; *J. Med. Chem.* 2006, 49, 6811), have been synthesized in order to obtain compounds which possess antimicrobial and antifungal properties. The replacement of the metal, in these structures, by a radioactive element, such as a radioisotope of rhodium, silver, gallium or technetium, allows applications in medical imaging or for the treatment of cancer cells (Youngs, W. J. et al.; WO 2005023760 A2).

Moreover, bis-chelated carbenic complexes of gold(I) have been synthesized with the aim of studying their antitumour activity, by an antimitochondrial effect, in comparison with the $[Au(dppe)_2]^+$ complexes already mentioned (Barnard, P. J. et al.; *J. Inorg. Biochem.* 2004, 10, 1642).

Finally, an article by S. Ray, R. Mohan, J. K. Singh, M. K. Samantaray, M. M. Shaikh, D. Panda and P. Ghosh, in the Journal of the American Chemical Society, vol. 48, p. 15042 to 15053, which appeared on 5 Dec. 2007 under the title "Anticancer and Antimicrobial Metallopharmaceutical Agents Based on Palladium, Gold, and Silver N-Heterocyclic Carbene Complexes" describes, among the derivatives of metals bonded to an N-heterocyclic carbene, palladium, gold or silver complexes. In this article, are considered as active agents in oncology only palladium complexes and in particular the following derivatives:

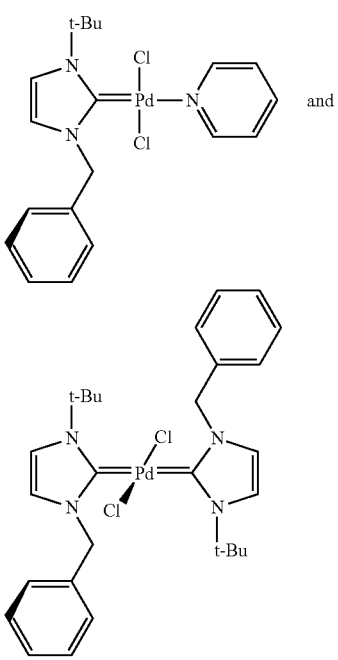

Figure 1:
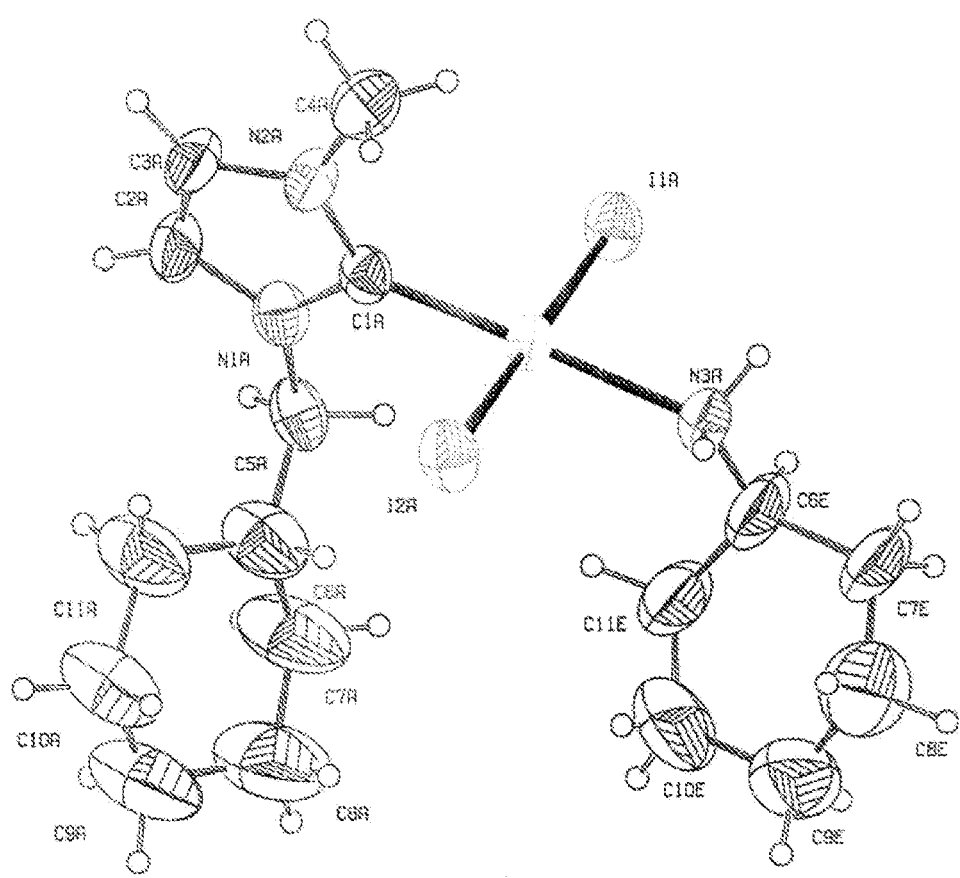
FIG. 1: Depicts an ORTEP diagram representing the structure of the compound of Example 3, described herein.

The subject of the present invention is N-heterocyclic carbene (NHC)-platinum complexes bearing in trans of the carbene a nitrogen-containing ligand and corresponding to the general formula (I)

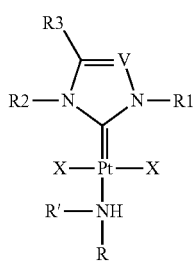

formula (I)

in which $R_1$ and/or $R_2$ represent independently of each other an aryl or aralkyl group, each optionally substituted, a linear or branched C1-C6 alkyl group, a monocyclic C3-C7 cycloalkyl group or a linear or branched C2-C6 alkenyl group or R' represents a hydrogen atom and R represents a group chosen from C3-C8 mono- or bicyclic cycloalkyl or heterocycloalkyl groups or an optionally substituted benzyl group or R and R' form together with NH a C3-C8 mono- or bicyclic heterocycloalkyl V represents a nitrogen atom or a C—$R_4$ radical $R_3$ and/or $R_4$ represent hydrogen, a phenyl group or $R_3$ and $R_4$ may also form together a C3-C6 alkylene or C3-C6 heteroalkylene radical with one or more nitrogen-based heteroatoms, it being possible for the carbon atoms of the heteroalkylene radical to be modified in the form of a carbonyl radical X represents iodine, bromine, chlorine or a nitrato (—$ONO_2$) group.

The compounds of formula (I) may also exist in the form of hydrates or solvates, namely in the form of associations or combinations with one or more water molecules or with a solvent. Such hydrates and solvates also form part of the invention.

In the context of the present invention:

an alkyl group is understood to mean a saturated linear or branched C1-C6 aliphatic group. By way of examples, there may be mentioned the methyl, ethyl, propyl, isopropyl, butyl, isobutyl, tert-butyl, pentyl and hexyl groups;

a cycloalkyl group is understood to mean a C3-C7 monocyclic or C4-C8 bicyclic alkyl group. By way of examples of C3-C7 monocyclic alkyl groups, there may be mentioned the cyclopropyl, cyclobutyl, cyclopentyl and cyclohexyl groups; by way of examples of C6-C8 bicyclic groups, there may be mentioned bicyclo[2.2.1]heptyl, bicyclo[2.2.2]octyl and bicyclo[3.2.1]octyl;

an alkenyl group is understood to mean a linear or branched mono- or polyunsaturated aliphatic group comprising for example one or two ethylenic unsaturations and containing 2 to 6 carbon atoms;

an alkylene group is understood to mean a saturated linear or branched aliphatic group having a free bond at each end;

a heteroalkylene group is understood to mean a linear or branched mono- or polyunsaturated C2-C3 aliphatic group with one or more nitrogen-based heteroatoms;

an aryl group is understood to mean a monocyclic aromatic group. By way of examples of aryl groups, phenyl groups may be mentioned. These groups are optionally substituted with a C1-C2 alkoxy group or with a C1-C2 perfluoroalkyl group;

an aralkyl group is understood to mean a monocyclic aromatic group linked by a C1-C2 alkylene unit.

Among the compounds of formula (I) which are the subject of the invention, a first group of compounds consists of the compounds for which:

R1 and/or R2 represent independently of each other a C1-C4 alkyl group, and/or V represents N or C—$R_4$ and/or R3 and/or R4 represent hydrogen or form together an alkenylene radical and/or R'=H and R represents a cyclohexyl or norbornyl or 4-aminotetrahydropyranyl unit and/or R and R' form with NH a morpholine and/or X is iodine.

Among the compounds of formula (I) which are the subject of the invention, a second group of compounds consists of the compounds for which:

R1 and/or R2 represent independently of each other a benzyl and/or an alkyl;

and/or V represents N or C—$R_4$ and/or R3 and/or R4 represent hydrogen or form together an alkenylene radical;

and/or R represents a cyclohexyl or norbornyl or 4-aminotetrahydropyranyl unit and R' is H and/or R and R' form with NH a morpholine and/or X is iodine.

Among the compounds of formula (I) which are the subject of the invention, a third group of compounds consists of the compounds for which:

R1 and/or R2 represent independently of each other a cyclohexylmethylene group and/or an alkyl group, and/or V represents N or C—R$_4$ and/or R3 and/or R4 represent hydrogen or form together an alkenylene radical and/or R'=H and R represents a cyclohexyl or norbornyl or 4-aminotetrahydropyranyl unit and/or R and R' form with NH a morpholine and/or X is iodine.

Among the compounds of group two, the benzyl group may be substituted by a CF$_3$ or methoxy unit.

Among the compounds of formula (I) which are the subject of the invention, the following compounds may be mentioned in particular:

trans-diiodo(N-cyclohexylamine)(1,3-dimethylimidazol-2-ylidene)platinum(II)

trans-dibromo(N-cyclohexylamine)(1,3-dimethylimidazol-2-ylidene)platinum(II)

trans-dichloro(N-cyclohexylamine)(1,3-dimethylimidazol-2-ylidene)platinum(II)

trans-dinitrato(N-cyclohexylamine)(1,3-dimethylimidazol-2-ylidene)platinum(II)

trans-diiodo(N-cyclohexylamine)(1,4-dimethyl-1,2,4-triazol-3-ylidene)platinum(II)

trans-dibromo(N-cyclohexylamine)(1,4-dimethyl-1,2,4-triazol-3-ylidene)platinum(II)

trans-dichloro(N-cyclohexylamine)(1,4-dimethyl-1,2,4-triazol-3-ylidene)platinum(II)

trans-dinitrato(N-cyclohexylamine)(1,4-dimethyl-1,2,4-triazol-3-ylidene)platinum(II)

trans-diiodo(N-cyclohexylamine)(1-methyl-3-(cyclohexylmethyl)imidazol-2-ylidene)platinum(II)

trans-dibromo(N-cyclohexylamine)(1-methyl-3-(cyclohexylmethyl)imidazol-2-ylidene)platinum(II)

trans-dichloro(N-cyclohexylamine)(1-methyl-3-(cyclohexylmethyl)imidazol-2-ylidene)platinum(II)

trans-dinitrato(N-cyclohexylamine)(1-methyl-3-(cyclohexylmethyl)imidazol-2-ylidene)platinum(II)

trans-diiodo(N-cyclohexylamine)(1-methyl-3-phenylimidazol-2-ylidene)platinum(II)

trans-dibromo(N-cyclohexylamine)(1-methyl-3-phenylimidazol-2-ylidene)-platinum(II)

trans-dichloro(N-cyclohexylamine)(1-methyl-3-phenylimidazol-2-ylidene)-platinum(II)

trans-dinitrato(N-cyclohexylamine)(1-methyl-3-phenylimidazol-2-ylidene)-platinum(II)

trans-diiodo(N-tetrahydropyranyl-4-amine)(1,3-dimethylimidazol-2-ylidene)-platinum(II)

trans-dibromo(N-tetrahydropyranyl-4-amine)(1,3-dimethylimidazol-2-ylidene)-platinum(II)

trans-dichloro(N-tetrahydropyranyl-4-amine)(1,3-dimethylimidazol-2-ylidene)-platinum(II)

trans-dinitrato(N-tetrahydropyranyl-4-amine)(1,3-di methylimidazol-2-ylidene)-platinum(II)

trans-diiodo(N-tetrahydropyranyl-4-amine)(1,4-di methyl-1,2,4-triazol-3-ylidene)platinum(II)

trans-dibromo(N-tetrahydropyranyl-4-amine)(1,4-dimethyl-1,2,4-triazol-3-ylidene)platinum(II)

trans-dichloro(N-tetrahydropyranyl-4-amine)(1,4-dimethyl-1,2,4-triazol-3-ylidene)platinum(II)

trans-dinitrato(N-tetrahydropyranyl-4-amine)(1,4-dimethyl-1,2,4-triazol-3-ylidene)platinum(II)

trans-diiodo(N-tetrahydropyranyl-4-amine)(1-methyl-3-(cyclohexylmethyl)imidazol-2-ylidene)platinum(II)

trans-dibromo(N-tetrahydropyranyl-4-amine)(1-methyl-3-(cyclohexylmethyl)imidazol-2-ylidene)platinum(II)

trans-dichloro(N-tetrahydropyranyl-4-amine)(1-methyl-3-(cyclohexylmethyl)imidazol-2-ylidene)platinum(II)

trans-dinitrato(N-tetrahydropyranyl-4-amine)(1-methyl-3-(cyclohexylmethyl)imidazol-2-ylidene)platinum(II)

trans-diiodo(N-tetrahydropyranyl-4-amine)(1-methyl-3-phenylimidazol-2-ylidene)platinum(II)

trans-dibromo(N-tetrahydropyranyl-4-amine)(1-methyl-3-phenylimidazol-2-ylidene)platinum(II)

trans-dichloro(N-tetrahydropyranyl-4-amine)(1-methyl-3-phenylimidazol-2-ylidene)platinum(II)

trans-dinitrato(N-tetrahydropyranyl-4-amine)(1-methyl-3-phenyl imidazol-2-ylidene)platinum(II)

trans-diiodo(N-morpholine)(1,3-dimethylimidazol-2-ylidene)platinum(II)

trans-dibromo(N-morpholine)(1,3-dimethylimidazol-2-ylidene)platinum(II)

trans-dichloro(N-morpholine)(1,3-dimethylimidazol-2-ylidene)platinum(II)

trans-dinitrato(N-morpholine)(1,3-dimethylimidazol-2-ylidene)platinum(II)

trans-diiodo(N-morpholine)(1,4-dimethyl-1,2,4-triazol-3-ylidene)platinum(II)

trans-dibromo(N-morpholine)(1,4-dimethyl-1,2,4-triazol-3-ylidene)platinum(II)

trans-dichloro(N-4-amino-tetrahydropyran)(1,4-dimethyl-1,2,4-triazol-3-ylidene)platinum(II)

trans-dinitrato(N-morpholine)(1,4-dimethyl-1,2,4-triazol-3-ylidene)platinum(II)

trans-diiodo(N-morpholine)(1-methyl-3-(cyclohexylmethyl) imidazol-2-ylidene)-platinum(II)

trans-dibromo(N-morpholine)(1-methyl-3-(cyclohexylmethyl)imidazol-2-ylidene)platinum(II)

trans-dichloro(N-morpholine)(1-methyl-3-(cyclohexylmethyl)imidazol-2-ylidene)platinum(II)

trans-dinitrato(N-morpholine)(1-methyl-3-(cyclohexylmethyl)imidazol-2-ylidene)platinum(II)

trans-diiodo(N-morpholine)(1-methyl-3-phenylimidazol-2-ylidene)platinum(II)

trans-dibromo(N-morpholine)(1-methyl-3-phenylimidazol-2-ylidene)platinum(II)

trans-dichloro(N-morpholine)(1-methyl-3-phenylimidazol-2-ylidene)platinum(II)

trans-dinitrato(N-morpholine)(1-methyl-3-phenylimidazol-2-ylidene)platinum(II)

trans-diiodo[N-(1-methylpiperidin-4-ylamine)](1,3-dimethylimidazol-2-ylidene)-platinum(II)

trans-dibromo[N-(1-methylpiperidin-4-ylamine)](1,3-dimethylimidazol-2-ylidene)platinum(II)

trans-dichloro[N-(1-methylpiperidin-4-ylamine)](1,3-dimethylimidazol-2-ylidene)platinum(II)

trans-dinitrato[N-(1-methylpiperidin-4-ylamine)]](1,3-dimethylimidazol-2-ylidene)platinum(II)

trans-diiodo[N-(1-methylpiperidin-4-ylamine)](1,4-dimethyl-1,2,4-triazol-3-ylidene)platinum(II)

trans-dibromo[N-(1-methylpiperidin-4-ylamine)](1,4-dimethyl-1,2,4-triazol-3-ylidene)platinum(II)

trans-dichloro[N-(1-methylpiperidin-4-ylamine)](1,4-dimethyl-1,2,4-triazol-3-ylidene)platinum(II)

trans-dinitrato[N-(1-methylpiperidin-4-ylamine)](1,4-dimethyl-1,2,4-triazol-3-ylidene)platinum(II)

trans-diiodo[N-(1-methylpiperidin-4-ylamine)](1-methyl-3-(cyclohexylmethyl)imidazol-2-ylidene)platinum(II)

trans-dibromo[N-(1-methylpiperidin-4-ylamine)](1-methyl-3-(cyclohexylmethyl)imidazol-2-ylidene)platinum(II)

trans-dichloro[N-(1-methylpiperidin-4-ylamine)](1-methyl-3-(cyclohexylmethyl)imidazol-2-ylidene)platinum(II)
trans-dinitrato[N-(1-methylpiperidin-4-ylamine)](1-methyl-3-(cyclohexylmethyl)imidazol-2-ylidene)platinum(II)
trans-diiodo[N-(1-methylpiperidin-4-ylamine)](1-methyl-3-phenylimidazol-2-ylidene)platinum(II)
trans-dibromo[N-(1-methylpiperidin-4-ylamine)](1-methyl-3-phenylimidazol-2-ylidene)platinum(II)
trans-dichloro[N-(1-methylpiperidin-4-ylamine)](1-methyl-3-phenylimidazol-2-ylidene)platinum(II)
trans-dinitrato[N-(1-methylpiperidin-4-ylamine)](1-methyl-3-phenylimidazol-2-ylidene)platinum(II)
trans-diiodo(N-exo(+/−)bicyclo[2.2.1]heptylamine)(1,3-dimethylimidazol-2-ylidene)platinum(II)
trans-dibromo(N-exo(+/−)bicyclo[2.2.1]heptylamine)(1,3-dimethylimidazol-2-ylidene)platinum(II)
trans-dichloro(N-exo(+/−)bicyclo[2.2.1]heptylamine)(1,3-dimethylimidazol-2-ylidene)platinum(II)
trans-dinitrato(N-exo(+/−)bicyclo[2.2.1]heptylamine)(1,3-dimethylimidazol-2-ylidene)platinum(II)
trans-diiodo(N-cyclohexylamine)(1,3-dimethylbenzimidazol-2-ylidene)platinum(II)
trans-dibromo(N-cyclohexylamine)(1,3-dimethylbenzimidazol-2-ylidene)platinum(II)
trans-dichloro(N-cyclohexylamine)(1,3-dimethylbenzimidazol-2-ylidene)platinum(II)
trans-dinitratochloro(N-cyclohexylamine)(1,3-dimethylbenzimidazol-2-ylidene)-platinum(II)
trans-diiodo(N-cyclohexylamine)(1,3,7,9-tetramethylxanthin-8-ylidene)platinum(II)
trans-dibromo(N-cyclohexylamine)(1,3,7,9-tetramethylxanthin-8-ylidene)-platinum(II)
trans-dichloro(N-cyclohexylamine)(1,3,7,9-tetramethylxanthin-8-ylidene)-platinum(II)
trans-dinitrato(N-cyclohexylamine)(1,3,7,9-tetramethylxanthin-8-ylidene)-platinum(II)
trans-diiodo(N-cyclohexylamine)[1-methyl-3-(4-methoxybenzyl)imidazol-2-ylidene]platinum(II)
trans-dibromo(N-cyclohexylamine)[1-methyl-3-(4-methoxybenzyl)imidazol-2-ylidene]platinum(II)
trans-dichloro(N-cyclohexylamine)[1-methyl-3-(4-methoxybenzyl)imidazol-2-ylidene]platinum(II)
trans-dinitrato(N-cyclohexylamine)[1-methyl-3-(4-methoxybenzyl)imidazol-2-ylidene]platinum(II)
trans-diiodo(N-cyclohexylamine)[1-methyl-3-(4-trifluoromethylbenzyl)imidazol-2-ylidene]platinum(II)
trans-dibromo(N-cyclohexylamine)[1-methyl-3-(4-trifluoromethylbenzyl)imidazol-2-ylidene]platinum(II)
trans-dichloro(N-cyclohexylamine)[1-methyl-3-(4-trifluoromethylbenzyl)imidazol-2-ylidene]platinum(II)
trans-dinitrato(N-cyclohexylamine)[1-methyl-3-(4-trifluoromethylbenzyl)imidazol-2-ylidene]platinum(II)
trans-diiodo(N-cyclohexylamine)[1,3-dibenzylimidazol-2-ylidene]platinum(II)
trans-dibromo(N-cyclohexylamine)[1,3-dibenzylimidazol-2-ylidene]platinum(II)
trans-dichloro(N-cyclohexylamine)[1,3-dibenzylimidazol-2-ylidene]platinum(II)
trans-dinitrato(N-cyclohexylamine)[1,3-dibenzylimidazol-2-ylidene]platinum(II)
trans-diiodo(N-benzylamine)(1,3-dimethylimidazol-2-ylidene)platinum(II)
trans-dibromo(N-benzylamine)(1,3-dimethylimidazol-2-ylidene)platinum(II)
trans-dichloro(N-benzylamine)(1,3-dimethylimidazol-2-ylidene)platinum(II)
trans-dinitrato(N-benzylamine)(1,3-dimethylimidazol-2-ylidene)platinum(II)
trans-diiodo[N-4-(trifluoromethyl)benzylamine](1,3-dimethylimidazol-2-ylidene)-platinum(II)
trans-dibromo[N-4-(trifluoromethyl)benzylamine](1,3-dimethylimidazol-2-ylidene)platinum(II)
trans-dichloro[N-4-(trifluoromethyl)benzylamine](1,3-dimethylimidazol-2-ylidene)platinum(II)
trans-dinitrato[N-4-(trifluoromethyl)benzylamine](1,3-dimethylimidazol-2-ylidene)platinum(II)
trans-diiodo(N-cyclohexylamine)[1-methyl-3-vinylimidazol-2-ylidene]platinum(II)
trans-dibromo(N-cyclohexylamine)[1-methyl-3-vinylimidazol-2-ylidene]platinum(II)
trans-dichloro(N-cyclohexylamine)[1-methyl-3-vinylimidazol-2-ylidene]platinum(II)
trans-dinitrato(N-cyclohexylamine)[1-methyl-3-vinylimidazol-2-ylidene]platinum(II)
trans-diiodo(N-exo(+)bicyclo[2.2.1]heptylamine)(1,3-dimethylbenzimidazol-2-ylidene)platinum(II)
trans-dibromo(N-exo(+)bicyclo[2.2.1]heptylamine)(1,3-dimethylbenzimidazol-2-ylidene)platinum(II)
trans-dichloro(N-exo(+)bicyclo[2.2.1]heptylamine)(1,3-dimethylbenzimidazol-2-ylidene)platinum(II)
trans-dinitrato(N-exo(+)bicyclo[2.2.1]heptylamine)(1,3-dimethylbenzimidazol-2-ylidene)platinum(II)
trans-diiodo(N-exo(+)bicyclo[2.2.1]heptylamine)(1,3-dimethylbenzimidazol-2-ylidene)platinum(II)
trans-dibromo(N-exo(−)bicyclo[2.2.1]heptylamine)(1,3-dimethylbenzimidazol-2-ylidene)platinum(II)
trans-dichloro(N-exo(−)bicyclo[2.2.1]heptylamine)(1,3-dimethylbenzimidazol-2-ylidene)platinum(II)
trans-dinitrato(N-exo(−)bicyclo[2.2.1]heptylamine)(1,3-dimethylbenzimidazol-2-ylidene)platinum(II)
trans-diiodo(N-cyclohexylamine)(1,3-dicyclohexylimidazol-2-ylidene)platinum(II)
trans-dibromo(N-cyclohexylamine)(1,3-dicyclohexylimidazol-2-ylidene)platinum(II)
trans-dichloro(N-cyclohexylamine)(1,3-dicyclohexylimidazol-2-ylidene)platinum(II)
trans-dinitrato(N-cyclohexylamine)(1,3-dicyclohexylimidazol-2-ylidene)platinum(II)
trans-diiodo(N-cyclohexylamine)(1-methyl-3-phenyl-1,2,4-triazol-3-ylidene)-platinum(II)
trans-dibromo(N-cyclohexylamine)(1-methyl-3-phenyl-1,2,4-triazol-3-ylidene)-platinum(II)
trans-dichloro(N-cyclohexylamine)(1-methyl-3-phenyl-1,2,4-triazol-3-ylidene)-platinum(II)
trans-dinitrato(N-cyclohexylamine)(1-methyl-3-phenyl-1,2,4-triazol-3-ylidene)-platinum(II)
trans-diiodo(N-cyclohexylamine)[1,3-dimethyl-4-phenylimidazol-2-ylidene]-platinum(II)
trans-dibromo(N-cyclohexylamine)[1,3-dimethyl-4-phenylimidazol-2-ylidene]-platinum(II)
trans-dichloro(N-cyclohexylamine)[1,3-dimethyl-4-phenylimidazol-2-ylidene]-platinum(II)
trans-dinitrato(N-cyclohexylamine)[1,3-dimethyl-4-phenylimidazol-2-ylidene]-platinum(II)
trans-diiodo(N-cyclohexylamine)[3-benzyl-1-methyl-4-phenylimidazol-2-ylidene]platinum(II)
trans-dibromo(N-cyclohexylamine)[3-benzyl-1-methyl-4-phenylimidazol-2-ylidene]platinum(II)
trans-dichloro(N-cyclohexylamine)[3-benzyl-1-methyl-4-phenylimidazol-2-ylidene]platinum(II)
trans-dinitrato(N-cyclohexylamine)[3-benzyl-1-methyl-4-phenylimidazol-2-ylidene]platinum(II)

trans-diiodo(N-cyclohexylamine)[1,3-dimethyl-4,5-diphenylimidazol-2-ylidene]-platinum(II)
trans-dibromo(N-cyclohexylamine)[1,3-dimethyl-4,5-diphenylimidazol-2-ylidene]platinum(II)
trans-dichloro(N-cyclohexylamine)[1,3-dimethyl-4,5-diphenylimidazol-2-ylidene]platinum(II)
trans-dinitrato(N-cyclohexylamine)[1,3-dimethyl-4,5-diphenylimidazol-2-ylidene]platinum(II)
trans-diiodo(N-exo(−)bicyclo[2.2.1]heptylamine)(1,3-dimethylimidazol-2-ylidene)platinum(II)
trans-dibromo(N-exo(−)bicyclo[2.2.1]heptylamine)(1,3-dimethylimidazol-2-ylidene)platinum(II)
trans-dichloro(N-exo(−)bicyclo[2.2.1]heptylamine)(1,3-dimethylimidazol-2-ylidene)platinum(II)
trans-dinitrato(N-exo(−)bicyclo[2.2.1]heptylamine)(1,3-dimethylimidazol-2-ylidene)platinum(II)
trans-diiodo(N-exo(+)bicyclo[2.2.1]heptylamine)(1,3-dimethylimidazol-2-ylidene)platinum(II)
trans-dibromo(N-exo(+)bicyclo[2.2.1]heptylamine)(1,3-dimethylimidazol-2-ylidene)platinum(II)
trans-dichloro(N-exo(+)bicyclo[2.2.1]heptylamine)(1,3-dimethylimidazol-2-ylidene)platinum(II)
trans-dinitrato(N-exo(+)bicyclo[2.2.1]heptylamine)(1,3-dimethylimidazol-2-ylidene)platinum(II)
trans-diiodo(N-exo(+/−)bicyclo[2.2.1]heptylamine)(1,3,7,9-tetramethylxanthin-8-ylidene)platinum(II)
trans-dibromo(N-exo(+/−)bicyclo[2.2.1]heptylamine)(1,3,7,9-tetramethylxanthin-8-ylidene)platinum(II)
trans-dichloro(N-exo(+/−)bicyclo[2.2.1]heptylamine)(1,3,7,9-tetramethylxanthin-8-ylidene)platinum(II)
trans-dinitrato(N-exo(+/−)bicyclo[2.2.1]heptylamine)(1,3,7,9-tetramethylxanthin-8-ylidene)platinum(II)
trans-diiodo(N-cyclopropylamine)(1,3-dimethylimidazol-2-ylidene)platinum(II)
trans-diiodo(N-cyclobutylamine)(1,3-dimethylimidazol-2-ylidene)platinum(II)
trans-diiodo(N-cyclopentylamine)(1,3-dimethylimidazol-2-ylidene)platinum(II)
trans-diiodo(N-cycloheptylamine)(1,3-dimethylimidazol-2-ylidene)platinum(II)
trans-diiodo(N-bicyclo[2.2.2]octylamine)(1,3-dimethylimidazol-2-ylidene)platinum(II)
trans-diiodo(N-endo(+/−)bicyclo[2.2.1]heptylamine)(1,3-dimethylimidazol-2-ylidene)platinum(II)
trans-diiodo(N-exo(+/−)bicyclo[3.2.1]octylamine)(1,3-dimethylimidazol-2-ylidene)platinum(II)
trans-diiodo(N-benzylamine)(1,3-dimethylimidazol-2-ylidene)platinum(II)
trans-diiodo(N-4-methoxybenzylamine)(1,3-dimethylimidazol-2-ylidene)-platinum(II)
trans-diiodo(N-4-trifluoromethylbenzylamine)(1,3-dimethylimidazol-2-ylidene)-platinum(II)
trans-diiodo(N-4-chlorobenzylamine)(1,3-dimethylimidazol-2-ylidene)-platinum(II)
trans-diiodo(N-4-fluorobenzylamine)(1,3-dimethylimidazol-2-ylidene)platinum(II)
trans-diiodo(N-4-bromobenzylamine)(1,3-dimethylimidazol-2-ylidene)platinum(II)
trans-diiodo(N-4-methylbenzylamine)(1,3-dimethylimidazol-2-ylidene)platinum(II)
trans-diiodo(N-3,4-dichlorobenzylamine)(1,3-dimethylimidazol-2-ylidene)-platinum(II)
trans-diiodo(N-3,4-dimethoxybenzylamine)(1,3-dimethylimidazol-2-ylidene)-platinum(II)
trans-diiodo(N-3,4-dimethylbenzylamine)(1,3-dimethylimidazol-2-ylidene)-platinum(II)
trans-diiodo(N-cyclopropylamine)(1,4-dimethyl-1,2,4-triazol-3-ylidene)platinum(II)
trans-diiodo(N-cyclobutylamine)(1,4-dimethyl-1,2,4-triazol-3-ylidene)platinum(II)
trans-diiodo(N-cyclopentylamine)(1,4-dimethyl-1,2,4-triazol-3-ylidene)platinum(II)
trans-diiodo(N-cycloheptylamine)(1,4-dimethyl-1,2,4-triazol-3-ylidene)platinum(II)
trans-diiodo(N-bicyclo[2.2.2]octylamine)(1,4-dimethyl-1,2,4-triazol-3-ylidene)-platinum(II)
trans-diiodo(N-endo(+/−)bicyclo[2.2.1]heptylamine)(1,4-dimethyl-1,2,4-triazol-3-ylidene)-platinum(II)
trans-diiodo(N-exo(+/−)bicyclo[3.2.1]octylamine)(1,4-dimethyl-1,2,4-triazol-3-ylidene)platinum(II)
trans-diiodo(N-benzylamine)(1,4-dimethyl-1,2,4-triazol-3-ylidene)platinum(II)
trans-diiodo(N-4-methoxybenzylamine)(1,4-dimethyl-1,2,4-triazol-3-ylidene)-platinum(II)
trans-diiodo(N-4-trifluoromethylbenzylamine)(1,4-dimethyl-1,2,4-triazol-3-ylidene)platinum(II)
trans-diiodo(N-4-chlorobenzylamine)(1,4-dimethyl-1,2,4-triazol-3-ylidene)-platinum(II)
trans-diiodo(N-4-fluorobenzylamine)(1,4-dimethyl-1,2,4-triazol-3-ylidene)-platinum(II)
trans-diiodo(N-4-bromobenzylamine)(1,4-dimethyl-1,2,4-triazol-3-ylidene)-platinum(II)
trans-diiodo(N-4-methylbenzylamine)(1,4-dimethyl-1,2,4-triazol-3-ylidene)-platinum(II)
trans-diiodo(N-3,4-dichlorobenzylamine)(1,4-dimethyl-1,2,4-triazol-3-ylidene)-platinum(II)
trans-diiodo(N-3,4-dimethoxybenzylamine)(1,4-dimethyl-1,2,4-triazol-3-ylidene)platinum(II)
trans-diiodo(N-3,4-dimethylbenzylamine)(1,4-dimethyl-1,2,4-triazol-3-ylidene)-platinum(II)
trans-diiodo(N-cyclopropylamine)(1-methyl-3-(cyclohexylmethyl)imidazol-2-ylidene)platinum(II)
trans-diiodo(N-cyclobutylamine)(1-methyl-3-(cyclohexylmethyl)imidazol-2-ylidene)platinum(II)
trans-diiodo(N-cyclopentylamine)(1-methyl-3-(cyclohexylmethyl)imidazol-2-ylidene)platinum(II)
trans-diiodo(N-cycloheptylamine)(1-methyl-3-(cyclohexylmethyl)imidazol-2-ylidene)platinum(II)
trans-diiodo(N-bicyclo[2.2.2]octylamine)(1-methyl-3-(cyclohexylmethyl)imidazol-2-ylidene)platinum(II)
trans-diiodo(N-endo(+/−)bicyclo[2.2.1]heptylamine)(1-methyl-3-(cyclohexylmethyl)imidazol-2-ylidene)platinum(II)
trans-diiodo(N-exo(+/−)bicyclo[3.2.1]octylamine)(1-methyl-3-(cyclohexylmethyl)imidazol-2-ylidene)platinum(II)
trans-diiodo(N-benzylamine)(1-methyl-3-(cyclohexylmethyl)imidazol-2-ylidene)-platinum(II)
trans-diiodo(N-4-methoxybenzylamine)(1-methyl-3-(cyclohexylmethyl)-imidazol-2-ylidene)platinum(II)
trans-diiodo(N-4-trifluoromethylbenzylamine)(1-methyl-3-(cyclohexylmethyl)imidazol-2-ylidene)platinum(II)
trans-diiodo(N-4-chlorobenzylamine)(1-methyl-3-(cyclohexylmethyl)imidazol-2-ylidene)platinum(II)
trans-diiodo(N-4-fluorobenzylamine)(1-methyl-3-(cyclohexylmethyl)imidazol-2-ylidene)platinum(II)
trans-diiodo(N-4-bromobenzylamine)(1-methyl-3-(cyclohexylmethyl)imidazol-2-ylidene)platinum(II)
trans-diiodo(N-4-methyl benzylamine)(1-methyl-3-(cyclohexylmethyl)imidazol-2-ylidene)platinum(II)
trans-diiodo(N-3,4-dichlorobenzylamine)(1-methyl-3-(cyclohexylmethyl)imidazol-2-ylidene)platinum(II)

trans-diiodo(N-3,4-dimethoxybenzylamine)(1-methyl-3-(cyclohexylmethyl)-imidazol-2-ylidene)platinum(II)
trans-diiodo(N-3,4-dimethylbenzylamine)(1-methyl-3-(cyclohexylmethyl)imidazol-2-ylidene)platinum(II)
trans-diiodo(N-cyclopropylamine)(1-methyl-3-phenylimidazol-2-ylidene)-platinum(II)
trans-diiodo(N-cyclobutylamine)(1-methyl-3-phenylimidazol-2-ylidene)platinum(II)
trans-diiodo(N-cyclopentylamine)(1-methyl-3-phenylimidazol-2-ylidene)-platinum(II)
trans-diiodo(N-cycloheptylamine)(1-methyl-3-phenylimidazol-2-ylidene)-platinum(II)
trans-diiodo(N-bicyclo[2.2.2]octylamine)(1-methyl-3-phenylimidazol-2-ylidene)-platinum(II)
trans-diiodo(N-endo(+/−)bicyclo[2.2.1]heptylamine)(1-methyl-3-phenylimidazol-2-ylidene)platinum(II)
trans-diiodo(N-exo(+/−)bicyclo[3.2.1]octylamine)(1-methyl-3-phenylimidazol-2-ylidene)platinum(II)
trans-diiodo(N-benzylamine)(1-methyl-3-phenylimidazol-2-ylidene)platinum(II)
trans-diiodo(N-4-methoxybenzylamine)(1-methyl-3-phenylimidazol-2-ylidene)-platinum(II)
trans-diiodo(N-4-trifluoromethylbenzylamine)(1-methyl-3-phenylimidazol-2-ylidene)platinum(II)
trans-diiodo(N-4-chlorobenzylamine)(1-methyl-3-phenylimidazol-2-ylidene)-platinum(II)
trans-diiodo(N-4-fluorobenzylamine)(1-methyl-3-phenylimidazol-2-ylidene)-platinum(II)
trans-diiodo(N-4-bromobenzylamine)(1-methyl-3-phenylimidazol-2-ylidene)-platinum(II)
trans-diiodo(N-4-methylbenzylamine)(1-methyl-3-phenylimidazol-2-ylidene)-platinum(II)
trans-diiodo(N-3,4-dichlorobenzylamine)(1-methyl-3-phenylimidazol-2-ylidene)-platinum(II)
trans-diiodo(N-3,4-dimethoxybenzylamine)(1-methyl-3-phenylimidazol-2-ylidene)platinum(II)
trans-diiodo(N-3,4-dimethylbenzylamine)(1-methyl-3-phenylimidazol-2-ylidene)platinum(II)
trans-diiodo(N-cyclopropylamine)(1,3-dimethylbenzimidazol-2-ylidene)platinum(II)
trans-diiodo(N-cyclobutylamine)(1,3-dimethylbenzimidazol-2-ylidene)platinum(II)
trans-diiodo(N-cyclopentylamine)(1,3-dimethylbenzimidazol-2-ylidene)-platinum(II)
trans-diiodo(N-cycloheptylamine)(1,3-dimethylbenzimidazol-2-ylidene)-platinum(II)
trans-diiodo(N-bicyclo[2.2.2]octylamine)(1,3-dimethylbenzimidazol-2-ylidene)-platinum(II)
trans-diiodo(N-endo(+/−)bicyclo[2.2.1]heptylamine)(1,3-dimethylbenzimidazol-2-ylidene)platinum(II)
trans-diiodo(N-exo(+/−)bicyclo[3.2.1]octylamine)(1,3-dimethylbenzimidazol-2-ylidene)platinum(II)
trans-diiodo(N-benzylamine)(1,3-dimethylbenzimidazol-2-ylidene)platinum(II)
trans-diiodo(N-4-methoxybenzylamine)(1,3-dimethylbenzimidazol-2-ylidene)-platinum(II)
trans-diiodo(N-4-trifluoromethylbenzylamine)(1,3-dimethylbenzimidazol-2-ylidene)platinum(II)
trans-diiodo(N-4-chlorobenzylamine)(1,3-dimethylbenzimidazol-2-ylidene)-platinum(II)
trans-diiodo(N-4-fluorobenzylamine)(1,3-dimethylbenzimidazol-2-ylidene)-platinum(II)
trans-diiodo(N-4-bromobenzylamine)(1,3-dimethylbenzimidazol-2-ylidene)-platinum(II)
trans-diiodo(N-4-methylbenzylamine)(1,3-dimethylbenzimidazol-2-ylidene)-platinum(II)
trans-diiodo(N-3,4-dichlorobenzylamine)(1,3-dimethylbenzimidazol-2-ylidene)-platinum(II)
trans-diiodo(N-3,4-dimethoxybenzylamine)(1,3-dimethylbenzimidazol-2-ylidene)platinum(II)
trans-diiodo(N-3,4-dimethylbenzylamine)(1,3-dimethylbenzimidazol-2-ylidene)-platinum(II)
trans-diiodo(N-cyclopropylamine)(1,3,7,9-tetramethylxanthin-8-ylidene)-platinum(II)
trans-diiodo(N-cyclobutylamine)(1,3,7,9-tetramethylxanthin-8-ylidene)-platinum(II)
trans-diiodo(N-cyclopentylamine)(1,3,7,9-tetramethylxanthin-8-ylidene)-platinum(II)
trans-diiodo(N-cycloheptylamine)(1,3,7,9-tetramethylxanthin-8-ylidene)-platinum(II)
trans-diiodo(N-bicyclo[2.2.2]octylamine)(1,3,7,9-tetramethylxanthin-8-ylidene)-platinum(II)
trans-diiodo(N-endo(+/−)bicyclo[2.2.1]heptylamine)(1,3,7,9-tetramethylxanthin-8-ylidene)platinum(II)
trans-diiodo(N-exo(+/−)bicyclo[3.2.1]octylamine)(1,3,7,9-tetramethylxanthin-8-ylidene)platinum(II)
trans-diiodo(N-benzylamine)(1,3,7,9-tetramethylxanthin-8-ylidene)platinum(II)
trans-diiodo(N-4-methoxybenzylamine)(1,3,7,9-tetramethylxanthin-8-ylidene)-platinum(II)
trans-diiodo(N-4-trifluoromethylbenzylamine)(1,3,7,9-tetramethylxanthin-8-ylidene)platinum(II)
trans-diiodo(N-4-chlorobenzylamine)(1,3,7,9-tetramethylxanthin-8-ylidene)-platinum(II)
trans-diiodo(N-4-fluorobenzylamine)(1,3,7,9-tetramethylxanthin-8-ylidene)-platinum(II)
trans-diiodo(N-4-bromobenzylamine)(1,3,7,9-tetramethylxanthin-8-ylidene)-platinum(II)
trans-diiodo(N-4-methylbenzylamine)(1,3,7,9-tetramethylxanthin-8-ylidene)-platinum(II)
trans-diiodo(N-3,4-dichlorobenzylamine)(1,3,7,9-tetramethylxanthin-8-ylidene)-platinum(II)
trans-diiodo(N-3,4-dimethoxybenzylamine)(1,3,7,9-tetramethylxanthin-8-ylidene)platinum(II)
trans-diiodo(N-3,4-dimethylbenzylamine)(1,3,7,9-tetramethylxanthin-8-ylidene)platinum(II)
trans-diiodo(N-cyclopropylamine)[1-methyl-3-(4-methoxybenzyl)imidazol-2-ylidene]platinum(II)
trans-diiodo(N-cyclobutylamine)[1-methyl-3-(4-methoxybenzyl)imidazol-2-ylidene]platinum(II)
trans-diiodo(N-cyclopentylamine)[1-methyl-3-(4-methoxybenzyl)imidazol-2-ylidene]platinum(II)
trans-diiodo(N-cycloheptylamine)[1-methyl-3-(4-methoxybenzyl)imidazol-2-ylidene]platinum(II)
trans-diiodo(N-bicyclo[2.2.2]octylamine)[1-methyl-3-(4-methoxybenzyl)imidazol-2-ylidene]platinum(II)
trans-diiodo(N-endo(+/−)bicyclo[2.2.1]heptylamine)[1-methyl-3-(4-methoxybenzyl)imidazol-2-ylidene]platinum(II)
trans-diiodo(N-exo(+/−)bicyclo[3.2.1]octylamine)[1-methyl-3-(4-methoxybenzyl)imidazol-2-ylidene]platinum(II)
trans-diiodo(N-benzylamine)[1-methyl-3-(4-methoxybenzyl)imidazol-2-ylidene]-platinum(II)
trans-diiodo(N-4-methoxybenzylamine)[1-methyl-3-(4-methoxybenzyl)imidazol-2-ylidene]platinum(II)
trans-diiodo(N-4-trifluoromethylbenzylamine)[1-methyl-3-(4-methoxybenzyl)-imidazol-2-ylidene]platinum(II)
trans-diiodo(N-4-chlorobenzylamine)[1-methyl-3-(4-methoxybenzyl)imidazol-2-ylidene]platinum(II)
trans-diiodo(N-4-fluorobenzylamine)[1-methyl-3-(4-methoxybenzyl)imidazol-2-ylidene]platinum(II)

trans-diiodo(N-4-bromobenzylamine)[1-methyl-3-(4-methoxybenzyl)imidazol-2-ylidene]platinum(II)
trans-diiodo(N-4-methylbenzylamine)[1-methyl-3-(4-methoxybenzyl)imidazol-2-ylidene]platinum(II)
trans-diiodo(N-3,4-dichlorobenzylamine)[1-methyl-3-(4-methoxybenzyl)imidazol-2-ylidene]platinum(II)
trans-diiodo(N-3,4-dimethoxybenzylamine)[1-methyl-3-(4-methoxybenzyl)-imidazol-2-ylidene]platinum(II)
trans-diiodo(N-3,4-dimethylbenzylamine)[1-methyl-3-(4-methoxybenzyl)imidazol-2-ylidene]platinum(II)
trans-diiodo(N-cyclopropylamine)[1-methyl-3-(4-trifluoromethylbenzyl)imidazol-2-ylidene]platinum(II)
trans-diiodo(N-cyclobutylamine)[1-methyl-3-(4-trifluoromethylbenzyl)imidazol-2-ylidene]platinum(II)
trans-diiodo(N-cyclopentylamine)[1-methyl-3-(4-trifluoromethylbenzyl)imidazol-2-ylidene]platinum(II)
trans-diiodo(N-cycloheptylamine)[1-methyl-3-(4-trifluoromethylbenzyl)imidazol-2-ylidene]platinum(II)
trans-diiodo(N-bicyclo[2.2.2]octylamine)[1-methyl-3-(4-trifluoromethylbenzyl)-imidazol-2-ylidene]platinum(II)
trans-diiodo(N-endo(+/−)bicyclo[2.2.1]heptylamine)[1-methyl-3-(4-trifluoromethylbenzyl)imidazol-2-ylidene]platinum(II)
trans-diiodo(N-exo(+/−)bicyclo[3.2.1]octylamine)[1-methyl-3-(4-trifluoromethyl-benzyl)imidazol-2-ylidene]platinum(II)
trans-diiodo(N-benzylamine)[1-methyl-3-(4-trifluoromethylbenzyl)imidazol-2-ylidene]platinum(II)
trans-diiodo(N-4-methoxybenzylamine)[1-methyl-3-(4-trifluoromethylbenzyl)imidazol-2-ylidene]platinum(II)
trans-diiodo(N-4-trifluoromethylbenzylamine)[1-methyl-3-(4-trifluoromethylbenzyl)imidazol-2-ylidene]platinum(II)
trans-diiodo(N-4-chlorobenzylamine)[1-methyl-3-(4-trifluoromethylbenzyl)imidazol-2-ylidene]platinum(II)
trans-diiodo(N-4-fluorobenzylamine)[1-methyl-3-(4-trifluoromethylbenzyl)imidazol-2-ylidene]platinum(II)
trans-diiodo(N-4-bromobenzylamine)[1-methyl-3-(4-trifluoromethylbenzyl)-imidazol-2-ylidene]platinum(II)
trans-diiodo(N-4-methylbenzylamine)[1-methyl-3-(4-trifluoromethylbenzyl)imidazol-2-ylidene]platinum(II)
trans-diiodo(N-3,4-dichlorobenzylamine)[1-methyl-3-(4-trifluoromethylbenzyl)-imidazol-2-ylidene]platinum(II)
trans-diiodo(N-3,4-dimethoxybenzylamine)[1-methyl-3-(4-trifluoromethylbenzyl)imidazol-2-ylidene]platinum(II)
trans-diiodo(N-3,4-dimethylbenzylamine)[1-methyl-3-(4-trifluoromethylbenzyl)-imidazol-2-ylidene]platinum(II)
trans-diiodo(N-cyclopropylamine)[1-methyl-3-(3-methoxybenzyl)imidazol-2-ylidene]platinum(II)
trans-diiodo(N-cyclobutylamine)[1-methyl-3-(3-methoxybenzyl)imidazol-2-ylidene]platinum(II)
trans-diiodo(N-cyclopentylamine)[1-methyl-3-(3-methoxybenzyl)imidazol-2-ylidene]platinum(II)
trans-diiodo(N-cycloheptylamine)[1-methyl-3-(3-methoxybenzyl)imidazol-2-ylidene]platinum(II)
trans-diiodo(N-bicyclo[2.2.2]octylamine)[1-methyl-3-(3-methoxybenzyl)imidazol-2-ylidene]platinum(II)
trans-diiodo(N-endo(+/−)bicyclo[2.2.1]heptylamine)[1-methyl-3-(3-methoxybenzyl)imidazol-2-ylidene]platinum(II)
trans-diiodo(N-exo(+/−)bicyclo[3.2.1]octylamine)[1-methyl-3-(3-methoxybenzyl)imidazol-2-ylidene]platinum(II)
trans-diiodo(N-benzylamine)[1-methyl-3-(3-methoxybenzyl)imidazol-2-ylidene]-platinum(II)
trans-diiodo(N-4-methoxybenzylamine)[1-methyl-3-(3-methoxybenzyl)imidazol-2-ylidene]platinum(II)
trans-diiodo(N-4-trifluoromethylbenzylamine)[1-methyl-3-(3-methoxybenzyl)-imidazol-2-ylidene]platinum(II)
trans-diiodo(N-4-chlorobenzylamine)[1-methyl-3-(3-methoxybenzyl)imidazol-2-ylidene]platinum(II)
trans-diiodo(N-4-fluorobenzylamine)[1-methyl-3-(3-methoxybenzyl)imidazol-2-ylidene]platinum(II)
trans-diiodo(N-4-bromobenzylamine)[1-methyl-3-(3-methoxybenzyl)imidazol-2-ylidene]platinum(II)
trans-diiodo(N-4-methylbenzylamine)[1-methyl-3-(3-methoxybenzyl)imidazol-2-ylidene]platinum(II)
trans-diiodo(N-3,4-dichlorobenzylamine)[1-methyl-3-(3-methoxybenzyl)imidazol-2-ylidene]platinum(II)
trans-diiodo(N-3,4-dimethoxybenzylamine)[1-methyl-3-(3-methoxybenzyl)-imidazol-2-ylidene]platinum(II)
trans-diiodo(N-3,4-dimethylbenzylamine)[1-methyl-3-(3-methoxybenzyl)imidazol-2-ylidene]platinum(II)
trans-diiodo(N-cyclopropylamine)[1-methyl-3-(3-trifluoromethylbenzyl)imidazol-2-ylidene]platinum(II)
trans-diiodo(N-cyclobutylamine)[1-methyl-3-(3-trifluoromethylbenzyl)imidazol-2-ylidene]platinum(II)
trans-diiodo(N-cyclopentylamine)[1-methyl-3-(3-trifluoromethylbenzyl)imidazol-2-ylidene]platinum(II)
trans-diiodo(N-cycloheptylamine)[1-methyl-3-(3-trifluoromethylbenzyl)imidazol-2-ylidene]platinum(II)
trans-diiodo(N-bicyclo[2.2.2]octylamine)[1-methyl-3-(3-trifluoromethylbenzyl)-imidazol-2-ylidene]platinum(II)
trans-diiodo(N-endo(+/−)bicyclo[2.2.1]heptylamine)[1-methyl-3-(3-trifluoromethylbenzyl)imidazol-2-ylidene]platinum(II)
trans-diiodo(N-exo(+/−)bicyclo[3.2.1]octylamine)[1-methyl-3-(3-trifluoromethyl-benzyl)imidazol-2-ylidene]platinum(II)
trans-diiodo(N-benzylamine)[1-methyl-3-(3-trifluoromethylbenzyl)imidazol-2-ylidene]platinum(II)
trans-diiodo(N-4-methoxybenzylamine)[1-methyl-3-(4-trifluoromethylbenzyl)-imidazol-2-ylidene]platinum(II)
trans-diiodo(N-4-trifluoromethylbenzylamine)[1-methyl-3-(3-trifluoromethylbenzyl)imidazol-2-ylidene]platinum(II)
trans-diiodo(N-4-chlorobenzylamine)[1-methyl-3-(3-trifluoromethylbenzyl)imidazol-2-ylidene]platinum(II)
trans-diiodo(N-4-fluorobenzylamine)[1-methyl-3-(3-trifluoromethylbenzyl)imidazol-2-ylidene]platinum(II)
trans-diiodo(N-4-bromobenzylamine)[1-methyl-3-(3-trifluoromethylbenzyl)-imidazol-2-ylidene]platinum(II)
trans-diiodo(N-4-methylbenzylamine)[1-methyl-3-(3-trifluoromethylbenzyl)-imidazol-2-ylidene]platinum(II)
trans-diiodo(N-3,4-dichlorobenzylamine)[1-methyl-3-(3-trifluoromethylbenzyl)-imidazol-2-ylidene]platinum(II)
trans-diiodo(N-3,4-dimethoxybenzylamine)[1-methyl-3-(3-trifluoromethylbenzyl)imidazol-2-ylidene]platinum(II)
trans-diiodo(N-3,4-dimethylbenzylamine)[1-methyl-3-(3-trifluoromethylbenzyl)-imidazol-2-ylidene]platinum(II)
trans-diiodo(N-cyclopropylamine)[1-methyl-3-(3,4-dimethoxybenzyl)imidazol-2-ylidene]platinum(II)
trans-diiodo(N-cyclobutylamine)[1-methyl-3-(3,4-dimethoxybenzyl)imidazol-2-ylidene]platinum(II)
trans-diiodo(N-cyclopentylamine)[1-methyl-3-(3,4-dimethoxybenzyl)imidazol-2-ylidene]platinum(II)
trans-diiodo(N-cycloheptylamine)[1-methyl-3-(3,4-dimethoxybenzyl)imidazol-2-ylidene]platinum(II)
trans-diiodo(N-bicyclo[2.2.2]octylamine)[1-methyl-3-(3,4-dimethoxybenzyl)-imidazol-2-ylidene]platinum(II)
trans-diiodo(N-endo(+/−)bicyclo[2.2.1]heptylamine)[1-methyl-3-(3,4-dimethoxy-benzyl)imidazol-2-ylidene]platinum(II)

trans-diiodo(N-exo(+/−)bicyclo[3.2.1]octylamine)[1-methyl-3-(3,4-dimethoxy-benzyl)imidazol-2-ylidene]platinum(II)
trans-diiodo(N-benzylamine)[1-methyl-3-(3,4-dimethoxybenzyl)imidazol-2-ylidene]platinum(II)
trans-diiodo(N-4-methoxybenzylamine)[1-methyl-3-(3,4-dimethoxybenzyl)-imidazol-2-ylidene]platinum(II)
trans-diiodo(N-4-trifluoromethylbenzylamine)[1-methyl-3-(3,4-dimethoxybenzyl)imidazol-2-ylidene]platinum(II)
trans-diiodo(N-4-chlorobenzylamine)[1-methyl-3-(3,4-dimethoxybenzyl)imidazol-2-ylidene]platinum(II)
trans-diiodo(N-4-fluorobenzylamine)[1-methyl-3-(3,4-dimethoxybenzyl)imidazol-2-ylidene]platinum(II)
trans-diiodo(N-4-bromobenzylamine)[1-methyl-3-(3,4-dimethoxybenzyl)imidazol-2-ylidene]platinum(II)
trans-diiodo(N-4-methylbenzylamine)[1-methyl-3-(3,4-dimethoxybenzyl)imidazol-2-ylidene]platinum(II)
trans-diiodo(N-3,4-dichlorobenzylamine)[1-methyl-3-(3,4-dimethoxybenzyl)-imidazol-2-ylidene]platinum(II)
trans-diiodo(N-3,4-dimethoxybenzylamine)[1-methyl-3-(3,4-dimethoxybenzyl)-imidazol-2-ylidene]platinum(II)
trans-diiodo(N-3,4-dimethylbenzylamine)[1-methyl-3-(3,4-dimethoxybenzyl)-imidazol-2-ylidene]platinum(II)
trans-diiodo(N-cyclopropylamine)(1,3-dibenzylimidazol-2-ylidene)platinum(II)
trans-diiodo(N-cyclobutylamine)(1,3-dibenzylimidazol-2-ylidene)platinum(II)
trans-diiodo(N-cyclopentylamine)(1,3-dibenzylimidazol-2-ylidene)platinum(II)
trans-diiodo(N-cycloheptylamine)(1,3-dibenzylimidazol-2-ylidene)platinum(II)
trans-diiodo(N-bicyclo[2.2.2]octylamine)(1,3-dibenzylimidazol-2-ylidene)-platinum(II)
trans-diiodo(N-endo(+/−)bicyclo[2.2.1]heptylamine)(1,3-dibenzylimidazol-2-ylidene)platinum(II)
trans-diiodo(N-exo(+/−)bicyclo[3.2.1]octylamine)(1,3-dibenzylimidazol-2-ylidene)platinum(II)
trans-diiodo(N-benzylamine)(1,3-dibenzylimidazol-2-ylidene)platinum(II)
trans-diiodo(N-4-methoxybenzylamine)(1,3-dibenzylimidazol-2-ylidene)platinum(II)
trans-diiodo(N-4-trifluoromethylbenzylamine)(1,3-dibenzylimidazol-2-ylidene)-platinum(II)
trans-diiodo(N-4-chlorobenzylamine)(1,3-dibenzylimidazol-2-ylidene)platinum(II)
trans-diiodo(N-4-fluorobenzylamine)(1,3-dibenzylimidazol-2-ylidene)platinum(II)
trans-diiodo(N-4-bromobenzylamine)(1,3-dibenzylimidazol-2-ylidene)platinum(II)
trans-diiodo(N-4-methylbenzylamine)(1,3-dibenzylimidazol-2-ylidene)platinum(II)
trans-diiodo(N-3,4-dichlorobenzylamine)(1,3-dibenzylimidazol-2-ylidene)-platinum(II)
trans-diiodo(N-3,4-dimethoxybenzylamine)(1,3-dibenzylimidazol-2-ylidene)-platinum(II)
trans-diiodo(N-3,4-dimethylbenzylamine)(1,3-dibenzylimidazol-2-ylidene)-platinum(II)
trans-diiodo(N-cyclopropylamine)(1-methyl-3-vinylimidazol-2-ylidene)platinum(II)
trans-diiodo(N-cyclobutylamine)(1-methyl-3-vinylimidazol-2-ylidene)platinum(II)
trans-diiodo(N-cyclopentylamine)(1-methyl-3-vinylimidazol-2-ylidene)platinum(II)
trans-diiodo(N-cycloheptylamine)(1-methyl-3-vinylimidazol-2-ylidene)platinum(II)
trans-diiodo(N-bicyclo[2.2.2]octylamine)(1-methyl-3-vinylimidazol-2-ylidene)-platinum(II)
trans-diiodo(N-endo(+/−)bicyclo[2.2.1]heptylamine)(1-methyl-3-vinylimidazol-2-ylidene)platinum(II)
trans-diiodo(N-exo(+/−)bicyclo[3.2.1]octylamine)(1-methyl-3-vinylimidazol-2-ylidene)platinum(II)
trans-diiodo(N-benzylamine)(1-methyl-3-vinylimidazol-2-ylidene)platinum(II)
trans-diiodo(N-4-methoxybenzylamine)(1-methyl-3-vinylimidazol-2-ylidene)-platinum(II)
trans-diiodo(N-4-trifluoromethylbenzylamine)(1-methyl-3-vinylimidazol-2-ylidene)platinum(II)
trans-diiodo(N-4-chlorobenzylamine)(1-methyl-3-vinylimidazol-2-ylidene)-platinum(II)
trans-diiodo(N-4-fluorobenzylamine)(1-methyl-3-vinylimidazol-2-ylidene)-platinum(II)
trans-diiodo(N-4-bromobenzylamine)(1-methyl-3-vinylimidazol-2-ylidene)-platinum(II)
trans-diiodo(N-4-methylbenzylamine)(1-methyl-3-vinylimidazol-2-ylidene)-platinum(II)
trans-diiodo(N-3,4-dichlorobenzylamine)(1-methyl-3-vinylimidazol-2-ylidene)-platinum(II)
trans-diiodo(N-3,4-dimethoxybenzylamine)(1-methyl-3-vinylimidazol-2-ylidene)platinum(II)
trans-diiodo(N-3,4-dimethylbenzylamine)(1-methyl-3-vinylimidazol-2-ylidene)-platinum(II)
trans-diiodo(N-cyclopropylamine)(1-methyl-3-ethylimidazol-2-ylidene)platinum(II)
trans-diiodo(N-cyclobutylamine)(1-methyl-3-ethylimidazol-2-ylidene)platinum(II)
trans-diiodo(N-cyclopentylamine)(1-methyl-3-ethylimidazol-2-ylidene)platinum(II)
trans-diiodo(N-cycloheptylamine)(1-methyl-3-ethylimidazol-2-ylidene)platinum(II)
trans-diiodo(N-bicyclo[2.2.2]octylamine)(1-methyl-3-ethylimidazol-2-ylidene)-platinum(II)
trans-diiodo(N-endo(+/−)bicyclo[2.2.1]heptylamine)(1-methyl-3-ethylimidazol-2-ylidene)platinum(II)
trans-diiodo(N-exo(+/−)bicyclo[3.2.1]octylamine)(1-methyl-3-ethylimidazol-2-ylidene)platinum(II)
trans-diiodo(N-benzylamine)(1-methyl-3-ethylimidazol-2-ylidene)platinum(II)
trans-diiodo(N-4-methoxybenzylamine)(1-methyl-3-ethylimidazol-2-ylidene)-platinum(II)
trans-diiodo(N-4-trifluoromethylbenzylamine)(1-methyl-3-ethylimidazol-2-ylidene)platinum(II)
trans-diiodo(N-4-chlorobenzylamine)(1-methyl-3-ethylimidazol-2-ylidene)-platinum(II)
trans-diiodo(N-4-fluorobenzylamine)(1-methyl-3-ethylimidazol-2-ylidene)-platinum(II)
trans-diiodo(N-4-bromobenzylamine)(1-methyl-3-ethylimidazol-2-ylidene)-platinum(II)
trans-diiodo(N-4-methylbenzylamine)(1-methyl-3-ethylimidazol-2-ylidene)-platinum(II)
trans-diiodo(N-3,4-dichlorobenzylamine)(1-methyl-3-ethylimidazol-2-ylidene)-platinum(II)
trans-diiodo(N-3,4-dimethoxybenzylamine)(1-methyl-3-ethylimidazol-2-ylidene)platinum(II)
trans-diiodo(N-3,4-dimethylbenzylamine)(1-methyl-3-ethylimidazol-2-ylidene)-platinum(II)
trans-diiodo(N-cyclopropylamine)(1-methyl-3-isopropyl-2-ylidene)platinum(II)
trans-diiodo(N-cyclobutylamine)(1-methyl-3-isopropylimidazol-2-ylidene)-platinum(II)
trans-diiodo(N-cyclopentylamine)(1-methyl-3-isopropylimidazol-2-ylidene)-platinum(II)
trans-diiodo(N-cycloheptylamine)(1-methyl-3-isopropylimidazol-2-ylidene)-platinum(II)

trans-diiodo(N-bicyclo[2.2.2]octylamine)(1-methyl-3-isopropylimidazol-2-ylidene)platinum(II)
trans-diiodo(N-endo(+/−)bicyclo[2.2.1]heptylamine)(1-methyl-3-isopropylimidazol-2-ylidene)platinum(II)
trans-diiodo(N-exo(+/−)bicyclo[3.2.1]octylamine)(1-methyl-3-isopropylimidazol-2-ylidene)platinum(II)
trans-diiodo(N-benzylamine)(1-methyl-3-isopropylimidazol-2-ylidene)platinum(II)
trans-diiodo(N-4-methoxybenzylamine)(1-methyl-3-isopropylimidazol-2-ylidene)platinum(II)
trans-diiodo(N-4-trifluoromethylbenzylamine)(1-methyl-3-isopropylimidazol-2-ylidene)platinum(II)
trans-diiodo(N-4-chlorobenzylamine)(1-methyl-3-isopropylimidazol-2-ylidene)-platinum(II)
trans-diiodo(N-4-fluorobenzylamine)(1-methyl-3-isopropylimidazol-2-ylidene)-platinum(II)
trans-diiodo(N-4-bromobenzylamine)(1-methyl-3-isopropylimidazol-2-ylidene)-platinum(II)
trans-diiodo(N-4-methylbenzylamine)(1-methyl-3-isopropylimidazol-2-ylidene)-platinum(II)
trans-diiodo(N-3,4-dichlorobenzylamine)(1-methyl-3-isopropylimidazol-2-ylidene)platinum(II)
trans-diiodo(N-3,4-dimethoxybenzylamine)(1-methyl-3-isopropylimidazol-2-ylidene)platinum(II)
trans-diiodo(N-3,4-dimethylbenzylamine)(1-methyl-3-isopropylimidazol-2-ylidene)platinum(II)
trans-diiodo(N-cyclopropylamine)(1-methyl-3-allylimidazol-2-ylidene)platinum(II)
trans-diiodo(N-cyclobutylamine)(1-methyl-3-allylimidazol-2-ylidene)platinum(II)
trans-diiodo(N-cyclopentylamine)(1-methyl-3-allylimidazol-2-ylidene)platinum(II)
trans-diiodo(N-cycloheptylamine)(1-methyl-3-allylimidazol-2-ylidene)platinum(II)
trans-diiodo(N-bicyclo[2.2.2]octylamine)(1-methyl-3-allylimidazol-2-ylidene)-platinum(II)
trans-diiodo(N-endo(+/−)bicyclo[2.2.1]heptylamine)(1-methyl-3-allylimidazol-2-ylidene)platinum(II)
trans-diiodo(N-exo(+/−)bicyclo[3.2.1]octylamine)(1-methyl-3-allylimidazol-2-ylidene)platinum(II)
trans-diiodo(N-benzylamine)(1-methyl-3-allylimidazol-2-ylidene)platinum(II)
trans-diiodo(N-4-methoxybenzylamine)(1-methyl-3-allylimidazol-2-ylidene)-platinum(II)
trans-diiodo(N-4-trifluoromethylbenzylamine)(1-methyl-3-allylimidazol-2-ylidene)platinum(II)
trans-diiodo(N-4-chlorobenzylamine)(1-methyl-3-allylimidazol-2-ylidene)-platinum(II)
trans-diiodo(N-4-fluorobenzylamine)(1-methyl-3-allylimidazol-2-ylidene)platinum(II)
trans-diiodo(N-4-bromobenzylamine)(1-methyl-3-vinylimidazol-2-ylidene)-platinum(II)
trans-diiodo(N-4-methylbenzylamine)(1-methyl-3-allylimidazol-2-ylidene)-platinum(II)
trans-diiodo(N-3,4-dichlorobenzylamine)(1-methyl-3-allylimidazol-2-ylidene)-platinum(II)
trans-diiodo(N-3,4-dimethoxybenzylamine)(1-methyl-3-allylimidazol-2-ylidene)platinum(II)
trans-diiodo(N-3,4-dimethylbenzylamine)(1-methyl-3-allylimidazol-2-ylidene)-platinum(II)
trans-diiodo(N-cyclopropylamine)(1-methyl-3-tert-butylimidazol-2-ylidene)-platinum(II)
trans-diiodo(N-cyclobutylamine)(1-methyl-3-tert-butylimidazol-2-ylidene)-platinum(II)
trans-diiodo(N-cyclopentylamine)(1-methyl-3-tert-butylimidazol-2-ylidene)-platinum(II)
trans-diiodo(N-cycloheptylamine)(1-methyl-3-tert-butylimidazol-2-ylidene)-platinum(II)
trans-diiodo(N-bicyclo[2.2.2]octylamine)(1-methyl-3-tert-butylimidazol-2-ylidene)platinum(II)
trans-diiodo(N-endo(+/−)bicyclo[2.2.1]heptylamine)(1-methyl-3-tert-butylimidazol-2-ylidene)platinum(II)
trans-diiodo(N-exo(+/−)bicyclo[3.2.1]octylamine)(1-methyl-3-tert-butylimidazol-2-ylidene)platinum(II)
trans-diiodo(N-benzylamine)(1-methyl-3-tert-butylimidazol-2-ylidene)platinum(II)
trans-diiodo(N-4-methoxybenzylamine)(1-methyl-3-tert-butylimidazol-2-ylidene)platinum(II)
trans-diiodo(N-4-trifluoromethylbenzylamine)(1-methyl-3-tert-butylimidazol-2-ylidene)platinum(II)
trans-diiodo(N-4-chlorobenzylamine)(1-methyl-3-tert-butylimidazol-2-ylidene)-platinum(II)
trans-diiodo(N-4-fluorobenzylamine)(1-methyl-3-tert-butylimidazol-2-ylidene)-platinum(II)
trans-diiodo(N-4-bromobenzylamine)(1-methyl-3-tert-butylimidazol-2-ylidene)-platinum(II)
trans-diiodo(N-4-methylbenzylamine)(1-methyl-3-tert-butylimidazol-2-ylidene)-platinum(II)
trans-diiodo(N-3,4-dichlorobenzylamine)(1-methyl-3-tert-butylimidazol-2-ylidene)platinum(II)
trans-diiodo(N-3,4-dimethoxybenzylamine)(1-methyl-3-tert-butylimidazol-2-ylidene)platinum(II)
trans-diiodo(N-3,4-dimethylbenzylamine)(1-methyl-3-tert-butylimidazol-2-ylidene)platinum(II)
trans-diiodo(N-cyclopropylamine)(1-methyl-3-cyclohexylimidazol-2-ylidene)-platinum(II)
trans-diiodo(N-cyclobutylamine)(1-methyl-3-cyclohexylimidazol-2-ylidene)-platinum(II)
trans-diiodo(N-cyclopentylamine)(1-methyl-3-cyclohexylimidazol-2-ylidene)-platinum(II)
trans-diiodo(N-cycloheptylamine)(1-methyl-3-cyclohexylimidazol-2-ylidene)-platinum(II)
trans-diiodo(N-bicyclo[2.2.2]octylamine)(1-methyl-3-cyclohexylimidazol-2-ylidene)platinum(II)
trans-diiodo(N-endo(+/−)bicyclo[2.2.1]heptylamine)(1-methyl-3-cyclohexylimidazol-2-ylidene)platinum(II)
trans-diiodo(N-exo(+/−)bicyclo[3.2.1]octylamine)(1-methyl-3-cyclohexylimidazol-2-ylidene)platinum(II)
trans-diiodo(N-benzylamine)(1-methyl-3-cyclohexylimidazol-2-ylidene)platinum(II)
trans-diiodo(N-4-methoxybenzylamine)(1-methyl-3-cyclohexylimidazol-2-ylidene)platinum(II)
trans-diiodo(N-4-trifluoromethylbenzylamine)(1-methyl-3-cyclohexylimidazol-2-ylidene)platinum(II)
trans-diiodo(N-4-chlorobenzylamine)(1-methyl-3-cyclohexylimidazol-2-ylidene)-platinum(II)
trans-diiodo(N-4-fluorobenzylamine)(1-methyl-3-cyclohexylimidazol-2-ylidene)-platinum(II)
trans-diiodo(N-4-bromobenzylamine)(1-methyl-3-cyclohexylimidazol-2-ylidene)platinum(II)
trans-diiodo(N-4-methyl benzylamine)(1-methyl-3-cyclohexylimidazol-2-ylidene)platinum(II)
trans-diiodo(N-3,4-dichlorobenzylamine)(1-methyl-3-cyclohexylimidazol-2-ylidene)platinum(II)
trans-diiodo(N-3,4-dimethoxybenzylamine)(1-methyl-3-cyclohexylimidazol-2-ylidene)platinum(II)
trans-diiodo(N-3,4-dimethylbenzylamine)(1-methyl-3-cyclohexylimidazol-2-ylidene)platinum(II)
trans-diiodo(N-cyclopropylamine)(1-methyl-3-cyclohexylmethylimidazol-2-ylidene)platinum(II)
trans-diiodo(N-cyclobutylamine)(1-methyl-3-cyclohexylmethylimidazol-2-ylidene)platinum(II)

trans-diiodo(N-cyclopentylamine)(1-methyl-3-cyclohexylmethylimidazol-2-ylidene)platinum(II)
trans-diiodo(N-cycloheptylamine)(1-methyl-3-cyclohexylmethylimidazol-2-ylidene)platinum(II)
trans-diiodo(N-bicyclo[2.2.2]octylamine)(1-methyl-3-cyclohexylmethylimidazol-2-ylidene)platinum(II)
trans-diiodo(N-endo(+/−)bicyclo[2.2.1]heptylamine)(1-methyl-3-cyclohexylmethylimidazol-2-ylidene)platinum(II)
trans-diiodo(N-exo(+/−)bicyclo[3.2.1]octylamine)(1-methyl-3-cyclohexylmethyl-imidazol-2-ylidene)platinum(II)
trans-diiodo(N-benzylamine)(1-methyl-3-cyclohexylmethylimidazol-2-ylidene)-platinum(II)
trans-diiodo(N-4-methoxybenzylamine)(1-methyl-3-cyclohexylmethylimidazol-2-ylidene)platinum(II)
trans-diiodo(N-4-trifluoromethylbenzylamine)(1-methyl-3-cyclohexylmethyl-imidazol-2-ylidene)platinum(II)
trans-diiodo(N-4-chlorobenzylamine)(1-methyl-3-cyclohexylmethylimidazol-2-ylidene)platinum(II)
trans-diiodo(N-4-fluorobenzylamine)(1-methyl-3-cyclohexylmethylimidazol-2-ylidene)platinum(II)
trans-diiodo(N-4-bromobenzylamine)(1-methyl-3-cyclohexylmethylimidazol-2-ylidene)platinum(II)
trans-diiodo(N-4-methylbenzylamine)(1-methyl-3-cyclohexylmethylimidazol-2-ylidene)platinum(II)
trans-diiodo(N-3,4-dichlorobenzylamine)(1-methyl-3-cyclohexylmethylimidazol-2-ylidene)platinum(II)
trans-diiodo(N-3,4-dimethoxybenzylamine)(1-methyl-3-cyclohexylmethylimidazol-2-ylidene)platinum(II)
trans-diiodo(N-3,4-dimethylbenzylamine)(1-methyl-3-cyclohexylmethylimidazol-2-ylidene)platinum(II)
trans-diiodo(N-cyclopropylamine)(1-methyl-3-cyclopropylimidazol-2-ylidene)-platinum(II)
trans-diiodo(N-cyclobutylamine)(1-methyl-3-cyclopropylimidazol-2-ylidene)-platinum(II)
trans-diiodo(N-cyclopentylamine)(1-methyl-3-cyclopropylimidazol-2-ylidene)-platinum(II)
trans-diiodo(N-cycloheptylamine)(1-methyl-3-cyclopropylimidazol-2-ylidene)-platinum(II)
trans-diiodo(N-bicyclo[2.2.2]octylamine)(1-methyl-3-cyclopropylimidazol-2-ylidene)platinum(II)
trans-diiodo(N-endo(+/−)bicyclo[2.2.1]heptylamine)(1-methyl-3-cyclopropyl-imidazol-2-ylidene)platinum(II)
trans-diiodo(N-exo(+/−)bicyclo[3.2.1]octylamine)(1-methyl-3-cyclopropylimidazol-2-ylidene)platinum(II)
trans-diiodo(N-benzylamine)(1-methyl-3-cyclopropylimidazol-2-ylidene)platinum(II)
trans-diiodo(N-4-methoxybenzylamine)(1-methyl-3-cyclopropylimidazol-2-ylidene)platinum(II)
trans-diiodo(N-4-trifluoromethylbenzylamine)(1-methyl-3-cyclopropylimidazol-2-ylidene)platinum(II)
trans-diiodo(N-4-chlorobenzylamine)(1-methyl-3-cyclopropylimidazol-2-ylidene)platinum(II)
trans-diiodo(N-4-fluorobenzylamine)(1-methyl-3-cyclopropylimidazol-2-ylidene)platinum(II)
trans-diiodo(N-4-bromobenzylamine)(1-methyl-3-cyclopropylimidazol-2-ylidene)platinum(II)
trans-diiodo(N-4-methylbenzylamine)(1-methyl-3-cyclopropylimidazol-2-ylidene)platinum(II)
trans-diiodo(N-3,4-dichlorobenzylamine)(1-methyl-3-cyclopropylimidazol-2-ylidene)platinum(II)
trans-diiodo(N-3,4-dimethoxybenzylamine)(1-methyl-3-cyclopropylimidazol-2-ylidene)platinum(II)
trans-diiodo(N-3,4-dimethylbenzylamine)(1-methyl-3-cyclopropylimidazol-2-ylidene)platinum(II)
trans-diiodo(N-cyclopropylamine)(1-methyl-3-cyclopropylmethylimidazol-2-ylidene)platinum(II)
trans-diiodo(N-cyclobutylamine)(1-methyl-3-cyclopropylmethylimidazol-2-ylidene)platinum(II)
trans-diiodo(N-cyclopentylamine)(1-methyl-3-cyclopropylmethylimidazol-2-ylidene)platinum(II)
trans-diiodo(N-cycloheptylamine)(1-methyl-3-cyclopropylmethylimidazol-2-ylidene)platinum(II)
trans-diiodo(N-bicyclo[2.2.2]octylamine)(1-methyl-3-cyclopropylmethylimidazol-2-ylidene)platinum(II)
trans-diiodo(N-endo(+/−)bicyclo[2.2.1]heptylamine)(1-methyl-3-cyclopropylmethylimidazol-2-ylidene)platinum(II)
trans-diiodo(N-exo(+/−)bicyclo[3.2.1]octylamine)(1-methyl-3-cyclopropylmethyl-imidazol-2-ylidene)platinum(II)
trans-diiodo(N-benzylamine)(1-methyl-3-cyclopropylmethylimidazol-2-ylidene)-platinum(II)
trans-diiodo(N-4-methoxybenzylamine)(1-methyl-3-cyclopropylmethylimidazol-2-ylidene)platinum(II)
trans-diiodo(N-4-trifluoromethylbenzylamine)(1-methyl-3-cyclopropylmethylimidazol-2-ylidene)platinum(II)
trans-diiodo(N-4-chlorobenzylamine)(1-methyl-3-cyclopropylmethylimidazol-2-ylidene)platinum(II)
trans-diiodo(N-4-fluorobenzylamine)(1-methyl-3-cyclopropylmethylimidazol-2-ylidene)platinum(II)
trans-diiodo(N-4-bromobenzylamine)(1-methyl-3-cyclopropylmethylimidazol-2-ylidene)platinum(II)
trans-diiodo(N-4-methylbenzylamine)(1-methyl-3-cyclopropylmethylimidazol-2-ylidene)platinum(II)
trans-diiodo(N-3,4-dichlorobenzylamine)(1-methyl-3-cyclopropylmethylimidazol-2-ylidene)platinum(II)
trans-diiodo(N-3,4-dimethoxybenzylamine)(1-methyl-3-cyclopropylmethylimidazol-2-ylidene)platinum(II)
trans-diiodo(N-3,4-dimethylbenzylamine)(1-methyl-3-cyclopropylmethylimidazol-2-ylidene)platinum(II)
trans-diiodo(N-cyclopropylamine)(1,3-dicyclohexylimidazol-2-ylidene)platinum(II)
trans-diiodo(N-cyclobutylamine)(1,3-dicyclohexylimidazol-2-ylidene)platinum(II)
trans-diiodo(N-cyclopentylamine)(1,3-dicyclohexylimidazol-2-ylidene)platinum(II)
trans-diiodo(N-cycloheptylamine)(1,3-dicyclohexylimidazol-2-ylidene)platinum(II)
trans-diiodo(N-bicyclo[2.2.2]octylamine)(1,3-dicyclohexylimidazol-2-ylidene)-platinum(II)
trans-diiodo(N-endo(+/−)bicyclo[2.2.1]heptylamine)(1,3-dicyclohexylimidazol-2-ylidene)platinum(II)
trans-diiodo(N-exo(+/−)bicyclo[3.2.1]octylamine)(1,3-dicyclohexylimidazol-2-ylidene)platinum(II)
trans-diiodo(N-benzylamine)(1,3-dicyclohexylimidazol-2-ylidene)platinum(II)
trans-diiodo(N-4-methoxybenzylamine)(1,3-dicyclohexylimidazol-2-ylidene)-platinum(II)
trans-diiodo(N-4-trifluoromethylbenzylamine)(1,3-dicyclohexylimidazol-2-ylidene)platinum(II)
trans-diiodo(N-4-chlorobenzylamine)(1,3-dicyclohexylimidazol-2-ylidene)-platinum(II)
trans-diiodo(N-4-fluorobenzylamine)(1,3-dicyclohexylimidazol-2-ylidene)-platinum(II)
trans-diiodo(N-4-bromobenzylamine)(1,3-dicyclohexylimidazol-2-ylidene)-platinum(II)
trans-diiodo(N-4-methylbenzylamine)(1,3-dicyclohexylimidazol-2-ylidene)-platinum(II)
trans-diiodo(N-3,4-dichlorobenzylamine)(1,3-dicyclohexylimidazol-2-ylidene)-platinum(II)
trans-diiodo(N-3,4-dimethoxybenzylamine)(1,3-dicyclohexylimidazol-2-ylidene)-platinum(II)

trans-diiodo(N-3,4-dimethylbenzylamine)(1,3-dicyclohexylimidazol-2-ylidene)-platinum(II)
trans-diiodo(N-cyclopropylamine)(1,3-dicyclohexylmethylimidazol-2-ylidene)-platinum(II)
trans-diiodo(N-cyclobutylamine)(1,3-dicyclohexylmethylimidazol-2-ylidene)-platinum(II)
trans-diiodo(N-cyclopentylamine)(1,3-dicyclohexylmethylimidazol-2-ylidene)-platinum(II)
trans-diiodo(N-cycloheptylamine)(1,3-dicyclohexylmethylimidazol-2-ylidene)-platinum(II)
trans-diiodo(N-bicyclo[2.2.2]octylamine)(1,3-dicyclohexylmethylimidazol-2-ylidene)platinum(II)
trans-diiodo(N-endo(+/−)bicyclo[2.2.1]heptylamine)(1,3-dicyclohexylmethyl-imidazol-2-ylidene)platinum(II)
trans-diiodo(N-exo(+/−)bicyclo[3.2.1]octylamine)(1,3-dicyclohexylmethylimidazol-2-ylidene)platinum(II)
trans-diiodo(N-benzylamine)(1,3-dicyclohexylmethylimidazol-2-ylidene)platinum(II)
trans-diiodo(N-4-methoxybenzylamine)(1,3-dicyclohexylimidazol-2-ylidene)-platinum(II)
trans-diiodo(N-4-trifluoromethylbenzylamine)(1,3-dicyclohexylmethylimidazol-2-ylidene)platinum(II)
trans-diiodo(N-4-chlorobenzylamine)(1,3-dicyclohexylmethylimidazol-2-ylidene)platinum(II)
trans-diiodo(N-4-fluorobenzylamine)(1,3-dicyclohexylmethylimidazol-2-ylidene)platinum(II)
trans-diiodo(N-4-bromobenzylamine)(1,3-dicyclohexylmethylimidazol-2-ylidene)platinum(II)
trans-diiodo(N-4-methylbenzylamine)(1,3-dicyclohexylmethylimidazol-2-ylidene)platinum(II)
trans-diiodo(N-3,4-dichlorobenzylamine)(1,3-dicyclohexylmethylimidazol-2-ylidene)platinum(II)
trans-diiodo(N-3,4-dimethoxybenzylamine)(1,3-dicyclohexylmethylimidazol-2-ylidene)platinum(II)
trans-diiodo(N-3,4-dimethylbenzylamine)(1,3-dicyclohexylmethylimidazol-2-ylidene)platinum(II)
trans-diiodo(N-cyclopropylamine)(1,3-dicyclopropylmethylimidazol-2-ylidene)-platinum(II)
trans-diiodo(N-cyclobutylamine)(1,3-dicyclopropylmethylimidazol-2-ylidene)-platinum(II)
trans-diiodo(N-cyclopentylamine)(1,3-dicyclopropylmethylimidazol-2-ylidene)-platinum(II)
trans-diiodo(N-cycloheptylamine)(1,3-dicyclopropylmethylimidazol-2-ylidene)-platinum(II)
trans-diiodo(N-bicyclo[2.2.2]octylamine)(1,3-dicyclopropylmethylimidazol-2-ylidene)platinum(II)
trans-diiodo(N-endo(+/−)bicyclo[2.2.1]heptylamine)(1,3-dicyclopropylmethyl-imidazol-2-ylidene)platinum(II)
trans-diiodo(N-exo(+/−)bicyclo[3.2.1]octylamine)(1,3-dicyclopropylmethylimidazol-2-ylidene)platinum(II)
trans-diiodo(N-benzylamine)(1,3-dicyclopropylmethylimidazol-2-ylidene)platinum(II)
trans-diiodo(N-4-methoxybenzylamine)(1,3-dicyclopropylimidazol-2-ylidene)-platinum(II)
trans-diiodo(N-4-trifluoromethylbenzylamine)(1,3-dicyclopropylmethylimidazol-2-ylidene)platinum(II)
trans-diiodo(N-4-chlorobenzylamine)(1,3-dicyclopropylmethylimidazol-2-ylidene)platinum(II)
trans-diiodo(N-4-fluorobenzylamine)(1,3-dicyclopropylmethylimidazol-2-ylidene)platinum(II)
trans-diiodo(N-4-bromobenzylamine)(1,3-dicyclopropylmethylimidazol-2-ylidene)platinum(II)
trans-diiodo(N-4-methylbenzylamine)(1,3-dicyclohexylmethylimidazol-2-ylidene)platinum(II)
trans-diiodo(N-3,4-dichlorobenzylamine)(1,3-dicyclohexylmethylimidazol-2-ylidene)platinum(II)
trans-diiodo(N-3,4-dimethoxybenzylamine)(1,3-dicyclohexylmethylimidazol-2-ylidene)platinum(II)
trans-diiodo(N-3,4-dimethylbenzylamine)(1,3-dicyclohexylmethylimidazol-2-ylidene)platinum(II)
trans-diiodo(N-cyclopropylamine)(1-methyl-3-phenyl-1,2,4-triazol-5-ylidene)platinum(II)
trans-diiodo(N-cyclobutylamine)(1-methyl-3-phenyl-1,2,4-triazol-5-ylidene)platinum(II)
trans-diiodo(N-cyclopentylamine)(1-methyl-3-phenyl-1,2,4-triazol-5-ylidene)-platinum(II)
trans-diiodo(N-cycloheptylamine)(1-methyl-3-phenyl-1,2,4-triazol-5-ylidene)-platinum(II)
trans-diiodo(N-bicyclo[2.2.2]octylamine)(1-methyl-3-phenyl-1,2,4-triazol-5-ylidene)platinum(II)
trans-diiodo(N-endo(+/−)bicyclo[2.2.1]heptylamine)(1-methyl-3-phenyl-1,2,4-triazol-5-ylidene)platinum(II)
trans-diiodo(N-exo(+/−)bicyclo[3.2.1]octylamine)(1-methyl-3-phenyl-1,2,4-triazol-5-ylidene)platinum(II)
trans-diiodo(N-benzylamine)(1-methyl-3-phenyl-1,2,4-triazol-5-ylidene)platinum(II)
trans-diiodo(N-4-methoxybenzylamine)(1-methyl-3-phenyl-1,2,4-triazol-5-ylidene)platinum(II)
trans-diiodo(N-4-trifluoromethylbenzylamine)(1-methyl-3-phenyl-1,2,4-triazol-5-ylidene)platinum(II)
trans-diiodo(N-4-chlorobenzylamine)(1-methyl-3-phenyl-1,2,4-triazol-5-ylidene)platinum(II)
trans-diiodo(N-4-fluorobenzylamine)(1-methyl-3-phenyl-1,2,4-triazol-5-ylidene)platinum(II)
trans-diiodo(N-4-bromobenzylamine)(1-methyl-3-phenyl-1,2,4-triazol-5-ylidene)platinum(II)
trans-diiodo(N-4-methylbenzylamine)(1-methyl-3-phenyl-1,2,4-triazol-5-ylidene)platinum(II)
trans-diiodo(N-3,4-dichlorobenzylamine)(1-methyl-3-phenyl-1,2,4-triazol-5-ylidene)platinum(II)
trans-diiodo(N-3,4-dimethoxybenzylamine)(1-methyl-3-phenyl-1,2,4-triazol-5-ylidene)platinum(II)
trans-diiodo(N-3,4-dimethylbenzylamine)(1-methyl-3-phenyl-1,2,4-triazol-5-ylidene)platinum(II)
trans-diiodo(N-cyclopropylamine)(1-methyl-3-cyclohexyl-1,2,4-triazol-5-ylidene)platinum(II)
trans-diiodo(N-cyclobutylamine)(1-methyl-3-cyclohexyl-1,2,4-triazol-5-ylidene)platinum(II)
trans-diiodo(N-cyclopentylamine)(1-methyl-3-cyclohexyl-1,2,4-triazol-5-ylidene)platinum(II)
trans-diiodo(N-cycloheptylamine(1-methyl-3-cyclohexyl-1,2,4-triazol-5-ylidene)platinum(II)
trans-diiodo(N-bicyclo[2.2.2]octylamine)(1-methyl-3-cyclohexyl-1,2,4-triazol-5-ylidene)platinum(II)
trans-diiodo(N-endo(+/−)bicyclo[2.2.1]heptylamine)(1-methyl-3-cyclohexyl-1,2,4-triazol-5-ylidene)platinum(II)
trans-diiodo(N-exo(+/−)bicyclo[3.2.1]octylamine)(1-methyl-3-cyclohexyl-1,2,4-triazol-5-ylidene)platinum(II)
trans-diiodo(N-benzylamine)(1-methyl-3-cyclohexyl-1,2,4-triazol-5-ylidene)platinum(II)
trans-diiodo(N-4-methoxybenzylamine)(1-methyl-3-cyclohexyl-1,2,4-triazol-5-ylidene)platinum(II)
trans-diiodo(N-4-trifluoromethylbenzylamine)(1-methyl-3-cyclohexyl-1,2,4-triazol-5-ylidene)platinum(II)
trans-diiodo(N-4-chlorobenzylamine)(1-methyl-3-cyclohexyl-1,2,4-triazol-5-ylidene)platinum(II)
trans-diiodo(N-4-fluorobenzylamine)(1-methyl-3-cyclohexyl-1,2,4-triazol-5-ylidene)platinum(II)
trans-diiodo(N-4-bromobenzylamine)(1-methyl-3-cyclohexyl-1,2,4-triazol-5-ylidene)platinum(II)
trans-diiodo(N-4-methylbenzylamine)(1-methyl-3-cyclohexyl-1,2,4-triazol-5-ylidene)platinum(II)

trans-diiodo(N-3,4-dichlorobenzylamine)(1-methyl-3-cyclohexyl-1,2,4-triazol-5-ylidene)platinum(II)
trans-diiodo(N-3,4-dimethoxybenzylamine)(1-methyl-3-cyclohexyl-1,2,4-triazol-5-ylidene)platinum(II)
trans-diiodo(N-cyclopropylamine)(1-methyl-3-benzyl-1,2,4-triazol-5-ylidene)platinum(II)
trans-diiodo(N-cyclobutylamine)(1-methyl-3-benzyl-1,2,4-triazol-5-ylidene)platinum(II)
trans-diiodo(N-cyclopentylamine)(1-methyl-3-benzyl-1,2,4-triazol-5-ylidene)platinum(II)
trans-diiodo(N-cycloheptylamine)(1-methyl-3-benzyl-1,2,4-triazol-5-ylidene)platinum(II)
trans-diiodo(N-bicyclo[2.2.2]octylamine)(1-methyl-3-benzyl-1,2,4-triazol-5-ylidene)platinum(II)
trans-diiodo(N-endo(+/−)bicyclo[2.2.1]heptylamine)(1-methyl-3-benzyl-1,2,4-triazol-5-ylidene)platinum(II)
trans-diiodo(N-exo(+/−)bicyclo[3.2.1]octylamine)(1-methyl-3-benzyl-1,2,4-triazol-5-ylidene)platinum(II)
trans-diiodo(N-benzylamine)(1-methyl-3-benzyl-1,2,4-triazol-5-ylidene)platinum(II)
trans-diiodo(N-4-methoxybenzylamine)(1-methyl-3-benzyl-1,2,4-triazol-5-ylidene)platinum(II)
trans-diiodo(N-4-trifluoromethylbenzylamine)(1-methyl-3-benzyl-1,2,4-triazol-5-ylidene)platinum(II)
trans-diiodo(N-4-chlorobenzylamine)(1-methyl-3-benzyl-1,2,4-triazol-5-ylidene)platinum(II)
trans-diiodo(N-4-fluorobenzylamine)(1-methyl-3-benzyl-1,2,4-triazol-5-ylidene)platinum(II)
trans-diiodo(N-4-bromobenzylamine)(1-methyl-3-benzyl-1,2,4-triazol-5-ylidene)platinum(II)
trans-diiodo(N-4-methylbenzylamine)(1-methyl-3-benzyl-1,2,4-triazol-5-ylidene)platinum(II)
trans-diiodo(N-3,4-dichlorobenzylamine)(1-methyl-3-benzyl-1,2,4-triazol-5-ylidene)platinum(II)
trans-diiodo(N-3,4-di methoxybenzylamine)(1-methyl-3-benzyl-1,2,4-triazol-5-ylidene)platinum(II)
trans-diiodo(N-cyclopropylamine)[1-methyl-3-(4-trifluoromethylbenzyl)-1,2,4-triazol-5-ylidene]platinum(II)
trans-diiodo(N-cyclobutylamine)[1-methyl-3-(4-trifluoromethylbenzyl)-1,2,4-triazol-5-ylidene]platinum(II)
trans-diiodo(N-cyclopentylamine)[1-methyl-3-(4-trifluoromethyl benzyl)-1,2,4-triazol-5-ylidene]platinum(II)
trans-diiodo(N-cycloheptylamine)[1-methyl-3-(4-trifluoromethylbenzyl)-1,2,4-triazol-5-ylidene]platinum(II)
trans-diiodo(N-bicyclo[2.2.2]octylamine)[1-methyl-3-(4-trifluoromethyl benzyl)-1,2,4-triazol-5-ylidene]platinum(II)
trans-diiodo(N-endo(+/−)bicyclo[2.2.1]heptylamine)[1-methyl-3-(4-trifluoromethylbenzyl)-1,2,4-triazol-5-ylidene]platinum(II)
trans-diiodo(N-exo(+/−)bicyclo[3.2.1]octylamine)[1-methyl-3-(4-trifluoromethylbenzyl)-1,2,4-triazol-5-ylidene]platinum(II)
trans-diiodo(N-benzylamine)[1-methyl-3-(4-trifluoromethylbenzyl)-1,2,4-triazol-5-ylidene]platinum(II)
trans-diiodo(N-4-methoxybenzylamine)[1-methyl-3-(4-trifluoromethylbenzyl)-1,2,4-triazol-5-ylidene]platinum(II)
trans-diiodo(N-4-trifluoromethylbenzylamine)[1-methyl-3-(4-trifluoromethylbenzyl)-1,2,4-triazol-5-ylidene]platinum(II)
trans-diiodo(N-4-chlorobenzylamine)[1-methyl-3-(4-trifluoromethylbenzyl)-1,2,4-triazol-5-ylidene]platinum(II)
trans-diiodo(N-4-fluorobenzylamine)[1-methyl-3-(4-trifluoromethylbenzyl)-1,2,4-triazol-5-ylidene]platinum(II)
trans-diiodo(N-4-bromobenzylamine)[1-methyl-3-(4-trifluoromethylbenzyl)-1,2,4-triazol-5-ylidene]platinum(II)
trans-diiodo(N-4-methylbenzylamine)[1-methyl-3-(4-trifluoromethylbenzyl)-1,2,4-triazol-5-ylidene]platinum(II)
trans-diiodo(N-3,4-dichlorobenzylamine)[1-methyl-3-(4-trifluoromethylbenzyl)-1,2,4-triazol-5-ylidene]platinum(II)
trans-diiodo(N-3,4-dimethoxybenzylamine)[1-methyl-3-(4-trifluoromethylbenzyl)-1,2,4-triazol-5-ylidene]platinum(II)
trans-diiodo(N-cyclopropylamine)(1,3-dibenzyl-1,2,4-triazol-5-ylidene)platinum(II)
trans-diiodo(N-cyclobutylamine)(1,3-dibenzyl-1,2,4-triazol-5-ylidene)platinum(II)
trans-diiodo(N-cyclopentylamine)(1,3-dibenzyl-1,2,4-triazol-5-ylidene)platinum(II)
trans-diiodo(N-cycloheptylamine)(1,3-dibenzyl-1,2,4-triazol-5-ylidene)platinum(II)
trans-diiodo(N-bicyclo[2.2.2]octylamine)(1,3-dibenzyl-1,2,4-triazol-5-ylidene)-platinum(II)
trans-diiodo(N-endo(+/−)bicyclo[2.2.1]heptylamine)(1,3-dibenzyl-1,2,4-triazol-5-ylidene)platinum(II)
trans-diiodo(N-exo(+/−)bicyclo[3.2.1]octylamine)(1,3-dibenzyl-1,2,4-triazol-5-ylidene)platinum(II)
trans-diiodo(N-benzylamine)(1,3-dibenzyl-1,2,4-triazol-5-ylidene)platinum(II)
trans-diiodo(N-4-methoxybenzylamine)(1,3-dibenzyl-1,2,4-triazol-5-ylidene)-platinum(II)
trans-diiodo(N-4-trifluoromethylbenzylamine)(1,3-dibenzyl-1,2,4-triazol-5-ylidene)platinum(II)
trans-diiodo(N-4-chlorobenzylamine)(1,3-dibenzyl-1,2,4-triazol-5-ylidene)platinum(II)
trans-diiodo(N-4-fluorobenzylamine)(1,3-dibenzyl-1,2,4-triazol-5-ylidene)-platinum(II)
trans-diiodo(N-4-bromobenzylamine)(1,3-dibenzyl-1,2,4-triazol-5-ylidene)-platinum(II)
trans-diiodo(N-4-methylbenzylamine)(1,3-dibenzyl-1,2,4-triazol-5-ylidene)platinum(II)
trans-diiodo(N-3,4-dichlorobenzylamine)(1,3-dibenzyl-1,2,4-triazol-5-ylidene)-platinum(II)
trans-diiodo(N-3,4-dimethoxybenzylamine)(1,3-dibenzyl-1,2,4-triazol-5-ylidene)platinum(II)
trans-diiodo(N-cyclopropylamine)[1,3-dimethyl-4-phenylimidazol-2-ylidene]-platinum(II)
trans-diiodo(N-cyclobutylamine)[1,3-dimethyl-4-phenylimidazol-2-ylidene]-platinum(II)
trans-diiodo(N-cyclopentylamine)[1,3-dimethyl-4-phenylimidazol-2-ylidene]-platinum(II)
trans-diiodo(N-cycloheptylamine)[1,3-dimethyl-4-phenylimidazol-2-ylidene]-platinum(II)
trans-diiodo(N-bicyclo[2.2.2]octylamine)[1,3-dimethyl-4-phenylimidazol-2-ylidene]platinum(II)
trans-diiodo(N-endo(+/−)bicyclo[2.2.1]heptylamine)[1,3-dimethyl-4-phenylimidazol-2-ylidene]platinum(II)
trans-diiodo(N-exo(+/−)bicyclo[3.2.1]octylamine)[1,3-dimethyl-4-phenylimidazol-2-ylidene]platinum(II)
trans-diiodo(N-benzylamine)[1,3-dimethyl-4-phenylimidazol-2-ylidene]platinum(II)
trans-diiodo(N-4-methoxybenzylamine)[1,3-dimethyl-4-phenylimidazol-2-ylidene]platinum(II)
trans-diiodo(N-4-trifluoromethylbenzylamine)[1,3-dimethyl-4-phenylimidazol-2-ylidene]platinum(II)
trans-diiodo(N-4-chlorobenzylamine)[1,3-dimethyl-4-phenylimidazol-2-ylidene]-platinum(II)
trans-diiodo(N-4-fluorobenzylamine)[1,3-dimethyl-4-phenylimidazol-2-ylidene]-platinum(II)
trans-diiodo(N-4-bromobenzylamine)[1,3-dimethyl-4-phenylimidazol-2-ylidene]-platinum(II)

trans-diiodo(N-4-methylbenzylamine)[1,3-dimethyl-4-phenylimidazol-2-ylidene]platinum(II)
trans-diiodo(N-3,4-dichlorobenzylamine)[1,3-dimethyl-4-phenylimidazol-2-ylidene]platinum(II)
trans-diiodo(N-3,4-dimethoxybenzylamine)[1,3-dimethyl-4-phenylimidazol-2-ylidene]platinum(II)
trans-diiodo(N-3,4-dimethylbenzylamine)[1,3-dimethyl-4-phenylimidazol-2-ylidene]platinum(II)
trans-diiodo(N-cyclopropylamine)[3-benzyl-1-methyl-4-phenylimidazol-2-ylidene]platinum(II)
trans-diiodo(N-cyclobutylamine)[3-benzyl-1-methyl-4-phenylimidazol-2-ylidene]platinum(II)
trans-diiodo(N-cyclopentylamine)[3-benzyl-1-methyl-4-phenylimidazol-2-ylidene]platinum(II)
trans-diiodo(N-cycloheptylamine)[3-benzyl-1-methyl-4-phenylimidazol-2-ylidene]platinum(II)
trans-diiodo(N-bicyclo[2.2.2]octylamine)[3-benzyl-1-methyl-4-phenylimidazol-2-ylidene]platinum(II)
trans-diiodo(N-endo(+/−)bicyclo[2.2.1]heptylamine)[3-benzyl-1-methyl-4-phenylimidazol-2-ylidene]platinum(II)
trans-diiodo(N-exo(+/−)bicyclo[3.2.1]octylamine)[3-benzyl-1-methyl-4-phenyl-imidazol-2-ylidene]platinum(II)
trans-diiodo(N-benzylamine)[3-benzyl-1-methyl-4-phenylimidazol-2-ylidene]-platinum(II)
trans-diiodo(N-4-methoxybenzylamine)[3-benzyl-1-methyl-4-phenylimidazol-2-ylidene]platinum(II)
trans-diiodo(N-4-trifluoromethylbenzylamine)[3-benzyl-1-methyl-4-phenylimidazol-2-ylidene]platinum(II)
trans-diiodo(N-4-chlorobenzylamine)[3-benzyl-1-methyl-4-phenylimidazol-2-ylidene]platinum(II)
trans-diiodo(N-4-fluorobenzylamine)[3-benzyl-1-methyl-4-phenylimidazol-2-ylidene]platinum(II)
trans-diiodo(N-4-bromobenzylamine)[3-benzyl-1-methyl-4-phenylimidazol-2-ylidene]platinum(II)
trans-diiodo(N-4-methylbenzylamine)[3-benzyl-1-methyl-4-phenylimidazol-2-ylidene]platinum(II)
trans-diiodo(N-3,4-dichlorobenzylamine)[3-benzyl-1-methyl-4-phenylimidazol-2-ylidene]platinum(II)
trans-diiodo(N-3,4-dimethoxybenzylamine)[3-benzyl-1-methyl-4-phenylimidazol-2-ylidene]platinum(II)
trans-diiodo(N-3,4-dimethylbenzylamine)[3-benzyl-1-methyl-4-phenylimidazol-2-ylidene]platinum(II)
trans-diiodo(N-cyclopropylamine)[1,3-dimethyl-4,5-diphenylimidazol-2-ylidene]-platinum(II)
trans-diiodo(N-cyclobutylamine)[1,3-dimethyl-4,5-diphenylimidazol-2-ylidene]-platinum(II)
trans-diiodo(N-cyclopentylamine)[1,3-dimethyl-4,5-diphenylimidazol-2-ylidene]-platinum(II)
trans-diiodo(N-cycloheptylamine)[1,3-dimethyl-4,5-diphenylimidazol-2-ylidene]-platinum(II)
trans-diiodo(N-bicyclo[2.2.2]octylamine)[1,3-dimethyl-4,5-diphenylimidazol-2-ylidene]platinum(II)
trans-diiodo(N-endo(+/−)bicyclo[2.2.1]heptylamine)[1,3-dimethyl-4,5-diphenyl-imidazol-2-ylidene]platinum(II)
trans-diiodo(N-exo(+/−)bicyclo[3.2.1]octylamine)[1,3-dimethyl-4,5-diphenylimidazol-2-ylidene]platinum(II)
trans-diiodo(N-benzylamine)[1,3-dimethyl-4,5-diphenylimidazol-2-ylidene]-platinum(II)
trans-diiodo(N-4-methoxybenzylamine)[1,3-dimethyl-4,5-diphenylimidazol-2-ylidene]platinum(II)
trans-diiodo(N-4-trifluoromethylbenzylamine)[1,3-dimethyl-4,5-diphenylimidazol-2-ylidene]platinum(II)
trans-diiodo(N-4-chlorobenzylamine)[1,3-dimethyl-4,5-diphenylimidazol-2-ylidene]platinum(II)
trans-diiodo(N-4-fluorobenzylamine)[1,3-dimethyl-4,5-diphenylimidazol-2-ylidene]platinum(II)
trans-diiodo(N-4-bromobenzylamine)[1,3-dimethyl-4,5-diphenylimidazol-2-ylidene]platinum(II)
trans-diiodo(N-4-methylbenzylamine)[1,3-dimethyl-4,5-diphenylimidazol-2-ylidene]platinum(II)
trans-diiodo(N-3,4-dichlorobenzylamine)[1,3-dimethyl-4,5-diphenylimidazol-2-ylidene]platinum(II)
trans-diiodo(N-3,4-dimethoxybenzylamine)[1,3-dimethyl-4,5-diphenylimidazol-2-ylidene]platinum(II)
trans-diiodo(N-3,4-dimethylbenzylamine)[1,3-dimethyl-4,5-diphenylimidazol-2-ylidene]platinum(II)

In accordance with the invention, the compounds of general formula (I) may be prepared according to the method which follows.

Scheme 1:

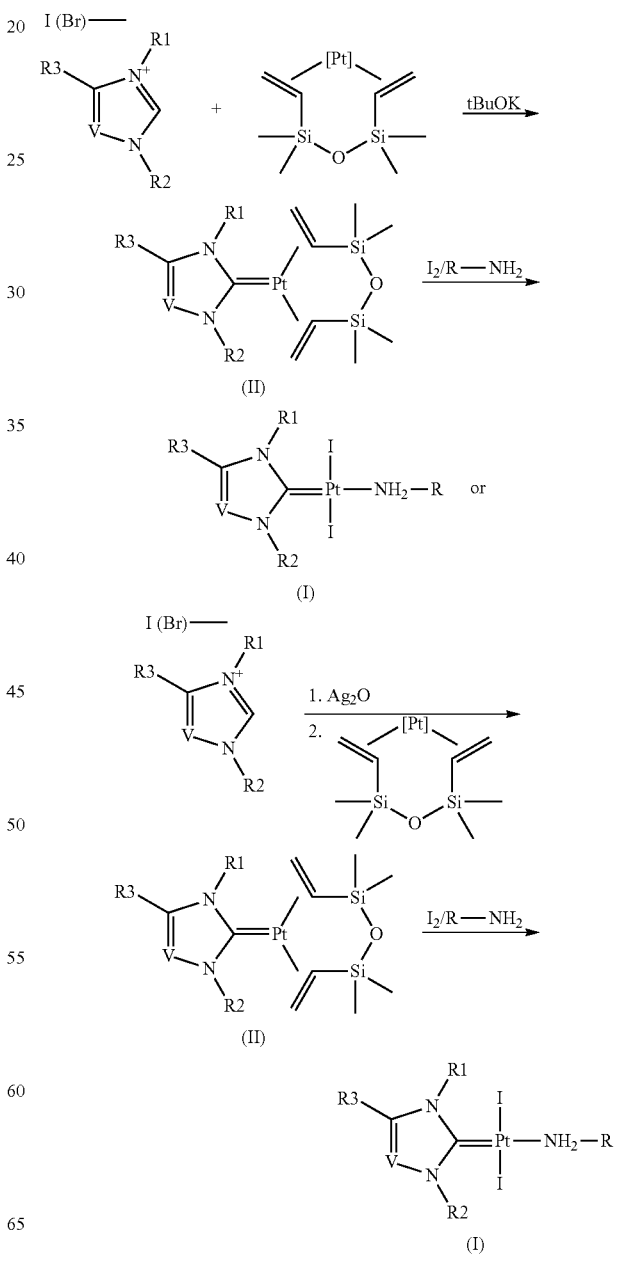

-continued

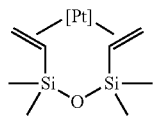

indicates the "Karstedt catalyst", predominantly consisting of the bimetallic complex

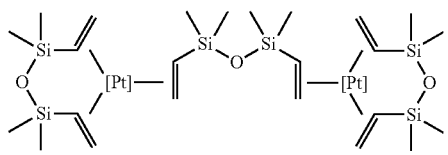

Or according to the following scheme 2:

Scheme 2:

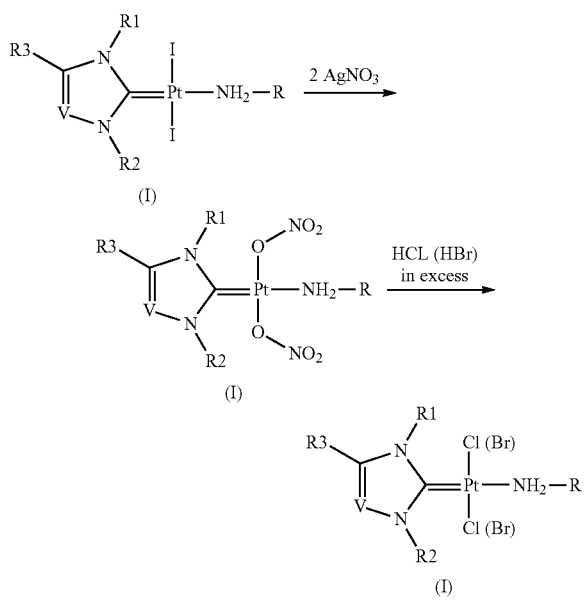

Or according to the following scheme 3:

Scheme 3:

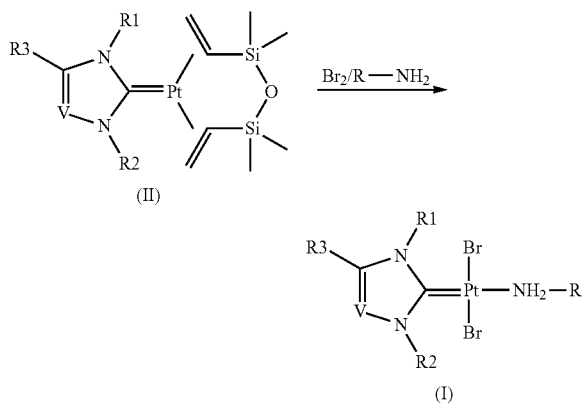

In scheme 1, the starting compounds and the reagents, when their mode of preparation is not described, are commercially available or are described in the literature, or they may be prepared according to methods described therein or which are known to persons skilled in the art.

The compounds of formula (II) are useful as intermediates for the synthesis of the compounds of formula (I). They are described, in particular as catalysts, for example in patent WO 02/098888, or in the Journal of Organometallic Chemistry (2005), 290(24-25), 6156-68, or in Organometallics (2007), 26(24), 5782-85 or in Organometallics (2007), 26(24), 5782-85 or in the Journal of Materials Chemistry (2007), 17(15), 1476-84.

The following examples describe the preparation of some compounds in accordance with the invention. These examples are not limiting and merely illustrate the present invention. The numbers for the compounds exemplified refer to those given in the table below, which illustrates the chemical structures and the physical properties of some compounds according to the invention.

EXAMPLE 1 trans-diiodo(N-cyclohexylamine)(1,3-dimethylimidazol-2-ylidene)platinum(II)

To a solution of the complex (1,3-dimethylimidazol-2-ylidene)(1,3-divinyl-1,1,3,3-tetramethyldisiloxane)platinum (0) (0.3 g; 0.68 mmol)—which was obtained according to G. Berthon Gelloz et al, Journal of Organometallic Chemistry (2005), 290(24-25), 6156-68—in 40 ml of toluene at 0° C., there is added a solution of diiodine (0.17 g; 0.68 mmol) in 20 ml of toluene. Next, 78 µl of cyclohexylamine (0.68 mmol) are added to the mixture. The reaction mixture is stirred for 4 h at room temperature and then evaporated to dryness. The residue obtained is purified by flash chromatography by elution with a mixture of heptane and ethyl acetate (70/30 by volume), 0.27 g (61%) of trans-diiodo(N-cyclohexylamine)(1,3-dimethylimidazol-2-ylidene)platinum(II) is thus recovered in the form of a yellow powder whose characteristics are the following:

$^1$H NMR spectrum (300 MHz, CDCl$_3$, 20° C.) δ [ppm]= 1.1-1.5 (5H), 1.64 (m, 1H), 1.78 (m, 3H), 2.29 (m, 2H), 2.90 (br, 2H), 3.25 (m, 1H), 3.85 (s, 6H), 6.79 (s, 2H).

Elemental analysis, % measured (calc.) for $C_{11}H_{21}I_2N_3Pt$: C, 20.79 (20.51); H, 3.21 (3.29); N, 6.26 (6.48).

EXAMPLE 2 trans-diiodo(N-cyclohexylamine)(1,4-dimethyl-1,2,4-triazol-5-ylidene)platinum(II)

Step 1: [1,4-dimethyl-1,2,4-triazol-5-ylidene(1,3-divinyl-1,1,3,3-tetramethyl-disiloxane)]platinum(0)

To a solution of 0.1 M 1,3-divinyl-1,1,3,3-tetramethyldisiloxane)platinum(0) in xylene (4.2 ml; 0.42 mmol), there is added 1,4-dimethyl-1,2,4-triazol-1-ium iodide (0.10 g; 0.42 mmol). The mixture is stirred for 1 h 30 min at room temperature and then cooled to 0° C. Next, 0.06 g of potassium tert-butoxide (0.56 mmol). The reaction mixture is stirred for 2 days at room temperature and then evaporated to dryness. The residue obtained is purified by flash chromatography by elution with a mixture of heptane and ethyl acetate (80/20 by volume), 0.18 g (93%) of [1,4-dimethyl-1,2,4-triazol-5-ylidene(1,3-divinyl-1,1,3,3-tetramethyldisiloxane)]platinum (0) is thus recovered whose characteristics are the following:

$^1$H NMR spectrum (300 MHz, CDCl$_3$, 20° C.) δ [ppm]=− 0.28 (s, 6H), 0.32 (s, 6H), 1.8-2.1 (m, 4H), 2.2-2.4 (m, 2H), 3.55 (s, 3H), 3.73 (s, 3H), 8.02 (s, 1H).

Step 2: trans-diiodo(N-cyclohexylamine)(1,4-dimethyl-1,2,4-triazol-5-ylidene)platinum(II)

To a solution of the complex [1,4-dimethyl-1,2,4-triazol-5-ylidene(1,3-divinyl-1,1,3,3-tetramethyldisiloxane)]platinum(0) (0.22 g; 0.5 mmol) in 20 ml of toluene at 0° C., there is added a solution of diiodine (0.13 g; 0.5 mmol) in 30 ml of toluene. Next, 60 µl of cyclohexylamine (0.5 mmol) are added to the mixture. The reaction mixture is stirred for 16 h at room temperature and then evaporated to dryness. The residue obtained is purified by flash chromatography by elution with a mixture of heptane and ethyl acetate (70/30 by volume), 0.19 g (60%) of trans-diiodo(N-cyclohexylamine)(1,4-dimethyl-1,2,4-triazol-5-ylidene)platinum(II) is thus recovered in the form of yellow crystals whose characteristics are the following:

$^1$H NMR spectrum (500 MHz, CDCl$_3$, 20° C.) δ [ppm]= 1.1-1.4 (5H), 1.65 (m, 1H), 1.79 (m, 2H), 2.28 (m, 2H), 3.01 (br, 2H), 3.27 (m, 1H), 3.86 (s, 3H), 4.05 (s, 3H), 7.82 (s, 1H).

EXAMPLE 3 trans-diiodo(N-cyclohexylamine)(1-methyl-3-cyclohexylmethylimidazol-2-ylidene)platinum(II)

Step 1: 1-methyl-3-cyclohexylmethylimidazolium iodide

A solution of 1-methylimidazole (0.9 ml; 10.8 mmol) in cyclohexylmethyl bromide (1.7 ml; 11.9 mmol) is heated at 100° C. for 16 hours, and then the volatiles are evaporated under vacuum. The residue obtained is recrystallized from 5 ml of ethyl acetate, thus making it possible to obtain 2.8 g of 1-methyl-3-cyclohexylmethylimidazolium iodide, whose characteristics are the following:

$^1$H NMR spectrum (300 MHz, CDCl$_3$, 20° C.) δ [ppm]= 1.0-1.9 (11H), 4.13 (s, 3H), 4.15 (d, 2H), 7.26 (s, 1H), 7.42 (s, 1H), 10.48 (s, 1H).

Step 2: [1-methyl-3-cyclohexylmethyl imidazol-2-ylidene(1,3-divinyl-1,1,3,3-tetramethyldisiloxane)]platinum(0)

To a mixture of 0.1 M 1,3-divinyl-1,1,3,3-tetramethyldisiloxane)platinum(0) in xylene (6 ml; 0.60 mmol) and 1-methyl-3-methylcyclohexylimidazolium, obtained in step 1, (0.15 g; 0.60 mmol), there is added potassium tert-butoxide (0.09 g; 0.80 mmol) at 0° C. The reaction mixture is stirred for 16 h at room temperature and then evaporated to dryness. The residue obtained is purified by flash chromatography by elution with a mixture of heptane and ethyl acetate (90/10 by volume), 0.30 g (83%) of [1-methyl-3-cyclohexylmethylimidazol-2-ylidene(1,3-divinyl-1,1,3,3-tetramethyldisiloxane)]platinum(0) is thus recovered whose characteristics are the following:

$^1$H NMR spectrum (300 MHz, CDCl$_3$, 20° C.) δ [ppm]=− 0.26 (s, 6H), 0.33 (s, 6H), 0.8-0.9 (m, 3H), 1.1-1.2 (m, 4H), 1.5-2.0 (m, 8H), 2.21 (d, 2H), 3.50 (s, 3H), 3.68 (m, 2H), 6.97 (m, 2H).

Step 3: trans-diiodo(N-cyclohexylamine)(1-methyl-3-cyclohexylmethylimidazol-2-ylidene)platinum(II)

To a solution of the complex of [1-methyl-3-cyclohexylmethylimidazol-2-ylidene(1,3-divinyl-1,1,3,3-tetramethyldisiloxane)]platinum(0) (0.28 g; 0.5 mmol) in 20 ml of toluene at 0° C., there is added a solution of diiodine (0.13 g; 0.5 mmol) in 30 ml of toluene. Next, 60 µl of cyclohexylamine (0.5 mmol) are added to the mixture. The reaction mixture is stirred for 16 h at room temperature and then evaporated to dryness. The residue obtained is purified by flash chromatography by elution with a mixture of heptane and ethyl acetate (90/10 by volume), 0.23 g (62%) of trans-diiodo(N-cyclohexylamine)(1-methyl-3-cyclohexylmethylimidazol-2-ylidene)platinum(II) is thus recovered in the form of yellow crystals whose characteristics are the following:

$^1$H NMR spectrum (500 MHz, CDCl$_3$, 20° C.) δ [ppm]= 1.0-1.4 (12H), 1.6-1.9 (m, 8H), 2.30 (m, 2H), 2.55 (m, 1H), 2.92 (br, 2H), 3.26 (m, 1H), 3.86 (s, 3H), 4.07 (d, 2H, J=7.5 Hz), 6.74 (d, 1H), 6.77 (d, 1H).

Elemental analysis (%) found (calc.) for C$_{17}$H$_{31}$I$_2$N$_3$Pt: C, 28.12 (28.11); H, 4.11 (4.30); N, 5.59 (5.79).

ORTEP diagram—X-ray diffraction. Crystals obtained from a solution of the complex in chloroform by slow evaporation of the solvent. (See FIG. 1.)

EXAMPLE 4 trans-diiodo(N-cyclohexylamine)(1-methyl-3-phenylimidazol-2-ylidene)platinum(II)

To a solution of the complex [1-methyl-3-(phenyl)imidazol-2-ylidene(1,3-divinyl-1,1,3,3-tetramethyldisiloxane)] platinum(0) (0.14 g; 0.26 mmol)—which was obtained according to D. Brissy et al., Organometallics (2007), 26(24), 5782-85—in 10 ml of toluene at 0° C., there is added a solution of diiodine (0.07 g; 0.26 mmol) in 15 ml of toluene. Next, 33 µl of cyclohexylamine (0.29 mmol) are added to the mixture. The reaction mixture is stirred for 16 h at room temperature and then evaporated to dryness. The residue obtained is purified by flash chromatography by elution with a mixture of heptane and ethyl acetate (90/10 by volume), 0.07 g (38%) of trans-diiodo(N-cyclohexylamine)(1-methyl-3-phenylimidazol-2-ylidene)platinum(II) is thus recovered in the form of a yellow powder whose characteristics are the following:

$^1$H NMR spectrum (300 MHz, CDCl$_3$, 20° C.) δ [ppm]= 1.0-1.4 (5H), 1.5-1.8 (3H), 2.07 (m, 2H), 2.78 (br, 2H), 3.08 (m, 1H), 3.97 (s, 3H), 6.97 (d, 2H), 7.06 (d, 2H), 7.4-7.6 (3H), 7.85 (m, 2H).

Mass spectrum (HRMS, ESI positive mode) calculated for C$_{16}$H$_{23}$I$_2$N$_3$Pt.Na: 728.9527; found for C$_{16}$H$_{23}$I$_2$N$_3$NaPt: 728.9527.

EXAMPLE 5 trans-diiodo(N-cyclohexylamine)(1-methyl-3-benzylimidazol-2-ylidene)platinum(II)

Step 1: [1-methyl-3-benzylimidazol-2-ylidene (1,3-divinyl-1,1,3,3-tetramethyldi-siloxane)]platinum(0)

To a mixture of 0.1 M 1,3-divinyl-1,1,3,3-tetramethyldisiloxane)platinum(0) in xylene (3.3 ml; 0.33 mmol) and 1-methyl-3-benzylimidazolium iodide (0.10 g; 0.33 mmol)— which was obtained according to A. M. Magill et al., *Journal of Organometallic Chemistry* (2001), 617-618, 546-60— there is added potassium tert-butoxide (0.06 g; 0.52 mmol) at 0° C. The reaction mixture is stirred for 16 h at room temperature and then evaporated to dryness. The residue obtained is purified by flash chromatography by elution with a mixture of heptane and ethyl acetate (90/10 by volume), 0.15 g (82%) of [1-methyl-3-benzylimidazol-2-ylidene(1,3-divinyl-1,1,3, 3-tetramethyldisiloxane)]platinum(0) is thus obtained whose characteristics are the following:

$^1$H NMR spectrum (300 MHz, CDCl$_3$, 20° C.) δ [ppm]=−0.33 (s, 6H), 0.34 (s, 6H), 1.8-2.0 (m, 4H), 2.23 (d, 2H), 3.56 (s, 3H), 5.14 (s, 2H), 6.91 (d, 1H), 7.02 (d, 1H), 7.1-7.2 (m, 2H), 7.2-7.4 (m, 3H).

Step 2: trans-diiodo(N-cyclohexylamine)(1-methyl-3-benzylimidazol-2-ylidene)-platinum(II)

To a solution of the complex [1-methyl-3-benzylimidazol-2-ylidene](1,3-divinyl-1,1,3,3-tetramethyldisiloxane)]platinum(0) (0.11 g, 0.2 mmol) in 8 ml of toluene at 0° C., there is added a solution of diiodine (0.05 g, 0.2 mmol) in 12 ml of toluene. Next, 25 µl of cyclohexylamine (0.22 mmol) are added to the mixture. The reaction mixture is stirred for 16 h at room temperature and then evaporated to dryness. The residue obtained is purified by flash chromatography by elution with a mixture of heptane and ethyl acetate (90/10 by volume), 0.07 g (49%) of trans-diiodo(N-cyclohexylamine)(1-methyl-3-benzylimidazol-2-ylidene)platinum(II) is thus recovered in the form of yellow crystals whose characteristics are the following:

$^1$H NMR spectrum (300 MHz, CDCl$_3$, 20° C.) δ [ppm]= 1.1-1.9 (8H), 2.28 (m, 2H), 2.93 (br, 2H), 3.25 (m, 1H), 3.89 (s, 3H), 5.59 (s, 2H), 6.56 (d, 2H), 6.77 (s, 2H), 7.3-7.5 (5H).

Figure 2:
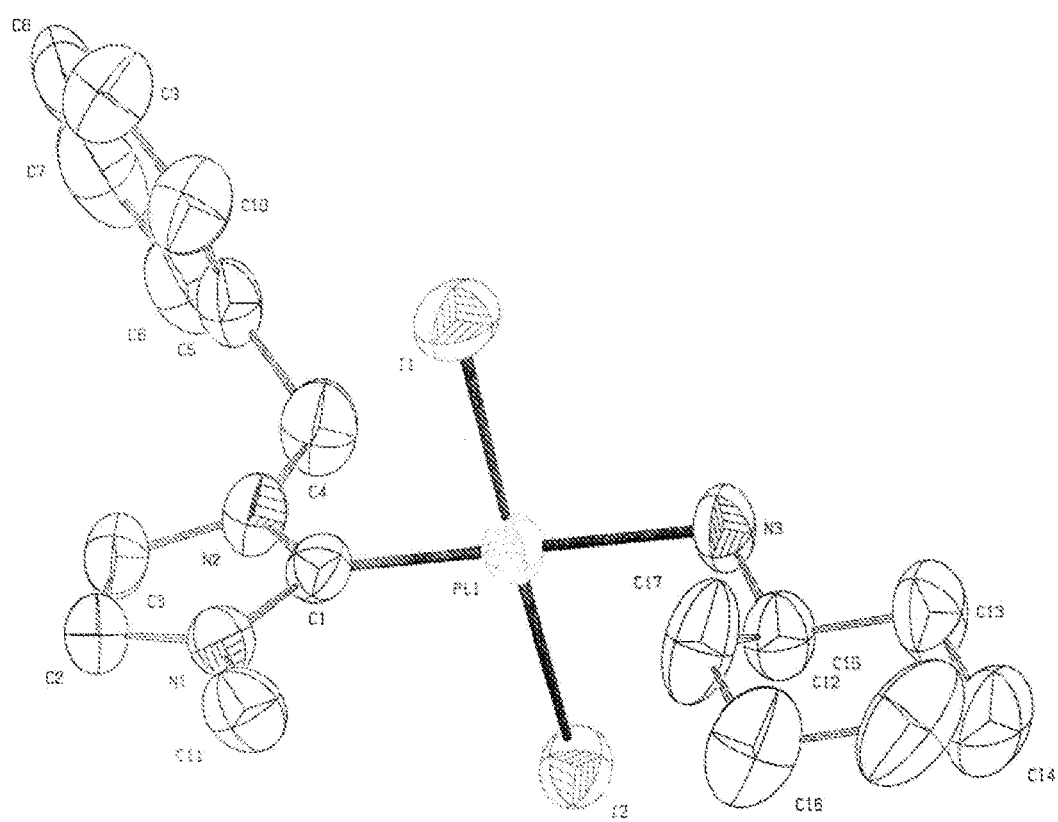
FIG. 2: Depicts an ORTEP diagram representing the structure of the compound of Example 5, described herein.

ORTEP diagram—X-ray diffraction. Crystals obtained from a solution of the complex in chloroform, by slow evaporation of the solvent. (See FIG. 2.)

EXAMPLE 6 trans-diiodo(N-exo(+/−)bicyclo[2.2.1]heptylamine)(1,3-dimethyl-imidazol-2-ylidene)platinum(II)

In a 100 ml three-necked flask under argon, there is dissolved 0.310 g (0.649 mmol) of (1,3-dimethylimidazol-2-ylidene)(1,3-divinyl-1,1,3,3-tetramethyldisiloxane)platinum(0)—which was obtained according to G Berthon-Gelloz et al., Journal of Organometallic Chemistry (2005), 690(24-25), 6156-68—in 50 ml of toluene and then the mixture is cooled to 0° C. There are then successively added dropwise at 0° C. a solution of 0.167 g (0.649 mmol) of diiodine in 10 ml of toluene and then 72.2 mg (0.649 mmol) of racemic exo-norbornylamine. The reaction medium is then stirred at room temperature for 4 h. The reaction medium is evaporated to dryness. The residue thus obtained is purified by flash chromatography, eluting with a mixture of cyclohexane and ethyl acetate (85/15 by volume). 188 mg (44%) of trans-diiodo(N-exo(+/−)bicyclo[2.2.1]heptylamine)[1,3-dimethylimidazol-2-ylidene]platinum(II) are thus obtained in the form of fine, pale yellow crystals whose characteristics are the following:

Rf=0.22 (silica gel; mixture of 80% of cyclohexane and 20% of ethyl acetate)

$^1$H NMR spectrum (CDCl$_3$, 20° C.), δ [ppm]: 1.13 (m, 1H), 1.25 (m, 2H), 1.42-1.60 (m, 3H), 1.73 (m, 1H), 1.78 (m, 1H), 2.33 (t, J=4.6 Hz, 1H), 2.44 (d, J=4.6 Hz, 1H), 2.88 (m, 2H), 3.44 (m, 1H) 3.85 (s, 6H) 6.79 (s, 2H).

EXAMPLE 7 trans-diiodo(N-exo(+/−)bicyclo[2.2.1]heptylamine)(1,3-dimethyl-benzimidazol-2-ylidene)platinum(II)

In a 100 ml three-necked flask under argon, there is dissolved 0.316 g (0.6 mmol) of (1,3-dimethylbenzimidazol-2-ylidene)(1,3-divinyl-1,1,3,3-tetramethyldisiloxane)platinum(0)—which was obtained according to G Berthon-Gelloz et al., Journal of Organometallic Chemistry (2005), 690(24-25), 6156-68—in 55 ml of toluene and then the mixture is cooled to 0° C. There are then successively added dropwise at 0° C. a solution of 0.152 g (0.6 mmol) of diiodine in 10 ml of toluene and then 66.7 mg (0.6 mmol) of racemic exo-norbornylamine. The reaction medium is then stirred at room temperature for 6 h. The reaction medium is evaporated to dryness. The residue thus obtained is purified by flash chromatography, eluting with a mixture of cyclohexane and ethyl acetate (90/10 by volume). 207 mg (49%) of trans-diiodo(N-exo(+/−)bicyclo[2.2.1]heptylamine)[1,3-dimethylbenzimidazol-2-ylidene]-platinum(II) are thus obtained in the form of yellow crystals whose characteristics are the following:

Rf=0.27 (silica gel; mixture of 85% of cyclohexane and 15% of ethyl acetate)

$^1$H NMR spectrum (CDCl$_3$, 20° C.), δ [ppm]: 1.15 (m, 1H), 1.27 (m, 2H), 1.42-1.64 (m, 3H), 1.76 (m, 1H), 1.85 (m, 1H), 2.37 (t, J=4.6 Hz, 1H), 2.48 (d, J=4.6 Hz, 1H), 2.91-3.13 (broad m, 2H), 3.51 (m, 1H), 4.08 (s, 6H), 7.23-7.29 (m, 2H), 7.30-7.37 (m, 2H).

EXAMPLE 8 trans-diiodo(N-cyclohexylamine)(1,3-dimethylbenzimidazol-2-ylidene)platinum(II)

In a 100 ml three-necked flask under argon, there is dissolved 0.316 g (0.6 mmol) of (1,3-dimethylbenzimidazol-2-ylidene)(1,3-divinyl-1,1,3,3-tetramethyldisiloxane)platinum(0)—which was obtained according to G Berthon-Gelloz et al., Journal of Organometallic Chemistry (2005), 690(24-25), 6156-68—in 55 ml of toluene and then the mixture is cooled to 0° C. There are then successively added dropwise at 0° C. a solution of 0.152 g (0.6 mmol) of diiodine in 10 ml of toluene and then 68.6 µl (0.6 mmol) of cyclohexylamine. The reaction medium is then stirred at room temperature for 6 h. The reaction medium is evaporated to dryness. The residue thus obtained is purified by flash chromatography, eluting with a mixture of cyclohexane and ethyl acetate (90/10 by volume). 308 mg (74%) of trans-diiodo(N-cyclohexylamine)[1,3-dimethylbenzimidazol-2-ylidene]platinum(II) are thus obtained in the form of yellow crystals whose characteristics are the following:

Rf=0.26 (silica gel; mixture of 80% of cyclohexane and 20% of ethyl acetate)

$^1$H NMR spectrum (CDCl$_3$, 20° C.), δ [ppm]: 1.02-1.33 (m, 5H), 1.56 (m, 1H), 1.71 (m, 2H), 2.22 (m, 2H), 3.10 (m, 1H), 3.82-3.94 (m, 2H), 4.00 (s, 6H), 7.31 (m, 2H), 7.62 (m, 2H).

EXAMPLE 9 trans-diiodo(N-cyclohexylamine)(1,3,7,9-tetramethylxanthin-8-ylidene)platinum(II)

Step 1: [1,3,7,9-tetramethylxanthin-8-ylidene(1,3-divinyl-1,1,3,3-tetramethyldi-siloxane)]platinum(0)

To a solution of bis(1,3,7,9-tetramethylxanthin-8-ylidene) silver(I) methyl carbonate—which was obtained according to J. Youngs et al., Journal of Medicinal Chemistry (2006), 49, 6811-6818—(4.1 g, 6.8 mmol) in 240 ml of dimethylformamide, there is added a 0.1 M solution of platinum(0) 1,3-divinyl-1,1,3,3-tetramethyldisiloxane in xylene (136 ml; 13.6 mmol). The reaction mixture is stirred for 16 h at room temperature and then evaporated to dryness. The residue obtained is filtered on Clarcel and is then purified by flash chromatography by elution with a gradient of mixtures of heptane and ethyl acetate (70/30 to 50/50 by volume), 4.2 g (52%) of [1,3,7,9-tetramethylxanthin-8-ylidene(1,3-divinyl-1,1,3,3-tetramethyldisiloxane)]platinum(0) are thus recovered whose characteristics are the following:
$^1$H NMR spectrum (300 MHz, CDCl$_3$, 20° C.) δ [ppm]=–0.27 (s, 6H), 0.33 (s, 6H), 1.96 (m, 4H), 2.2-2.4 (m, 2H), 3.42 (s, 3H), 3.82 (s, 3H), 3.83 (s, 3H), 3.96 (s, 3H).

Step 2: trans-diiodo(N-cyclohexylamine)(1,3,7,9-tetramethylxanthin-8-ylidene)platinum(II)

Figure 3:
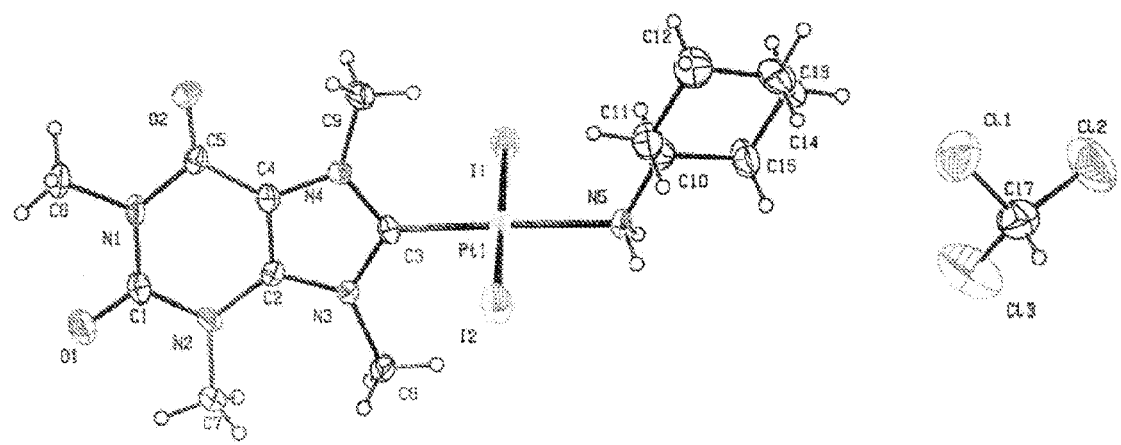
FIG. 3: Depicts an ORTEP diagram representing the structure of the compound of Example 9, described herein.

To a solution of the complex [1,3,7,9-tetramethylxanthin-8-ylidene(1,3-divinyl-1,1,3,3-tetramethyldisiloxane)]platinum(0) (0.13 g; 0.22 mmol) in 11 ml of toluene at 0° C., there is added a solution of diiodine (0.06 g; 0.24 mmol) in 19 ml of toluene. Next, 27 µl of cyclohexylamine (0.24 mmol) are added to the mixture. The reaction mixture is stirred for 16 h at room temperature and then evaporated to dryness. The residue obtained is purified by flash chromatography by elution with a mixture of heptane and ethyl acetate (70/30 by volume), 0.07 g (39%) of trans-diiodo(N-cyclohexylamine)(1,3,7,9-tetramethylxanthin-8-ylidene)platinum(II) is thus recovered in the form of yellow crystals whose characteristics are the following:
$^1$H NMR spectrum (500 MHz, CDCl$_3$, 20° C.) δ [ppm]= 1.1-1.4 (5H), 1.65 (m, 1H), 1.79 (m, 2H), 2.27 (m, 2H), 3.0 (br, 2H), 3.26 (m, 1H), 3.38 (s, 3H), 3.78 (s, 3H), 4.21 (s, 3H), 4.32 (s, 3H).
Mass spectrum HRMS (ESI positive mode) calculated for C$_{15}$H$_{25}$I$_2$N$_5$O$_2$Pt.Na: 778.9643; found for C$_{15}$H$_{25}$I$_2$N$_5$O$_2$NaPt: 778.9643.
ORTEP diagram—X-ray diffraction. Crystals obtained from a solution of the complex in chloroform, by slow evaporation of the solvent. (See FIG. 3.)

EXAMPLE 10 trans-diiodo(N-cyclohexylamine)[1-methyl-3-(4-methoxybenzyl)-imidazol-2-ylidene]platinum(II)

Step 1: 3-(4-methoxybenzyl)-1-methylimidazolium bromide

Into a 50 ml one-necked flask surmounted by a condenser, there are successively introduced 1 ml (12.5 mmol) of N-methylimidazole, and then 5 g (18.8 mmol) of 4-methoxybenzyl bromide in solution in 25 ml of toluene. The reaction medium is heated under reflux, with stirring, for 2 h 30 min. After cooling to room temperature, the viscous oil formed is separated by decantation and then dried under vacuum at room temperature, 4.65 g of a pale yellow solid are thus obtained whose characteristics are the following:
$^1$H NMR spectrum (DMSO): δ 9.3 ppm (s, 1H), 7.82 (t, 1H), 7.74 (t, 1H), 7.43 (d, 2H), 6.98 (d, 2H), 5.38 (s, 2H), 3.87 (s, 3H), 3.77 (s, 3H).

Step 2: [1-methyl-3-(4-methoxybenzyl)imidazo-2-ylidene](1,3-divinyl-1,1,3,3-tetramethyldisiloxane)platinum(0)

Into a 50 ml one-necked flask under argon, there are successively introduced 0.354 g (1.25 mmol) of the compound obtained in Step 1 and 12.5 ml (1.25 mmol) of a 0.1 M solution of (1,3-divinyl-1,1,3,3-tetramethyldisiloxane)platinum(0) in xylene. The mixture is cooled to 0° C. and then 1.75 ml (1.75 mmol) of a 1 M solution of potassium tert-butoxide in tetrahydrofuran are added dropwise. The reaction medium is stirred at room temperature overnight. The reaction medium is evaporated to dryness. The residue thus obtained is purified by flash chromatography, eluting with a mixture of cyclohexane and ethyl acetate (97/3 by volume). 0.47 g (64%) of [1-methyl-3-(4-methoxybenzyl)imidazol-2-ylidene](1,3-divinyl-1,1,3,3-tetramethyldisiloxane)platinum(0) is thus obtained in the form of a slightly yellow foam whose characteristics are the following:
$^1$H NMR spectrum (DMSO): δ 7.44 (t, 2H), 7.65 (d, 2H), 7.10 (d, 2H), 5.02 (m, 2H), 3.72 (s, 3H), 3.47 (s, 3H), 2.33-1.62 (m, 6H), 0.22 (m, 6H), –0.30 (m, 6H).

Step 3: trans-diiodo(N-cyclohexylamine)[1-methyl-3-(4-methoxybenzyl)imidazol-2-ylidene]platinum(II)

In a 100 ml three-necked flask under argon, there is dissolved 0.230 g (0.394 mmol) of the compound obtained in Step 2 in 30 ml of toluene and then the mixture is cooled to 0° C. There is then successively added dropwise at 0° C., a solution of 0.1 g (0.394 mmol) of diiodine in 10 ml of toluene and then 45.1 µl (0.394 mmol) of cyclohexylamine. The reaction medium is then stirred at room temperature for 4 h. The reaction medium is evaporated to dryness. The residue thus obtained is purified by flash chromatography, eluting with a mixture of cyclohexane and ethyl acetate (80/20 by volume). 51 mg (17%) of trans-diiodo(N-cyclohexylamine)[1-methyl-3-(4-methoxybenzyl)imidazol-2-ylidene]platinum(II) are thus obtained in the form of a yellow powder whose characteristics are the following:
$^1$H NMR spectrum (CDCl$_3$): δ 7.45 (d, 2H), 6.95 (d, 2H), 6.82 (d, 1H), 6.60 (d, 1H), 5.58 (s, 2H), 3.95 (s, 3H), 3.87 (s, 3H), 3.30 (m, 1H), 3.00 (d, 2H), 2.14 (d, 2H), 1.53 (d, 2H), 1.38 (d, 1H), 1.10 (q, 2H), 0.98 (q, 2H), 0.89 (d, 1H)

EXAMPLE 11 trans-diiodo(N-cyclohexylamine)[1-methyl-3-(4-trifluoromethylbenzyl)imidazol-2-ylidene]platinum (II)

Step 1: 1-(4-trifluoromethylbenzyl)-3-methylimidazolium bromide

By carrying out the procedure as in Step 1 of Example 10, but starting with 2 g of N-methylimidazole and 8.73 g of 4-trifluoromethylbenzyl bromide, at the reflux temperature of toluene for 2 hours, 8.4 g of 1-(4-trifluoromethylbenzyl)-3-methylimidazolium bromide are obtained in the form of an orange-yellow solid whose characteristics are the following:
$^1$H NMR spectrum (DMSO): δ 9.33 ppm (s, 1H), 7.88 (t, 1H), 7.78 (t, 1H), 7.80 (d, 2H), 7.68 (d, 2H), 5.60 (s, 2H), 3.90 (s, 3H)

Step 2: [1-methyl-3-(4-trifluoromethylbenzyl)imidazol-2-ylidene](1,3-divinyl-1,1,3,3-tetramethyldisiloxane)platinum(0)

By carrying out the procedure as in Step 2 of Example 10, but starting with 0.401 g of the compound obtained in Step 1 and 12.5 ml (1.25 mmol) of a 0.1 M solution of (1,3-divinyl-1,1,3,3-tetramethyldisiloxane)platinum(0) in xylene and 1.75 ml (1.75 mmol) of a 1 M solution of potassium tert-butoxide in tetrahydrofuran, there is obtained, after purification by flash chromatography, eluting with a mixture of cyclohexane and ethyl acetate (97/3 by volume), 0.4 g (58%) of [1-methyl-3-(4-trifluoromethylbenzyl)imidazol-2-ylidene](1,3-divinyl-1,1,3,3-tetramethyldisiloxane)platinum(0) in the form of a pale yellow foam whose characteristics are the following:

$^1$H NMR spectrum (DMSO): δ 7.70 (d, 2H), 7.50 (m, 2H), 7.25 (m, 2H), 5.25 (m, 2H), 3.50 (s, 3H), 2.30-1.60 (m, 6H), 0.20 (m, 6H), −0.35 (m, 6H).

Step 3: trans-diiodo(N-cyclohexylamine)[1-methyl-3-(4-trifluoromethylbenzyl) imidazol-2-ylidene]platinum(II)

By carrying out the procedure as in Step 3 of Example 11, but starting with 0.230 g of the compound obtained in Step 2, in 30 ml of toluene, 0.094 g (0.394 mmol) of diiodine in 10 ml of toluene and 42.4 µl (0.394 mmol) of cyclohexylamine, at room temperature for 4 h, there are obtained, after purification by flash chromatography, eluting with a mixture of cyclohexane and ethyl acetate (85/15 by volume), 40 mg (14%) of trans-diiodo(N-cyclohexylamine)[1-methyl-3-(4-trifluoromethylbenzyl)imidazol-2-ylidene]platinum(II) in the form of a yellow powder whose characteristics are the following:

$^1$H NMR spectrum (CDCl$_3$): δ 7.69 (d, 2H), 7.62 (d, 2H), 6.88 (d, 1H), 6.65 (d, 1H), 5.73 (s, 2H), 3.98 (s, 3H), 3.30 (m, 1H), 2.98 (d, 2H), 2.32 (d, 2H), 1.82 (d, 2H), 1.78 (d, 1H), 1.38 (q, 2H), 1.26 (q, 2H), 1.18 (d, 1H).

EXAMPLE 12 trans-diiodo(N-cyclohexylamine)[1,3-dibenzylimidazol-2-ylidene]-platinum(II)

Step 1: [1,3-dibenzylimidazol-2-ylidene](1,3-divinyl-1,1,3,3-tetramethyldisiloxane)platinum(0)

By carrying out the procedure as in Step 2 of Example 10, but starting with 0.433 g (1.25 mmol) of 1,3-dibenzylimidazolium bromide—which was obtained according to E Diaz-Barra et al., Organometallics (2007), 26(24), 5782-85—12.5 ml (1.25 mmol) of a 0.1 M solution of (1,3-divinyl-1,1,3,3-tetramethyldisiloxane)platinum(0) in xylene and 1.75 ml (1.75 mmol) of a 1 M solution of potassium tert-butoxide in tetrahydrofuran, there is obtained, after purification by flash chromatography, eluting with a mixture of cyclohexane and ethyl acetate (98/2 by volume), 0.72 g (86%) of [1,3-dibenzylimidazol-2-ylidene](1,3-divinyl-1,1,3,3-tetramethyldisiloxane)platinum(0) in the form of a pale yellow foam whose characteristics are the following:

Rf=0.42 (silica gel, mixture of 60% of cyclohexane and 40% of ethyl acetate).

$^1$H NMR spectrum (DMSO): δ 7.55 (m, 1H), 7.40 (m, 1H), 7.58-7.20 (m, 10H), 4.98 (d, 4H), 2.20-1.55 (m, 6H), 0.20 (s, 6H), −0.50 (s, 6H).

Step 2: trans-diiodo(N-cyclohexylamine)[1,3-dibenzylimidazol-2-ylidene]platinum(II)

By carrying out the procedure as in Step 3 of Example 11, but starting with 0.325 g (0.516 mmol) of the compound obtained in Step 1, in 45 ml of toluene, 0.131 g (0.516 mmol) of diiodine in 10 ml of toluene and 51.2 µl (0.516 mmol) of cyclohexylamine, at room temperature for 7 h, there are obtained, after purification by flash chromatography, eluting with a gradient of mixtures of cyclohexane and ethyl acetate (from 97/3 to 95/5 by volume), and then crystallization from 5 ml of diisopropyl ether, 90 mg (22%) of trans-diiodo(N-cyclohexylamine)[1,3-dibenzylimidazol-2-ylidene]platinum(II) in the form of an orange powder whose characteristics are the following:

Rf=0.14 (silica gel, mixture of 95% of cyclohexane and 5% of ethyl acetate)

$^1$H NMR spectrum (CDCl$_3$): δ 7.48 (d, 4H), 7.38 (m, 6H), 6.53 (s, 2H), 5.62 (s, 4H), 3.28 (m, 1H), 2.98 (m, 2H), 2.28 (d, 2H), 1.75 (d, 2H), 1.62 (d, 1H), 1.32 (q, 2H), 1.20 (q, 2H), 1.12 (d, 1H)

EXAMPLE 13 trans-diiodo(N-benzylamine)(1,3-dimethylimidazol-2-ylidene)-platinum(II)

In a 100 ml three-necked flask under argon, there is dissolved 0.2 g (0.42 mmol) of (1,3-dimethylimidazol-2-ylidene)(1,3-divinyl-1,1,3,3-tetramethyldisiloxane)platinum (0)—which was obtained according to G Berthon-Gelloz et al., Journal of Organometallic Chemistry (2005), 690(24-25), 6156-68—in 40 ml of toluene and then the mixture is cooled to 0° C. There is then successively added dropwise at 0° C. a solution of 0.106 g (0.42 mmol) of diiodine in 10 ml of toluene and then 45.8 µl (0.42 mmol) of benzylamine. The reaction medium is then stirred at room temperature for 5 h. The reaction medium is evaporated to dryness. The residue thus obtained is purified by flash chromatography, eluting with a gradient of mixtures of cyclohexane and ethyl acetate (from 95/5 to 75/25 by volume). After crystallization from 1 ml of diisopropyl ether, 60 mg (22%) of trans-diiodo(N-benzylamine)(1,3-dimethylimidazol-2-ylidene)platinum(II) are obtained in the form of a yellow powder whose characteristics are the following:

Rf=0.11 (silica gel; mixture of 90% of cyclohexane and 10% of ethyl acetate)

$^1$H NMR spectrum (CDCl$_3$, 20°), [δ ppm]: 3.24 (broad m, 2H), 3.87 (s, 6H), 4.12 (m, 2H), 6.81 (s, 2H), 7.30-7.43 (m, 5H).

EXAMPLE 14 trans-diiodo[N-4-(trifluoromethyl)benzylamine](1,3-dimethylimidazol-2-ylidene)platinum(II)

By carrying out the procedure as in Example 13, but starting with 0.2 g (0.42 mmol) of (1,3-dimethylimidazol-2-ylidene)(1,3-divinyl-1,1,3,3-tetramethyldisiloxane)platinum (0)—which was obtained according to G Berthon-Gelloz et al., Journal of Organometallic Chemistry (2005), 690(24-25), 6156-68—a solution of 0.106 g (0.42 mmol) of diiodine in 10 ml of toluene and 59.7 µl (0.42 mmol) of 4-(trifluoromethyl) benzylamine in 40 ml of toluene, for 6 h. After purification by flash chromatography, eluting with a gradient of mixtures of cyclohexane and ethyl acetate (from 95/5 to 90/10 by volume), and then crystallization from 2 ml of diisopropyl ether, 201 mg (67%) of trans-diiodo[N-4-(trifluoromethyl)benzylamine](1,3-dimethylimidazol-2-ylidene)platinum(II) are thus obtained in the form of yellow crystals whose characteristics are the following:

Rf=0.14 (silica gel; mixture of 90% of cyclohexane and 10% of ethyl acetate)

$^1$H NMR spectrum (CDCl$_3$, 20°), [δ ppm]: 2.9 (m, 2H), 3.85 (s, 6H), 4.23 (m, 2H), 6.81 (s, 2H), 7.53 (d, J=8.1 Hz, 2H), 7.66 (d, J=8.1 Hz, 2H).

EXAMPLE 15 trans-diiodo(N-cyclohexylamine)[1-methyl-3-vinylimidazol-2-ylidene]platinum(II)

Step 1: [1-methyl-3-vinylimidazol-2-ylidene](1,3-divinyl-1,1,3,3-tetramethyldi-siloxane)platinum(0)

By carrying out the procedure as in Step 2 of Example 10, but starting with 0.226 g (1.55 mmol) of 1-methyl-3-(2-chloroethyl)imidazolium chloride—which was obtained according to S. Letaief et al., Journal of Materials Chemistry (2007), 17(15), 1476-84—12.5 ml (1.25 mmol) of a 0.1 M solution of (1,3-divinyl-1,1,3,3-tetramethyldisiloxane)platinum(0) in xylene and 2.5 ml (2.5 mmol) of a 1 M solution of potassium tert-butoxide in tetrahydrofuran, for 8 h. There is obtained, after purification by flash chromatography, eluting with a mixture of cyclohexane and ethyl acetate (97/3 by volume), 0.414 g (54%) of (1-methyl-3-vinylimidazol-2-ylidene)(1,3-divinyl-1,1,3,3-tetramethyldisiloxane)platinum(0) in the form of a pale yellow foam whose characteristics are the following:
Rf=0.15 (silica gel, mixture of 95% de cyclohexane and 5% of ethyl acetate).

Step 2: trans-diiodo(N-cyclohexylamine)(1-methyl-3-vinylimidazol-2-ylidene)-platinum(II)

By carrying out the procedure as in Step 3 of Example 11, but starting with 0.236 g (0.48 mmol) of the compound obtained in Step 1, in 45 ml of toluene, 0.122 g (0.48 mmol) of diiodine in 10 ml of toluene and 55 µl (0.47 mmol) of cyclohexylamine, at room temperature for 6 h, there are obtained, after purification by flash chromatography, eluting with a mixture of cyclohexane and ethyl acetate (85/15 by volume), and then crystallization from 2 ml of diisopropyl ether, 161 mg (51%) of trans-diiodo(N-cyclohexylamine)(1-methyl-3-vinylimidazol-2-ylidene)platinum(II) in the form of an orange powder whose characteristics are the following:
Rf=0.13 (silica gel, mixture of 85% of cyclohexane and 15% of ethyl acetate)
$^1$H NMR spectrum (CDCl$_3$, 20°), [δ ppm]: 1.08-1.43 (m, 5H), 1.66 (m, 1H), 1.80 (m, 2H), 2.29 (m, 2H), 2.96 (broad m, 2H), 3.27 (m, 1H), 3.91 (s, 3H), 5.04 (dd, J=8.9, 2.1 Hz, 1H), 5.24 (dd, J=15.9, 2.1 Hz, 1H), 6.87 (d, J=2.4 Hz, 1H), 7.15 (d, J=2.4 Hz, 1H), 7.93 (dd, J=15.9, 8.9 Hz, 1H).

EXAMPLES 16 AND 17 trans-diiodo(N-exo(+)bicyclo[2.2.1]heptylamine)(1,3-di-methylbenzimidazol-2-ylidene)platinum(II) and trans-diiodo(N-exo(−)bicyclo[2.2.1]heptylamine)(1,3-dimethylbenzimidazol-2-ylidene)platinum(II)

77 mg of trans-diiodo(N-exo(+/−)bicyclo[2.2.1]heptylamine)(1,3-dimethyl-benzimidazol-2-ylidene)platinum(II), obtained as in Example 7, are separated by chiral HPLC on a column 350 mm long and 50 mm in diameter filled with silica Chiracel OJ FB001 20 µM, eluting with a mixture of n-heptane, isopropanol and methanol (80/10/10 by volume) at a flow rate of 90 ml/min. The separation is monitored by UV detection at 254 nM.

By recovering the first eluted fraction, there are obtained, after concentrating to dryness under reduced pressure, 37.1 mg of trans-diiodo(N-exo(−)bicyclo[2.2.1]heptylamine)(1,3-dimethylbenzimidazol-2-ylidene)platinum(II) in the form of a yellow powder whose characteristics are the following:
Optical rotation α$_D^{20}$=−4+/−0.2° (c=0.916, DMSO)
Retention time=11.8 min (Chiracel OJ 20 µM; 250×4.6 mm; heptane/methanol/isopropanol 70/15/15 at a flow rate of 1 ml/min).

Upon recovering the second eluted fraction, after concentrating to dryness under reduced pressure, 32.6 mg of trans-diiodo(N-exo(+)bicyclo[2.2.1]heptylamine)(1,3-dimethyl-benzimidazol-2-ylidene)platinum(II) are obtained in the form of a yellow powder whose characteristics are the following:
Optical rotation α$_D^{20}$=+4.2+/−0.2° (c=0.931, DMSO)
Retention time=13.6 min (Chiracel OJ 20 µM; 250×4.6 mm; heptane/methanol/isopropanol 70/15/15 at a flow rate of 1 ml/min).

EXAMPLE 18 trans-diiodo(N-cyclohexylamine)(1,3-dicyclohexylimidazol-2-ylidene)platinum(II)

To a solution of the complex (1,3-dicyclohexylimidazol-2-ylidene)(1,3-divinyl-1,1,3,3-tetramethyldisiloxane)]platinum(0) (0.2 g; 0.32 mmol)—which was obtained according to I. E. Marko et al., *Advanced Synthesis and Catalysis* (2004), 346(12), 1429-34—in 15 ml of toluene at 0° C., there is added a solution of diiodine (0.09 g; 0.35 mmol) in 30 ml of toluene. Next, 40 µl of cyclohexylamine (0.35 mmol) are added to the mixture. The reaction mixture is stirred for 16 h at room temperature and then evaporated to dryness. The residue obtained is chromatographed on silica by elution with a mixture of heptane and ethyl acetate (80/20 by volume). The fractions containing the expected product are rechromatographed on a silica column, eluting with a mixture of heptane and toluene (40/60 by volume), 0.12 g is thus recovered which is recrystallized from a mixture of dichloromethane and heptane to give 0.1 g (40%) of trans-diiodo(N-cyclohexylamine)(1,3-dicyclohexylimidazol-2-ylidene)platinum(II) in the form of beige-yellow crystals whose characteristics are the following:
$^1$H NMR spectrum (500 MHz, CDCl$_3$, 20° C.) δ [ppm]= 1.1-1.5 (15H), 1.63 (m, 1H), 1.7-1.8 (4H), 1.88 (m, 4H), 2.31 (m, 6H), 2.92 (br, 2H), 3.28 (m, 1H), 5.20 (m, 2H), 6.82 (s, 2H).
HRMS mass spectrum (ESI positive mode) calculated for C$_{21}$H$_{37}$I$_2$N$_3$Pt.Na: 803.0622; found for C$_{21}$H$_{37}$I$_2$N$_3$NaPt: 803.0658.

EXAMPLE 19 trans-diiodo(N-cyclohexylamine)(1-methyl-3-phenyl-1,2,4-triazol-5-ylidene)platinum(II)

Step 1: 1-phenyl-4-methyl-1,2,4-triazolium iodide

Methyl iodide (0.13 ml; 2 mmol) is added to a solution of 1-phenyl-1,2,4-triazole—which was obtained according to Antilla, J. C. et al., Journal of Organic Chemistry 2004, 69, 5578-5587—(0.15 g; 1 mmol) in 1 ml of acetonitrile. This mixture is heated at 80° C. for 16 hours, and is then evaporated to dryness. The residue obtained is recrystallized from a minimum amount of ethyl acetate, thus making it possible to obtain 0.12 g of the desired product (41%) whose characteristics are the following:

¹H NMR spectrum (500.19 MHz, CDCl₃, 20° C.) δ [ppm]=4.34 (s, 3H), 7.54 (m, 3H), 7.96 (d, 2H), 9.09 (s, 1H), 11.60 (s, 1H).

Step 2: [1-phenyl-4-methyl-1,2,4-triazol-5-ylidene(1,3-divinyl-1,1,3,3-tetramethyldisiloxane)]platinum(0)

To a solution of 1-phenyl-4-methyl-1,2,4-triazolium iodide (0.12 g; 0.42 mmol) in 20 ml of dichloromethane, there is added, at 0° C., 0.1 M (1,3-divinyl-1,1,3,3-tetramethyldisiloxane)platinum(0) in xylene (4.2 ml; 0.42 mmol) and potassium tert-butoxide (0.07 g; 0.63 mmol). The reaction mixture is stirred for 16 h at room temperature and then evaporated to dryness. The residue obtained is purified by flash chromatography, eluting with a mixture of heptane and ethyl acetate (80/20 by volume), 0.07 g of the desired product (31%) is thus recovered whose characteristics are the following:

¹H NMR spectrum (300 MHz, CDCl₃, 20° C.) δ [ppm]=−0.34 (s, 6H), 0.31 (s, 6H), 1.8-2.1 (m, 4H), 2.25 (d, 2H), 3.65 (s, 3H), 7.3 (m, 3H), 7.92-7.96 (m, 2H), 8.19 (s, 1H).

Step 3: trans-diiodo(N-cyclohexylamine)(1-phenyl-4-methyl-1,2,4-triazol-5-ylidene)platinum(II)

To a solution of the complex [1-phenyl-4-methyl-1,2,4-triazol-5-ylidene(1,3-divinyl-1,1,3,3-tetramethyldisiloxane)]platinum(0) (0.07 g; 0.13 mmol) in 6 ml of toluene at 0° C., there is added a solution of I₂ (0.04 g; 0.14 mmol) in 12 ml of toluene. Next, 22 μl of cyclohexylamine (0.19 mmol) are added to the mixture. The reaction mixture is stirred for 16 h at room temperature and then evaporated to dryness. The residue obtained is purified by flash chromatography by elution with a mixture of heptane and ethyl acetate (85/15 by volume). 0.02 g of the desired product (22%) is thus recovered whose characteristics are the following:

¹H NMR spectrum (500 MHz, CDCl₃, 20° C.) δ [ppm]= 1.1-1.5 (5H), 1.62 (m, 1H), 1.74 (m, 2H), 2.19 (m, 2H), 2.97 (br, 2H), 3.17 (m, 1H), 3.99 (s, 6H, CH₃N), 7.3-7.5 (3H), 8.03 (s, 1H), 8.19 (m, 2H).

HRMS mass spectrum (ESI positive mode) calculated for C₁₅H₂₂I₂N₄Pt.Na: 729.9479; found for C₁₅H₂₂I₂N₄NaPt: 729.9509.

EXAMPLE 20 trans-diiodo(N-cyclohexylamine)[1,3-dimethyl-4-phenylimidazol-2-ylidene]platinum(II)

Step 1: [1,3-dimethyl-4-phenylimidazol-2-ylidene](1,3-divinyl-1,1,3,3-tetramethyldisiloxane)platinum(0)

By carrying out the procedure as in Step 2 of Example 10, but starting with 0.375 g (1.25 mmol) of 1,3-dimethyl-4-phenylimidazolium iodide—which was obtained according to M. R. Grimmett, Science of Synthesis (2002), 12, 325-528—12.5 ml (1.25 mmol) of a 0.1 M solution of (1,3-divinyl-1,1,3,3-tetramethyldisiloxane)platinum(0) in xylene and 1.75 ml (1.75 mmol) of a 1 M solution of potassium tert-butoxide in tetrahydrofuran, there is obtained, after purification by flash chromatography, eluting with a mixture of cyclohexane and ethyl acetate (98/2 by volume), 0.595 g (86%) of [1,3-dimethyl-4-phenylimidazol-2-ylidene](1,3-divinyl-1,1,3,3-tetramethyldisiloxane)platinum(0), in the form of a white solid, whose characteristics are the following:

Rf=0.28 (silica gel, mixture of 90% of cyclohexane and 10% of ethyl acetate).

¹H NMR spectrum (DMSO): δ 7.60-7.40 (m, 6H), 3.50 (s, 6H), 2.20 (m, 2H), 1.90 (m, 2H), 1.70 (m, 2H), 0.25 (s, 6H), −0.30 (s, 6H).

Step 2: trans-diiodo(N-cyclohexylamine)[1,3-dimethyl-4-phenylimidazol-2-ylidene]platinum(II)

By carrying out the procedure as in Step 3 of Example 11, but starting with 0.3 g (0.542 mmol) of the compound obtained in Step 1, in 40 ml of toluene, 0.138 g (0.542 mmol) of diiodine in 10 ml of toluene and 62 μl (0.5426 mmol) of cyclohexylamine, at room temperature for 7 h, there are obtained, after purification by flash chromatography, eluting with a mixture of cyclohexane and ethyl acetate (90/10 by volume), and then crystallization from 2 ml of diisopropyl ether, 275 mg (70%) of trans-diiodo(N-cyclohexylamine)[1,3-dimethyl-4-phenylimidazol-2-ylidene]platinum(II) in the form of yellow crystals whose characteristics are the following:

Rf=0.18 g of silica gel, mixture of 90% of cyclohexane and 10% of ethyl acetate.

¹H NMR spectrum (CDCl₃): δ 7.48 (m, 3H), 7.38 (m, 2H), 6.85 (s, 1H), 5.30 (dd, 1H), 3.98 (s, 3H), 3.90 (s, 3H), 3.33 (m, 1H), 2.98 (m, 2H), 2.85 (d, 2H), 1.85 (d, 2H), 1.70 (d, 1H), 1.40 (q, 2H), 1.28 (q, 2H), 1.18 (d, 1H)

EXAMPLE 21 trans-diiodo(N-cyclohexylamine)[3-benzyl-1-methyl-4-phenylimidazol-2-ylidene]platinum(II)

Step 1

In a 25 ml one-necked flask, there is dissolved 0.320 g (2.023 mmol) of 1-methyl-4-phenylimidazole, which was obtained according to P. Benjes et al., Heterocycles (1994), 37(2), 735-38, in 10 ml of toluene and then 0.36 ml (3.035 mmol) of benzyl bromide is added. After 5 days of heating under reflux, the reaction medium is concentrated under reduced pressure. The residue is taken up in 50 ml of diisopropyl ether. The precipitate formed is drained, washed twice with 5 ml of diisopropyl ether, and then dried under reduced pressure. 0.500 g (90%) of 3-benzyl-1-methyl-4-phenylimidazolium bromide is thus obtained in the form of a beige-grey solid whose characteristics are the following:

¹H NMR spectrum (DMSO): δ 9.32 (s, 1H), 7.97 (d, 1H), 7.50 (m, 5H), 7.30 (m, 3H), 7.08 (m, 2H), 5.48 (s, 2H), 3.93 (s, 3H)

Step 2: [3-benzyl-1-methyl-4-phenylimidazol-2-ylidene](1,3-divinyl-1,1,3,3-tetramethyldisiloxane)platinum(0)

By carrying out the procedure as in Step 2 of Example 10, but starting with 0.439 g (1.33 mmol) of 3-benzyl-1-methyl-4-phenylimidazolium bromide, obtained in Step 1, 13.3 ml (1.33 mmol) of a 0.1 M solution of (1,3-divinyl-1,1,3,3-tetramethyldisiloxane)platinum(0) in xylene and 1.87 ml (1.87 mmol) of a 1 M solution of potassium tert-butoxide in tetrahydrofuran, there is obtained, after purification by flash chromatography, eluting with a mixture of cyclohexane and ethyl acetate (98/2 by volume), 0.485 g (70%) of [3-benzyl-1-methyl-4-phenylimidazol-2-ylidene](1,3-divinyl-1,1,3,3-tetramethyldisiloxane)platinum(0) in the form of a white solid whose characteristics are the following:

Rf=0.43 (silica gel, mixture of 90% of cyclohexane and 10% of ethyl acetate).
$^1$H NMR spectrum (DMSO): 7.63 (t, 1H), 7.35 (m, 5H), 7.15 (m, 3H), 6.80 (m, 2H), 5.35 (m, 2H), 3.58 (s, 3H), 2.20-1.50 (m, 6H), 0.20 (m, 6H), −0.30 (m, 3H), −0.62 (m, 3H)

Step 3: trans-diiodo(N-cyclohexylamine)[3-benzyl-1-methyl-4-phenylimidazol-2-ylidene]platinum(II)

By carrying out the procedure as in Step 3 of Example 11, but starting with 0.3 g (0.476 mmol) of the compound obtained in step 2, in 40 ml of toluene, 0.141 g (0.556 mmol) of diiodine in 10 ml of toluene and 54.5 µl (0.476 mmol) of cyclohexylamine, at room temperature for 48 h, there are obtained, after purification by flash chromatography, eluting with a gradient of mixtures of cyclohexane and ethyl acetate (from 95/5 to 90/10 by volume), and then crystallization from 2 ml of diisopropyl ether, 83 mg (22%) of trans-diiodo(N-cyclohexylamine)[3-benzyl-1-methyl-4-phenylimidazol-2-ylidene]platinum(II) in the form of yellow crystals whose characteristics are the following:
Rf=0.21 (silica gel, mixture of 90% of cyclohexane and 10% of ethyl acetate).
$^1$H NMR spectrum (CDCl$_3$): δ 7.30 (m, 5H), 7.20 (m, 3H), 7.15 (m, 2H), 5.73 (s, 2H), 4.00 (s, 3H), 3.25 (m, 1H), 2.98 (m, 2H), 2.25 (d, 2H), 1.78 (d, 2H), 1.65 (d, 1H), 1.35 (q, 2H), 1.20 (m, 2H), 1.18 (d, 1H).

EXAMPLE 22 trans-diiodo(N-cyclohexylamine)[1,3-dimethyl-4,5-diphenylimidazol-2-ylidene]platinum(II)

Step 1

In a 25 ml one-necked flask, there is dissolved 0.240 g (1.024 mmol) of 1-methyl-4-phenylimidazole, which was obtained according to W. Collibee et al., Tetrahedron Letters (1985), 62(6), 1595-96, in 7 ml of toluene and then 100 µl of methyl iodide are added. After 15 days of heating under reflux while adding 100 µl of methyl iodide every day, the reaction medium is concentrated under reduced pressure. The residue is taken up in 50 ml of diisopropyl ether. The precipitate formed is drained, washed twice with 5 ml of diisopropyl ether, and then dried under reduced pressure. 0.370 g (98%) of 1,3-dimethyl-4,5-diphenylimidazolium iodide is thus obtained in the form of a pale yellow solid whose characteristics are the following:
$^1$H NMR spectrum (DMSO): δ 9.30 (s, 1H), 7.48 (m, 6H), 7.40 (m, 4H), 3.75 (s, 6H)

Step 2: [3-benzyl-1-methyl-4-phenylimidazol-2-ylidene](1,3-divinyl-1,1,3,3-tetramethyldisiloxane)platinum(0)

By carrying out the procedure as in Step 2 of Example 10, but starting with 0.210 g (0.53 mmol) of 1,3-dimethyl-4,5-diphenylimidazolium iodide, obtained in Step 1, 5.3 ml (0.53 mmol) of a 0.1 M solution of (1,3-divinyl-1,1,3,3-tetramethyldisiloxane)platinum(0) in xylene and 0.74 ml (0.74 mmol) of a 1 M solution of potassium tert-butoxide in tetrahydrofuran, there is obtained, after purification by flash chromatography, eluting with a mixture of cyclohexane and ethyl acetate (95/5 by volume), 0.191 g (57%) of [1,3-dimethyl-4,5-diphenylimidazol-2-ylidene](1,3-divinyl-1,1,3,3-tetramethyldisiloxane)platinum(0) in the form of a white solid whose characteristics are the following:
Rf=0.45 (silica gel, mixture of 90% of cyclohexane and 10% of ethyl acetate).
$^1$H NMR spectrum (DMSO): 7.38 (m, 10H), 3.42 (s, 6H), 2.28 (m, 2H), 1.97 (m, 2H), 1.75 (m, 2H), 0.25 (s, 6H), −0.30 (s, 6H)

Step 3: trans-diiodo(N-cyclohexylamine)[1,3-dimethyl-4,5-diphenylimidazol-2-ylidene]platinum(II)

By carrying out the procedure as in Step 3 of Example 11, but starting with 0.19 g (0.30 mmol) of the compound obtained in Step 2, in 40 ml of toluene, 0.077 g (0.30 mmol) of diiodine in 5 ml of toluene and 34.5 µl (0.30 mmol) of cyclohexylamine, at room temperature for 5 h, there are obtained, after purification by flash chromatography, eluting with a gradient of mixtures of cyclohexane and ethyl acetate (from 95/to 90/10 by volume), and then crystallization from 2 ml of diisopropyl ether, 76 mg (32%) of trans-diiodo(N-cyclohexylamine)[1,3-dimethyl-4,5-diphenylimidazol-2-ylidene]platinum(II) in the form of a yellow powder whose characteristics are the following:
Rf=0.24 (silica gel, mixture of 90% of cyclohexane and 10% of ethyl acetate).
$^1$H NMR spectrum (CDCl$_3$): δ 7.38 (m, 6H), 7.22 (m, 4H), 3.35 (s, 6H), 3.35 (m, 1H), 2.98 (m, 2H), 2.38 (d, 2H), 1.85 (d, 2H), 1.70 (d, 1H), 1.40 (q, 2H), 1.30 (q, 2H), 1.20 (d, 1H)

EXAMPLES 23 AND 24 trans-diiodo(N-exo(+)bicyclo[2.2.1]heptylamine)(1,3-di-methylimidazol-2-ylidene)platinum(II) and trans-diiodo(N-exo(−)bicyclo[2.2.1]heptyl-amine)(1,3-dimethylimidazol-2-ylidene)platinum(II)

75 mg of trans-diiodo(N-exo(+/−)bicyclo[2.2.1]heptylamine)(1,3-dimethylimidazol-2-ylidene)platinum(II), obtained as in Example 6, are separated by chiral HPLC, in 3 successive injections of 25 mg, on a column 250 mm long and 20 mm in diameter filled with silica Chiracel OJ FB001 10 µM, eluting with a mixture of n-heptane, isopropanol and methanol (80/10/10 by volume) at a flow rate of 25 ml/min. The separation is monitored by UV detection at 254 nM.

Upon recovering the first eluted fractions, there are obtained, after concentrating to dryness under reduced pressure, 22.4 mg of enantiomerically pure trans-diiodo(N-exo(−)bicyclo[2.2.1]heptylamine)(1,3-dimethylimidazol-2-ylidene)platinum(II) in the form of a yellow powder whose characteristics are the following:
Optical rotation $\alpha_D^{20}$=−3.6+/−0.5° (c=0.437, DMSO)
Retention time=19.1 min (Chiracel OJ 20 µM; 250×4.6 mm; heptane/methanol/isopropanol 80/10/10 at a flow rate of 1 ml/min).

Upon recovering the second eluted fractions, there are obtained, after concentrating to dryness under reduced pressure, 35.6 mg of trans-diiodo(N-exo(+)bicyclo[2.2.1]heptylamine)(1,3-dimethylimidazol-2-ylidene)platinum(II), at 98.7% enantiomeric purity, in the form of a yellow powder whose characteristics are the following:
Optical rotation $\alpha_D^{20}$=+4.6+/−0.5° (c=0.461, DMSO)
Retention time=20.9 min (Chiracel OJ 20 µM; 250×4.6 mm; heptane/methanol/isopropanol 80/10/10 at a flow rate of 1 ml/min).

EXAMPLE 25 trans-diiodo(N-exo(+/−)bicyclo[2.2.1]heptylamine)
(1,3,7,9-tetra-methylxanthin-8-ylidene)platinum (II)

To a solution of the complex [1,3,7,9-tetramethylxanthin-8-ylidene(1,3-divinyl-1,1,3,3-tetramethyldisiloxane)]platinum(0), obtained in Step 2 of Example 9, (0.06 g, 0.1 mmol) in 5 ml of toluene at 0° C., there is added a solution of $I_2$ (0.03 g, 0.1 mmol) in 8 ml of toluene. Next, 26 µL of exo-2-norbornanamine (for a total of 0.22 mmol, in two successive additions) are added to the mixture. The reaction mixture is stirred for 16 h at room temperature and then evaporated to dryness. The residue obtained is purified by flash chromatography by elution with a mixture of heptane and ethyl acetate (70/30 by volume). 0.022 g of the desired product (29%) is thus recovered whose characteristics are the following:

$^1$H NMR (300 MHz, CDCl$_3$, 20° C.) δ [ppm]=1.1-1.9 (8H), 2.35 (m, 1H), 2.42 (m, 1H), 3.0 (br, 2H), 3.38 (s, 3H), 3.5 (br, 1H), 3.78 (s, 3H), 4.20 (s, 3H), 4.32 (s, 3H).

HRMS (ESI negative mode) calculated for $C_{16}H_{25}I_2N_5O_2$Pt: 767.9745; found for $C_{16}H_{24}I_2N_5O_2$Pt: 766.9705.

EXAMPLE 26 trans-diiodo(N-cyclohexylamine)[3-benzyl-4,5-diphenyl-1-methyl-imidazol-2-ylidene]platinum(II)

Step 1: 3-benzyl-4,5-diphenyl-1-methylimidazolium bromide

In a 25 ml one-necked flask, there is dissolved 0.240 g (1.024 mmol) of 4,5-diphenyl-1-methylimidazole, which was obtained according to Zeitschrift fuer Naturforschung, B: Chemical Sciences (2003), 58(4), 305-310, in 10 ml of toluene and then 183 µl (1.536 mmol) of benzyl bromide are added. After 2 days of heating under reflux, the reaction medium is concentrated under reduced pressure. The residue is taken up in 50 ml of diisopropyl ether. The precipitate formed is drained, washed twice with 5 ml of diisopropyl ether and then dried under reduced pressure. There is thus obtained 0.480 g (100%) of 3-benzyl-4,5-diphenyl-1-methylimidazolium bromide, in the form of a yellow solid, used as it is in the next step, whose characteristic is the following:

Rf=0.18 (silica gel, mixture of 90% of dichloromethane and 10% of methanol).

Step 2: [3-benzyl-4,5-diphenyl-1-methylimidazol-2-ylidene](1,3-divinyl-1,1,3,3-tetramethyldisiloxane)platinum(0)

By carrying out the procedure as in Step 2 of Example 10, but starting with 0.3 g (0.74 mmol) of 3-benzyl-1-methyl-4,5-diphenylimidazolium bromide, obtained in Step 1, 7.4 ml (0.74 mmol) of a 0.1 M solution of (1,3-divinyl-1,1,3,3-tetramethyldisiloxane)platinum(0) in xylene and 1.04 ml (1.04 mmol) of a 1 M solution of potassium tert-butoxide in tetrahydrofuran, there is obtained, after purification by flash chromatography, eluting mixtures of cyclohexane and ethyl acetate (99/1 and then 98/2 by volume), 0.211 g (40%) of [3-benzyl-4,5-diphenyl-1-methylimidazol-2-ylidene](1,3-divinyl-1,1,3,3-tetramethyldisiloxane)platinum(0) in the form of a white solid whose characteristics are the following:

Rf=0.46 (silica gel, mixture of 90% of cyclohexane and 10% of ethyl acetate).

Step 3: trans-diiodo(N-cyclohexylamine)[3-benzyl-4,5-diphenyl-1-methylimidazol-2-ylidene]platinum(II)

By carrying out the procedure as in Step 3 of Example 11, but starting with 0.1 g (0.181 mmol) of the compound obtained in Step 2, in 20 ml of toluene, 91 mg (0.36 mmol) of diiodine in 5 ml of toluene and 20.8 µl (0.181 mmol) of cyclohexylamine, at room temperature for 24 h, there are obtained, after purification by flash chromatography, eluting with a gradient of mixtures of cyclohexane and ethyl acetate (from 95/5 to 90/10 by volume), and then crystallization from 2 ml of diisopropyl ether, 79 mg (50%) of trans-diiodo(N-cyclohexylamine)[3-benzyl-4,5-diphenyl-1-methylimidazol-2-ylidene]platinum(II), in the form of a yellow powder whose characteristics are the following:

Rf=0.23 (silica gel, mixture of 90% of cyclohexane and 10% of ethyl acetate).

$^1$H NMR spectrum (CDCl$_3$): δ ppm: 1.10-1.44 (m, 5H) 1.67 (dt, J=12.7, 3.3 Hz, 1H) 1.80 (dt, J=13.4, 3.5 Hz, 2H) 2.29 (d, J=12.1 Hz, 2H) 2.88-3.09 (m, 2H) 3.21-3.36 (m, 1H) 3.94 (s, 3H) 5.75 (s, 2H) 6.97 (d, J=7.0 Hz, 2H) 7.13-7.27 (m, 10H) 7.32-7.37 (m, 3H)

EXAMPLE 27 trans-diiodo[N-(1-methylpiperidin-4-ylamine)](1-methyl-3-benzyl-imidazol-2-ylidene)platinum(II)

To a solution of the complex [1-methyl-3-benzylimidazol-2-ylidene](1,3-divinyl-1,1,3,3-tetramethyldisiloxane)]platinum(0), obtained in Step 1 of Example 5, (0.296 g, 0.535 mmol) in 5 ml of tetrahydrofuran at 0° C., there is added a solution of diiodine (0.142 g, 0.562 mmol) in 5 ml of tetrahydrofuran. Next, a solution of 67.2 mg (0.589 mmol) of 4-amino-1-methylpiperidine in 10 ml of tetrahydrofuran is added to the mixture. The reaction mixture is stirred for 16 h at room temperature and then evaporated to dryness. The residue obtained is purified by crystallization from a mixture of pentane and diethyl ether (80/20 by volume), 0.187 g (48%) of trans-diiodo[N-(1-methylpiperidin-4-ylamine)](1-methyl-3-benzylimidazol-2-ylidene)platinum(II) is thus obtained in the form of fine yellow crystals whose characteristics are the following:

$^1$H NMR spectrum (400 MHz, CDCl$_3$) δ ppm: 1.39-1.61 (m, 2H) 1.98 (t, J=11.0 Hz, 2H) 2.11 (d, J=13.4 Hz, 2H) 2.17 (s, 3H) 2.61-2.99 (m, 4H) 3.18 (br. s., 1H) 3.74 (s, 3H) 5.44 (s, 2H) 6.42 (d, J=1.5 Hz, 1H) 6.63 (d, J=1.8 Hz, 1H) 7.15-7.28 (m, 3H) 7.25-7.35 (m, 2H).

EXAMPLE 28 trans-diiodo(N-pentan-3-ylamine)(1-methyl-3-benzylimidazol-2-ylidene)platinum(II)

To a solution of the complex [1-methyl-3-benzylimidazol-2-ylidene](1,3-divinyl-1,1,3,3-tetramethyldisiloxane)]platinum(0), obtained in Step 1 of Example 5, (0.2 g, 0.379 mmol) in 5 ml of tetrahydrofuran at 0° C., there is added a solution of diiodine (96.2 mg, 0.361 mmol) in 5 ml of tetrahydrofuran. Next, a solution of 46.3 µl (0.397 mmol) of 3-aminopentane in 2 ml of tetrahydrofuran is added to the mixture. The reaction mixture is stirred for 18 h at room temperature and then evaporated to dryness. The residue obtained is purified by crystallization from 40 ml of hexane, 0.187 g (48%) of trans-diiodo(N-pentan-3-ylamine)(1-methyl-3-benzylimidazol-2-ylidene)platinum(II) is thus obtained in the form of yellow crystals whose characteristics are the following:

$^1$H NMR spectrum (400 MHz, CDCl$_3$) δ ppm: 1.05 (t, J=7.5 Hz, 6H) 1.66-1.88 (m, 4H) 2.88-2.99 (m, 2H) 3.34-3.44 (m, 1H) 3.95 (s, 3H) 5.65 (s, 2H) 6.62 (d, J=2.0 Hz, 1H) 6.83 (d, J=2.2 Hz, 1H) 7.36-7.45 (m, 3H) 7.48-7.54 (m, 2H).

EXAMPLE 29 trans-diiodo(N-4-aminotetrahydropyran)(1-methyl-3-benzylimidazol-2-ylidene)platinum(II)

To a solution of the complex [1-methyl-3-benzylimidazol-2-ylidene](1,3-divinyl-1,1,3,3-tetramethyldisiloxane)]platinum(0), obtained in Step 1 of Example 5, (0.2 g, 0.361 mmol) in 5 ml of tetrahydrofuran at 0° C., there is added a solution of diiodine (96.2 mg, 0.379 mmol) in 5 ml of tetrahydrofuran. Next, a solution of 54.7 mg (0.397 mmol) of 4-aminotetrahydrohydropyran hydrochloride in 2 ml of tetrahydrofuran and 0.1 ml of diisopropylethylamine is added to the mixture. The reaction mixture is stirred for 18 h at room temperature and then evaporated to dryness. The residue obtained is purified by flash chromatography on silica gel, eluting with dichloromethane. 0.320 g (82%) of trans-diiodo(N-4-aminotetrahydropyran)(1-methyl-3-benzylimidazol-2-ylidene)platinum(II) is thus obtained in the form of a yellow powder whose characteristics are the following:
$^1$H NMR spectrum (400 MHz, CDCl$_3$) δ ppm: 1.54-1.72 (m, 2H) 2.20-2.35 (m, 2H) 2.94-3.20 (m, 2H) 3.37-3.64 (m, 3H) 3.94 (s, 3H) 3.97-4.09 (m, 2H) 5.63 (s, 2H) 6.62 (d, J=2.2 Hz, 1H) 6.84 (d, J=2.2 Hz, 1H) 7.35-7.46 (m, 3H) 7.45-7.52 (m, 2H).

EXAMPLE 30 trans-diiodo(N-cyclopentylamine)(1-methyl-3-benzylimidazol-2-ylidene)platinum(II)

To a solution of the complex [1-methyl-3-benzylimidazol-2-ylidene](1,3-divinyl-1,1,3,3-tetramethyldisiloxane)]platinum(0), obtained in Step 1 of Example 5, (0.2 g, 0.361 mmol) in 5 ml of tetrahydrofuran at 0° C., there is added a solution of diiodine (96.2 mg, 0.379 mmol) in 5 ml of tetrahydrofuran. Next, a solution of 39.2 µl (0.397 mmol) of cyclopentylamine in 2 ml of tetrahydrofuran is added to the mixture. The reaction mixture is stirred for 18 h at room temperature and then evaporated to dryness. The residue obtained is purified by flash chromatography on silica gel, eluting with a mixture of heptane and ethyl acetate (90/10 by volume). 82 mg (32%) of trans-diiodo(N-cyclopentylamine)(1-methyl-3-benzylimidazol-2-ylidene)platinum(II) are thus obtained in the form of a yellow powder whose characteristics are the following:
$^1$H NMR spectrum (400 MHz, CDCl$_3$) δ ppm: 1.62-1.87 (m, 6H) 2.05-2.20 (m, 2H) 2.92-3.18 (m, 2H) 3.84-3.99 (m, 4H) 5.65 (s, 2H) 6.62 (d, J=2.0 Hz, 1H) 6.83 (d, J=2.0 Hz, 1H) 7.35-7.46 (m, 3H) 7.51 (d, J=6.8 Hz, 2H).

EXAMPLE 31 trans-diiodo(N-morpholine)(1-methyl-3-benzylimidazol-2-ylidene)-platinum(II)

To a solution of the complex [1-methyl-3-benzylimidazol-2-ylidene](1,3-divinyl-1,1,3,3-tetramethyldisiloxane)]platinum(0), obtained in Step 1 of Example 5, (0.2 g, 0.361 mmol) in 5 ml of tetrahydrofuran at 0° C., there is added a solution of diiodine (96.2 mg, 0.379 mmol) in 5 ml of tetrahydrofuran. Next, a solution of 35.2 µl (0.397 mmol) of morpholine in 2 ml of tetrahydrofuran is added to the mixture. The reaction mixture is stirred for 18 h at room temperature and then evaporated to dryness. The residue obtained is purified by flash chromatography on silica gel, eluting with a gradient of mixtures of heptane and ethyl acetate (from 95/5 to 85/15 by volume). 15 mg (6%) of trans-diiodo(N-morpholine)(1-methyl-3-benzylimidazol-2-ylidene)platinum(II) are thus obtained in the form of a yellow powder whose characteristics are the following:
$^1$H NMR spectrum (400 MHz, CDCl$_3$) δ ppm: 2.97 (d, J=13.2 Hz, 2H) 3.29-3.43 (m, 1H) 3.55-3.74 (m, 4H) 3.88 (d, J=10.7 Hz, 2H) 3.92 (s, 3H) 5.62 (s, 2H) 6.62 (d, J=2.0 Hz, 1H) 6.83 (d, J=2.0 Hz, 1H) 7.36-7.47 (m, 3H) 7.46-7.52 (m, 2H).
LC/MS: Column ACQUITY BEH C18 1.7 µm of 2.1×50 mm, at 50° C.
  Solvents: A=water containing 0.1% of formic acid; B=acetonitrile containing 0.1% of formic acid.
  Gradient: from 5 to 50% of B in 0.8 min, and then from 50 to 100% of B in 0.4 min, and then 0.65 min at 100% of B, and then from 100 to 5% of B in 0.15 min
  Flow rate: 1 ml/min
  Retention time=1.09 min

EXAMPLE 32 trans-diiodo(N-cyclohexylamine)[3-(3-methoxybenzyl)-1-methyl-imidazol-2-ylidene]platinum(II)

Step 1: [3-(3-methoxybenzyl)-1-methylimidazol-2-ylidene](1,3-divinyl-1,1,3,3-tetramethyldisiloxane) platinum(0)

In a 100 ml three-necked flask, under an argon atmosphere, there is dissolved 0.564 g (1.99 mmol) of 3-(3-methoxybenzyl)-1-methylimidazolium bromide, which may be obtained according to J. Agr. Food Chem. (2007), 55(22), 9142-8, in 50 ml of dichloromethane, and then 0.231 g (0.996 mmol) of silver oxide is added. After stirring for 1 h at room temperature, 20.1 ml (2.01 mmol) of a 0.1 M solution of (1,3-divinyl-1,1,3,3-tetramethyldisiloxane)platinum(0) in xylene are added and then the mixture is stirred overnight at room temperature. After filtration on Celite of the insoluble silver salts, the reaction medium is concentrated to dryness under reduced pressure. The residue is crystallized overnight in a freezer at −20°, and then the crystals formed are drained, washed with pentane and dried under reduced pressure (20 mbar). 0.434 g (37%) of [3-(3-methoxybenzyl)-1-methylimidazol-2-ylidene](1,3-divinyl-1,1,3,3-tetramethyldisiloxane)platinum (0) is thus obtained in the form of white crystals whose characteristics are the following:
LC/MS: Column ACQUITY BEH C18 1.7 µm of 2.1×50 mm, at 50° C.
  Solvents: A=water containing 0.1% of formic acid; B=acetonitrile containing 0.1% of formic acid.
  Gradient: from 5 to 50% of B in 0.8 min, and then from 50 to 100% of B in 0.4 min, and then 0.65 min at 100% of B, and then from 100 to 5% of B in 0.15 min
  Flow rate: 1 ml/min
  Retention time=1.31 min Step 2: trans-diiodo(N-cyclohexylamine)[3-(3-methoxybenzyl)-1-methylimidazol-2-ylidene]platinum(II)

By carrying out the procedure as in Step 1 of Example 5, but starting with 0.2 g (0.342 mmol) of the compound obtained in Step 1, in 5 ml of tetrahydrofuran, 91.3 mg (0.36 mmol) of diiodine in 5 ml of tetrahydrofuran and 41.1 μl (0.374 mmol) of cyclohexylamine, at room temperature overnight, there are obtained, after purification by flash chromatography, eluting with a gradient of mixtures of cyclohexane and ethyl acetate (from 90/10 to 60/40 by volume), 100 mg (39%) of trans-diiodo(N-cyclohexylamine)[3-(3-methoxybenzyl)-1-methylimidazol-2-ylidene]platinum(II), in the form of a yellow powder, whose characteristics are the following:

$^1$H NMR spectrum (CDCl$_3$): δ ppm 1.10-1.47 (m, 5H) 1.69 (br.d, J=12.9 Hz, 1H), 1.82 (br.d, J=13.2 Hz, 2H), 2.34 (d, J=13.2 Hz, 2H), 2.86-3.09 (m, 2H) 3.25-3.37 (m, 1H) 3.85 (s, 3H) 3.95 (s, 3H) 5.62 (s, 2H) 6.65 (s, 1H) 6.84 (s, 1H) 6.93 (d, J=8.1 Hz, 1H) 7.06 (d, J=7.2 Hz, 1H) 7.11 (s, 1H) 7.32-7.36 (1H).

EXAMPLE 33 trans-diiodo(N-cyclohexylamine)[1-methyl-3-(3-trifluoromethylbenzyl)imidazol-2-ylidene]platinum (II)

Step 1: 1-methyl-3-(3-trifluoromethylbenzyl)imidazolium bromide

In a 25 ml one-necked flask, 1.4 g (17.05 mmol) of 1-methylimidazole are dissolved in 15 ml of 1,2-dichloroethane and then 4.89 g (20.46 mmol) of 3-trifluoromethylbenzyl bromide are added. After heating overnight at 80°, 50 ml of diethyl ether are added. The oil, which is then separated by decantation, is crystallized from a mixture of ethyl acetate and tetrahydrofuran (2/1 by volume). The crystals thus obtained are drained and then dried under reduced pressure. 3.06 g (56%) of 1-methyl-3-(3-trifluoromethylbenzyl)imidazolium bromide are thus obtained in the form of off-white crystals, used as they are in the next step, whose characteristic is the following:

LC/MS: Column ACQUITY BEH C18 1.7 μm of 2.1×50 mm, at 50° C.
Solvents: A=water containing 0.1% of formic acid; B=acetonitrile containing 0.1% of formic acid.
Gradient: from 5 to 50% of B in 0.8 min, and then from 50 to 100% of B in 0.4 min, and then 0.65 min at 100% of B, and then from 100 to 5% of B in 0.15 min
Flow rate: 1 ml/min
Retention time=0.40 min

Step 2: [1-methyl-3-(3-trifluoromethylbenzyl)imidazol-2-ylidene](1,3-divinyl-1,1,3,3-tetramethyldisiloxane)platinum(0)

By carrying out the procedure as in Step 1 of Example 32, but starting with 0.5 g (1.87 mmol) of 1-methyl-3-(3-trifluoromethylbenzyl)imidazolium bromide, obtained in the preceding step, and 0.217 g (0.935 mmol) of silver oxide in 50 ml of dichloromethane, and then 18.9 ml (1.89 mmol) of a 0.1 M solution of (1,3-divinyl-1,1,3,3-tetramethyldisiloxane)platinum(0) in xylene, there is obtained, after purification by crystallization from pentane, 0.513 g (44%) of [1-methyl-3-(3-trifluoromethylbenzyl)imidazol-2-ylidene](1,3-divinyl-1,1,3,3-tetramethyldisiloxane)platinum(0) in the form of fine white crystals whose characteristic is the following:

Rf=0.42 (silica gel, mixture of 90% of cyclohexane and 10% of ethyl acetate).

Step 3: trans-diiodo(N-cyclohexylamine)[1-methyl-3-(3-trifluoromethylbenzyl)-imidazol-2-ylidene]platinum(II)

By carrying out the procedure as in Step 3 of Example 11, but starting with 0.2 g (0.314 mmol) of the compound obtained in Step 2, in 20 ml of tetrahydrofuran, 83.7 mg (0.33 mmol) of diiodine in 5 ml of tetrahydrofuran and 39.53 μl (0.345 mmol) of cyclohexylamine, at room temperature for 24 h, there are obtained, after purification by flash chromatography, eluting with a mixture of cyclohexane and ethyl acetate (90/10 by volume), and then crystallization from 2 ml of pentane, 100 mg (40%) of trans-diiodo(N-cyclohexylamine)[1-methyl-3-(3-trifluoromethylbenzyl)imidazol-2-ylidene]platinum(II), in the form of fine yellow crystals whose characteristics are the following:

Rf=0.18 (silica gel, mixture of 90% of cyclohexane and 10% of ethyl acetate).

$^1$H NMR spectrum (400 MHz, CDCl$_3$): δ ppm: 1.09-1.46 (m, 5 H) 1.69 (ddd, J=13.1, 3.2, 3.0 Hz, 1 H) 1.82 (ddd, J=13.5, 3.5, 3.2 Hz, 2 H) 2.32 (dd, J=12.6, 2.7 Hz, 2 H) 2.82-3.09 (m, 2 H) 3.20-3.38 (m, 1H) 3.96 (s, 3 H) 5.73 (s, 2 H) 6.66 (d, J=2.0 Hz, 1 H) 6.89 (d, J=2.0 Hz, 1 H) 7.55 (t, J=7.8 Hz, 1 H) 7.65 (d, J=7.7 Hz, 1 H) 7.72 (d, J=7.7 Hz, 1 H) 7.76 (s, 1 H)

EXAMPLE 34 trans-dinitrato(N-cyclohexylamine)[1-methyl-3-(4-trifluoromethyl-benzyl)imidazol-2-ylidene]platinum (II)

In a 50 ml three-necked flask under an argon atmosphere, 80 mg (0.102 mmol) of trans-diiodo(N-cyclohexylamine)[1-methyl-3-(4-trifluoromethylbenzyl)imidazol-2-ylidene]platinum(II), obtained in Example 11, are dissolved in 20 ml of dichloromethane and then 36.2 mg (0.207 mmol) of silver nitrate are added and the mixture is stirred overnight at room temperature. The precipitated silver salts are filtered, and the filtrate is concentrated to dryness. The residue obtained is crystallized from a mixture of heptane and ethyl acetate (1/1 by volume). 9 mg (13%) of trans-dinitrato(N-cyclohexylamine)[1-methyl-3-(4-trifluoromethylbenzyl)imidazol-2-ylidene]platinum(II) are thus obtained in the form of fine white crystals whose characteristics are the following:

$^1$H NMR spectrum (400 MHz, CDCl$_3$): δ ppm: 1.14-1.26 (m, 1 H) 1.27-1.48 (m, 4 H) 1.67-1.77 (m, 1 H) 1.81-1.90 (m, 2 H) 2.30-2.41 (m, 2 H) 2.87 (br. s., 1 H) 3.32-3.44 (m, 2 H) 4.21 (s, 3 H) 5.88 (s, 2 H) 6.74 (d, J=2.0 Hz, 1 H) 6.94 (d, J=2.0 Hz, 1 H) 7.46 (d, J=8.1 Hz, 2 H) 7.70 (d, J=8.1 Hz, 2 H)

LC/MS: Column ACQUITY BEH C18 1.7 μm of 2.1×50 mm, at 50° C.
Solvents: A=water containing 0.1% of formic acid; B=acetonitrile containing 0.1% of formic acid.
Gradient: from 5 to 50% of B in 0.8 min, and then from 50 to 100% of B in 0.4 min, and then 0.65 min at 100% of B, and then from 100 to 5% of B in 0.15 min
Flow rate: 1 ml/min
Retention time=0.51 min

EXAMPLE 35 trans-diiodo(N-cyclohexylamine)[3-(3,4-dimethoxybenzyl)-1-methylimidazol-2-ylidene]platinum(II)

Step 1: (3,4-dimethoxybenzyl)-1-methylimidazolium bromide

In a 25 ml one-necked flask, 0.35 g (4.26 mmol) of 1-methylimidazole is dissolved in 10 ml of tetrahydrofuran and then 1.18 g (5.12 mmol) of 3,4-dimethoxybenzyl bromide are added. After heating under reflux overnight, 50 ml of diethyl ether are added. The precipitate formed is drained and then washed with diethyl ether. 1.25 g (94%) of 3-(3,4-dimethoxybenzyl)-1-methylimidazolium bromide are thus obtained in the form of a light beige powder, used as it is in the next step, whose characteristic is the following:
- LC/MS: Column ACQUITY BEH C18 1.7 µm of 2.1×50 mm, at 50° C.
  - Solvents: A=water containing 0.1% of formic acid; B=acetonitrile containing 0.1% of formic acid.
  - Gradient: from 5 to 50% of B in 0.8 min, and then from 50 to 100% of B in 0.4 min, and then 0.65 min at 100% of B, and then from 100 to 5% of B in 0.15 min
  - Flow rate: 1 ml/min
  - Retention time=0.38 min Step 2: [3-(3,4-dimethoxybenzyl)-1-methylimidazol-2-ylidene](1,3-divinyl-1,1,3,3-tetramethyldisiloxane) platinum(0)

By carrying out the procedure as in Step 1 of Example 32, but starting with 0.753 g (2.235 mmol) of 3-(3,4-dimethoxybenzyl)-1-methylimidazolium bromide, obtained in the preceding step, and 0.259 g (1.118 mmol) of silver oxide in 100 ml of dichloromethane, and then 24.6 ml (2.46 mmol) of a 0.1 M solution of (1,3-divinyl-1,1,3,3-tetramethyldisiloxane)platinum(0) in xylene, there is obtained, after purification by crystallization from pentane, 0.525 g (38%) of [3-(3,4-dimethoxybenzyl)-1-methylimidazol-2-ylidene](1,3-divinyl-1,1,3,3-tetramethyldisiloxane)platinum(0) in the form of fine white crystals whose characteristic is the following:
- LC/MS: Column ACQUITY BEH C18 1.7 µm of 2.1×50 mm, at 50° C.
  - Solvents: A=water containing 0.1% of formic acid; B=acetonitrile containing 0.1% of formic acid.
  - Gradient: from 5 to 50% of B in 0.8 min, and then from 50 to 100% of B in 0.4 min, and then 0.65 min at 100% of B, and then from 100 to 5% of B in 0.15 min
  - Flow rate: 1 ml/min
  - Retention time=1.28 min Step 3: trans-diiodo(N-cyclohexylamine)[3-(3,4-dimethoxybenzyl)-1-methyl-imidazol-2-ylidene] platinum(II)

By carrying out the procedure as in Step 3 of Example 11, but starting with 0.4 g (0.652 mmol) of the compound obtained in Step 2, in 35 ml of tetrahydrofuran, 174 mg (0.686 mmol) of diiodine in 5 ml of tetrahydrofuran and 82 µl (0.717 mmol) of cyclohexylamine, at room temperature for 24 h, there are obtained, after purification by crystallization from a mixture of pentane and tetrahydrofuran (10/1 by volume), 256 mg (50%) of trans-diiodo(N-cyclohexylamine)[3-(3,4-dimethoxybenzyl)-1-methylimidazol-2-ylidene]platinum(II), in the form of fine yellow crystals whose characteristics are the following:
- Rf=0.27 (silica gel, mixture of 90% of cyclohexane and 10% of ethyl acetate).
- $^1$H NMR spectrum (400 MHz, CDCl$_3$): δ ppm: 1.07-1.42 (m, 5 H) 1.63 (ddd, J=12.9, 3.6, 3.4 Hz, 1 H) 1.77 (dt, J=13.5, 3.4 Hz, 2 H) 2.29 (d, J=13.6 Hz, 2 H) 2.84-3.04 (m, 2 H) 3.22-3.32 (m, 1 H) 3.86 (s, 3 H) 3.88 (s, 3 H) 3.89 (s, 3 H) 5.53 (s, 2 H) 6.58 (d, J=2.0 Hz, 1 H) 6.77 (d, J=2.2 Hz, 1 H) 6.84 (d, J=8.1 Hz, 1 H) 6.95 (dd, J=8.1, 2.0 Hz, 1 H) 7.12 (d, J=2.0 Hz, 1 H)

EXAMPLE 36 trans-diiodo(N-morpholine)(1-methyl-3-(4-trifluoromethylbenzyl)-imidazol-2-ylidene)platinum(II)

To a solution of the complex [1-methyl-3-(4-trifluoromethylbenzyl)imidazol-2-ylidene](1,3-divinyl-1,1,3,3-tetramethyldisiloxane)]platinum(0), obtained in Step 2 of Example 11, (0.5 g, 0.804 mmol) in 5 ml of tetrahydrofuran at 0° C., there is added a solution of diiodine (214.3 mg, 0.844 mmol) in 5 ml of tetrahydrofuran. Next, a solution of 77.4 µl (0.884 mmol) of morpholine in 2 ml of tetrahydrofuran is added to the mixture. The reaction mixture is stirred for 18 h at room temperature and then evaporated to dryness. The residue obtained is purified by flash chromatography on silica gel, eluting with a mixture of heptane and ethyl acetate (85/15 by volume), 260 mg (42%) of trans-diiodo(N-morpholine)(1-methyl-3-(4-trifluoromethylbenzyl)imidazol-2-ylidene)platinum(II), are thus obtained in the form of a yellow powder whose characteristics are the following:
- $^1$H NMR spectrum (400 MHz, CDCl$_3$) δ ppm: 2.96 (d, J=12.5 Hz, 2 H) 3.21-3.52 (m, 1 H) 3.51-3.74 (m, 4 H) 3.87 (d, J=9.6 Hz, 2 H) 3.94 (s, 3 H) 5.71 (s, 2 H) 6.64 (s, 1 H) 6.89 (s, 1 H) 7.55-7.64 (m, 2 H) 7.65-7.74 (m, 2 H)
- LC/MS: Column ACQUITY BEH C18 1.7 µm of 2.1×50 mm, at 50° C.
  - Solvents: A=water containing 0.1% of formic acid; B=acetonitrile containing 0.1% of formic acid.
  - Gradient: from 5 to 50% of B in 0.8 min, and then 50 to 100% of B in 0.4 min, and then 0.65 min at 100% of B, and then from 100 to 5% of B in 0.15 min
  - Flow rate: 1 ml/min
  - Retention time=1.16 min

EXAMPLE 37 trans-diiodo(N-tetrahydropyran-4-ylamine)(1-methyl-3-(4-trifluoro-methylbenzyl)imidazol-2-ylidene) platinum(II)

To a solution of [1-methyl-3-(4-trifluoromethylbenzyl)imidazol-2-ylidene](1,3-divinyl-1,1,3,3-tetramethyldisiloxane)]platinum(0), obtained in Step 2 of Example 11, (0.4 g, 0.643 mmol) in 5 ml of tetrahydrofuran at 0° C., there is added a solution of diiodine (171.5 mg, 0.676 mmol) in 5 ml of tetrahydrofuran. Next, a solution of 71.6 mg (0.708 mmol) of 4-aminotetrahydropyran chloride in 2 ml of tetrahydrofuran and 0.1 ml of diisopropylethylamine is added to the mixture. The reaction mixture is stirred overnight at room temperature and then evaporated to dryness. The residue obtained is purified by flash chromatography on silica gel, eluting with a mixture of heptane and ethyl acetate (80/20 by volume), 180 mg (35%) of trans-diiodo(N-tetrahydropyran-4-ylamine)(1-methyl-3-(4-trifluoromethylbenzyl)imidazol-2-ylidene) platinum(II) are thus obtained in the form of a yellow powder whose characteristics are the following:
- $^1$H NMR spectrum (400 MHz, CDCl$_3$) δ ppm: 1.61-1.68 (m, 2 H) 2.26 (d, J=14.0 Hz, 2 H) 2.96-3.18 (m, 2 H) 3.35-3.62 (m, 3 H) 3.96 (s, 3 H) 3.99-4.08 (m, 2 H) 5.73 (s, 2 H) 6.65 (s, 1 H) 6.90 (s, 1 H) 7.54-7.65 (m, 2 H) 7.66-7.73 (m, 2 H)
- LC/MS: Column ACQUITY BEH C18 1.7 µm of 2.1×50 mm, at 50° C.
  - Solvents: A=water containing 0.1% of formic acid; B=acetonitrile containing 0.1% of formic acid.
  - Gradient: from 5 to 50% of B in 0.8 min, and then from 50 to 100% of B in 0.4 min, and then 0.65 min at 100% of B, and then from 100 to 5% of B in 0.15 min
  - Flow rate: 1 ml/min
  - Retention time=1.12 min

EXAMPLE 38 trans-dibromo(N-cyclohexylamine)[1-methyl-3-(4-trifluoromethyl-benzyl)imidazol-2-ylidene]platinum (II)

In a 25 ml three-necked flask, 300 mg (0.482 mmol) of [1-methyl-3-(4-trifluoro-methylbenzyl)imidazol-2-ylidene](1,3-divinyl-1,1,3,3-tetramethyldisiloxane)]platinum(0), obtained in Step 2 of Example 11, are dissolved in 5 ml of tetrahydrofuran, a solution of 24.9 μl (0.482 mmol) of dibromine in 2 ml of tetrahydrofuran is added. Next, after almost complete decolourization of the preceding solution, 55.2 μl (0.482 mmol) of cyclohexylamine are added. After stirring overnight at room temperature, the reaction medium is concentrated under reduced pressure. The residue obtained is purified by flash chromatography on an alumina column, eluting with a gradient of mixtures of heptane and ethyl acetate (from 90/10 to 70/30 by volume). 20 mg (6%) of trans-dibromo(N-cyclohexylamine)[1-methyl-3-(4-trifluoromethylbenzyl)imidazol-2-ylidene]platinum(II) are thus obtained in the form of a golden yellow powder whose characteristics are the following:

$^1$H NMR spectrum (400 MHz, CDCl$_3$): δ ppm: 1.10-1.48 (m, 5 H) 1.63-1.73 (m, 1 H) 1.75-1.87 (m, 2 H) 2.34 (d, J=13.8 Hz, 2 H) 2.78-3.06 (m, 2 H) 3.12-3.31 (m, 1 H) 4.10 (s, 3 H) 5.85 (s, 2 H) 6.69 (s, 1 H) 6.89 (s, 1 H) 7.57-7.64 (m, 2 H) 7.64-7.71 (m, 2 H)

LC/MS: Column ACQUITY BEH C18 1.7 μm of 2.1×50 mm, at 50° C.
  Solvents: A=water containing 0.1% of formic acid; B=acetonitrile containing 0.1% of formic acid.
  Gradient: from 5 to 50% of B in 0.8 min, and then from 50 to 100% of B in 0.4 min, and then 0.65 min at 100% of B, and then from 100 to 5% of B in 0.15 min
  Flow rate: 1 ml/min
  Retention time=1.49 min Reference product of the publication by S. Ray, R. Mohan, J. Singh, M. Samantaray, M. Shaikh, D. Panda and P. Ghosh "Anticancer and Antimicrobial Metallopharmaceutical Agents Based on Palladium, Gold and Silver N-Heterocyclic Carbene Complexes" J. Am. Chem. Soc. Vol. 129, no. 48 pages 15042-15053; (2007 Dec. 5):

trans-diiodo(pyridine)(1-benzyl-3-tert-butylimidazol-2-ylidene)platinum(II)

Step 1: 1-benzyl-3-tert-butylimidazolium chloride

A solution of 1-tert-butylimidazole, which was obtained according to A. J. Arduengo (2001) U.S. Pat. No. 6,177,575, (0.31 g; 2.5 mmol) in benzyl chloride (0.3 ml; 2.5 mmol) is stirred at room temperature for 48 h. The volatiles are then evaporated under vacuum. The residue obtained is triturated in ethyl ether and then filtered, thus making it possible to obtain 0.54 g (87%) of 1-benzyl-3-tert-butylimidazolium chloride whose characteristics are the following:

$^1$H NMR (300 MHz, CDCl$_3$) δ ppm: 1.73 (s, 9H), 5.71 (s, 2H), 7.15 (m, 1H), 7.25 (m, 1H), 7.38 (m, 3H), 7.52 (m, 2H), 11.41 (s, 1H).

Step 2: [1-benzyl-3-tert-butylimidazol-2-ylidene(1,3-divinyl-1,1,3,3-tetramethyl-disiloxane)]platinum(0)

To a solution of 1-benzyl-3-tert-butylimidazolium chloride (0.18 g; 0.7 mmol) in 10 ml of chloroform, there is added a 0.1 M solution of 1,3-divinyl-1,1,3,3-tetramethyl-disiloxane-platinum(0) in xylene (7 ml; 0.7 mmol). The mixture is cooled to 0° C. and 0.12 g of potassium tert-butoxide (1.03 mmol) is added. The reaction mixture is stirred for 16 h at room temperature and then evaporated to dryness. The residue obtained is purified by flash chromatography by elution with a mixture of heptane and ethyl acetate (95/5 by volume). 0.17 g (42%) of [1-benzyl-3-tert-butylimidazol-2-ylidene(1,3-divinyl-1,1,3,3-tetramethyldisiloxane)]platinum(0) is thus recovered in the form of a 1:1 mixture of two isomers.

$^1$H NMR (300 MHz, CDCl$_3$) δ ppm: -0.45 (s, 6H), -0.27 (s, 6H), 0.30 (s, 6H), 0.32 (s, 6H), 1.61 (s, 9H), 1.64 (s, 9H), 1.8-1.9 (m, 8H), 2.1-2.3 (m, 4H), 5.16 (s, 2H), 5.28 (s, 2H), 6.84 (br s, 1H), 6.90 (br s, 1H), 7.08 (m, 4H), 7.20-7.35 (m, 6H).

Step 3: trans-diiodo(pyridine)(1-benzyl-3-tert-butyl-imidazol-2-ylidene)platinum(II)

To a solution of (1-benzyl-3-tert-butylimidazol-2-ylidene)(1,3-divinyl-1,1,3,3-tetramethyldisiloxane)platinum(0) (0.07 g; 0.12 mmol), obtained in the preceding step, in 5 ml of toluene at 0° C., there is added a solution of diiodine (0.03 g; 0.13 mmol) in 11 ml of toluene. Next, 15 μl of pyridine (0.12 mmol) are added to the mixture. The reaction mixture is stirred for 16 h at room temperature and then evaporated to dryness. The residue obtained is purified by flash chromatography by elution with a gradient of mixtures of heptane and ethyl acetate (80/20 to 70/30 by volume), 0.07 g (80%) of (1-benzyl-3-tert-butylimidazol-2-ylidene)(1,3-divinyl-1,1,3,3-tetramethyldisiloxane)platinum(0) is thus recovered whose characteristics are the following:

$^1$H NMR (300 MHz, CDCl$_3$) δ ppm: 2.08 (s, 9H), 5.99 (s, 2H), 6.57 (d, 1H), 7.02 (d, 1H), 7.3-7.5 (m, 5H), 7.53 (m, 2H), 7.71 (m, 1H), 9.06 (m, 2H).

HRMS mass spectrum (ESI positive mode) calculated for $C_{19}H_{23}I_2N_3Pt.Na$: 764.9527; found for $C_{19}H_{23}I_2N_3NaPt$: 764.9525.

The table which follows illustrates the chemical structures of some examples of compounds according to the invention. In this table:
  Me represents methyl,
  Ph and Bn represent phenyl and benzyl groups, respectively.

TABLE

| No. | R1 | R2 | R3 | V | RR'NH | X | MM (molecular mass) |
|-----|----|----|----|----|-------|---|---------------------|
| 1 | Me | Me | H | CH | H$_2$N-cyclohexyl | I | 644.21 |

TABLE-continued
| No. | R1 | R2 | R3 | V | RR'NH | X | MM (molecular mass) |
|---|---|---|---|---|---|---|---|
| 2 | Me | Me | H | N | 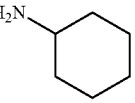 | I | 645.20 |
| 3 | Me | 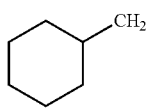 | H | CH | 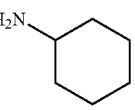 | I | 726.36 |
| 4 | Me | Ph | H | CH | 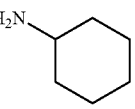 | I | 706.28 |
| 5 | Me | Bn | H | CH | 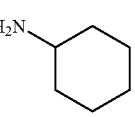 | I | 720.31 |
| 6 | Me | Me | H | CH | 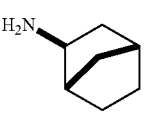<br>exo (+/−) | I | 656.22 |
| 7 | Me | Me | |  | 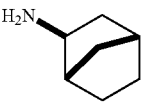<br>exo (+/−) | I | 706.28 |
| 8 | Me | Me | |  | 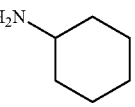 | I | 694.27 |
| 9 | Me | Me | | 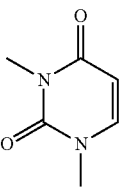 | 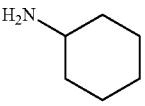 | I | 756.30 |
| 10 | Me | 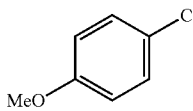 | H | CH | 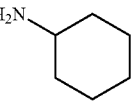 | I | 750.33 |
| 11 | Me | 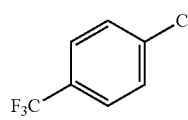 | H | CH | 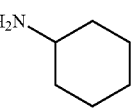 | I | 788.31 |
| 12 | Bn | Bn | H | CH | 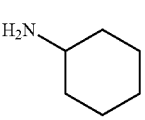 | I | 796.41 |
| 13 | Me | Me | H | CH | H$_2$N—Bn | I | 652.19 |

TABLE-continued
| No. | R1 | R2 | R3 | V | RR'NH | X | MM (molecular mass) |
|---|---|---|---|---|---|---|---|
| 14 | Me | Me | H | CH | 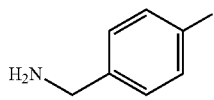 | I | 720.19 |
| 15 | Me | CH=CH$_2$ | H | CH |  | I | 656.22 |
| 16 | Me | Me |  | | 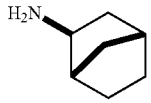<br>exo (−) | I | 706.28 |
| 17 | Me | Me |  | | 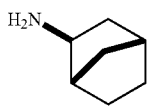<br>exo (+) | I | 706.28 |
| 18 |  |  | H | CH | 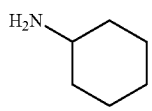 | I | 780.45 |
| 19 | Me | Ph | H | N | 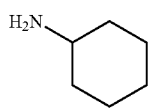 | I | 707.27 |
| 20 | Me | Me | Ph | CH | 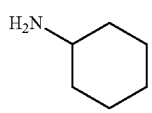 | I | 720.31 |
| 21 | Me | Bn | Ph | CH | 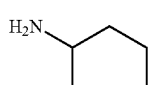 | I | 796.41 |
| 22 | Me | Me | Ph | C—Ph | 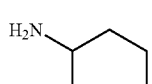 | I | 796.41 |
| 23 | Me | Me | H | CH | 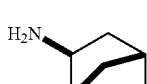<br>exo (−) | I | 656.22 |
| 24 | Me | Me | H | CH | 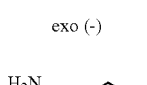<br>exo (+) | I | 656.22 |

TABLE-continued

| No. | R1 | R2 | R3 | V | RR'NH | X | MM (molecular mass) |
|---|---|---|---|---|---|---|---|
| 25 | Me | Me | | 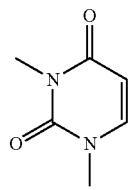 | 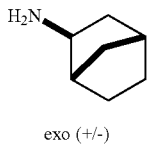 exo (+/−) | I | 768.31 |
| 26 | Me | Bn | Ph | C—Ph | 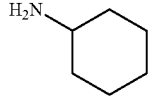 | I | 872.51 |
| 27 | Me | Bn | H | CH | 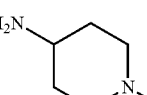 | I | 735.32 |
| 28 | Me | Bn | H | CH | 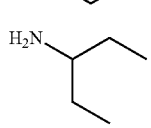 | I | 707.29 |
| 29 | Me | Bn | H | CH | 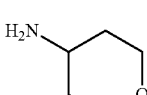 | I | 722.28 |
| 30 | Me | Bn | H | CH | 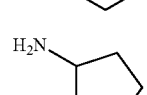 | I | 705.27 |
| 31 | Me | Bn | H | CH | 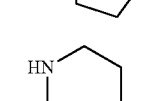 | I | 707.24 |
| 32 | Me | 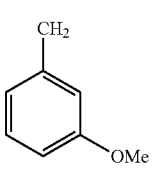 | H | CH | 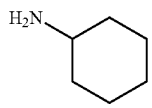 | I | 749.33 |
| 33 | Me | 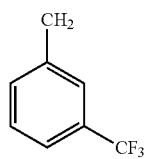 | H | CH | 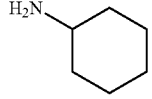 | I | 788.31 |

The compounds according to the invention have been the subject of pharmacological trials which make it possible to determine their inhibitory effect on cells sensitive to platinum derivatives.

Trials consisted in measuring the in vitro activity of the compounds of the invention on H460 and CEM strains, and on the strains A2780, A2780 resistant to DDP, CH1, CH1 resistant to DPP and SKOV3.

Many tumours are resistant to platinum compounds. Two main mechanisms are involved:

First mechanism: The tumour resistance is attributed to inadequate levels of platinum compounds capable of reaching the DNA Platinum compounds penetrate into the cell either via transporters, such as the copper transporter CRT1, or by passive diffusion across the plasma membrane. Inside the cell, the platinum compounds form reactive aqueous chemical variants which react particularly with sulphur-containing molecules such as glutathione or metallothioneins. Finally, the platinum compounds are actively exported from the cell through the copper exporters ATP7A and ATP7B, or by the exporting pump GS-X (Glutathione-S-X). The absence of CTR1 receptors, or high levels of glutathione, or high expressions of active exporters may be involved in the mechanisms of innate or acquired resistance of tumour cells to platinum compounds.

Second mechanism: Mechanisms of resistance of tumour cells following the binding of platinum compounds to DNA In the nucleus, platinum compounds covalently bind to 2 adjacent guanines: this is referred to as the formation of adducts. However, the damage caused by these adducts can be circumvented by the cell, which can use several repair mechanisms:

nucleotide-excision repair (NER), inactivation or deletion of the DNA mismatch repair (MMR) mechanism, bypassing of the adducts by some polymerases or weakness of the process of programmed cell death (apoptosis). All these mechanisms may be responsible for the resistance observed in many tumour cells to platinum compounds.

The platinum complexes of the invention are evaluated on cells expressing one or more of these mechanisms:

CCRF-CEM is a human T leukaemia (Cancer 1965, 18: 522-529). Oxaliplatin induces bifunctional lesions such as inter- and intra-DNA strand adducts on these CCRF-CEM cells (Mol Pharmacol 2000, 58: 920-927). CCRF-CEM cells do not possess the MLH1 protein, one of the two principal proteins involved in the MMR mechanism in human cancers. This deficiency makes these cells particularly resistant to alkylating agents and to platinum compounds.

NCI-H460 is a human non-small cell lung cancer which has a mutation in the K-ras gene. This cell is sensitive to platinum compounds. In this cell line, cisplatin forms more adducts than oxaliplatin at the same concentration and yet the percentage repair is higher for oxaliplatin (DNA Repair 2006, 5: 219-225).

SK-OV-3 is a human ovarian cancer. Like the CCRF-CEM cell, it does not have the MLH1 protein (Mol Pharmacol 2000, 58: 920-927; BMC cancer 2006; 6:201). This cell has an intrinsic mechanism of resistance to cisplatin which is linked to high levels of glutathione (Br J Cancer 1998; 78:175-180). This cell line is commonly used to explore the effects of high levels of glutathione on the resistance to platinum compounds (Br J Cancer 1996, 74: 380-386).

A2780 and A2780/DDP are human ovarian cancer lines. A2780 does not express the gene for the MLH1 protein (BMC cancer 2006; 6: 201). The resistance of the A2780/DDP line is of the acquired type and involves various mechanisms:—reduction in the capacity for internalization of cisplatin,—replicative bypass (this is defined as the possibility for a replicative complex to synthesize DNA beyond the site of damage) (Cancer Res 1994; 54:3500-3505),—active detoxification by glutathione (Exp Oncol 2005; 27:191-195),—low activity of Caspase-3, enzymes involved in the process of programmed cell death (J Cancer Res Clin Oncol 2004; 130: 423-428) and finally high nuclear efflux of platinum compounds (Oncol Rep 2004; 12:1365-1370).

CH1 and CH1 CisR are human ovarian cancers which are sensitive and resistant to cisplatin, respectively. The relative sensitivity of the CH1 cell may be at least partially attributed to a deficiency of a gene involved in repair processes and which is capable of removing the adducts (Chemico-Biological Interactions, 1999; 123:11-29). The CH1cisR cell is resistant to cisplatin through a poorly known mechanism of DNA repair, or increase in the tolerance of the cell to the damage caused by cisplatin to the DNA of this cell (Mol Pharmacol 2003; 63:933-944, *Cancer Res* 52: 3857-3864).

Tests of Cytotoxicity:

For adherent cells: Cell proliferation is evaluated by the incorporation of $^{14}$C-thymidine into the DNA of the cells. A549, CH1, CH1/DDP and H460 are cultured in Dulbecco's modified Eagle's medium (DMEM), SK-OV-3 in Mc-Coy medium, A2780 and A2780/DDP in RPMI1640 medium. All the media contain 10% foetal calf serum, 2 mM L-glutamine, 100 units/ml of penicillin and 100 mg/ml of streptomycin. The incubation is performed at 37° C. in a 95% air/5% $CO_2$ atmosphere.

The cells, at the exponential growth phase, are introduced into the wells of a Cytostar 96-well plate, containing a scintillation fluid (Cytostar-T scintillating microplate, GE Healthcare Bio-Sciences AB, Uppsala, Sweden), at the density of $5 \times 10^3$ to $10^4$ cells per well, in an amount of 180 μl per well. After incubating for 4 hours, the test compounds are added. The compounds are prepared beforehand as a stock solution at the concentration of 10 mM in DMSO. A serial dilution is performed before the compounds are brought into contact with the cells in a volume of 10 μl. After incubating for 72 hours at 37° C. in an atmosphere of 95% air/5% $CO_2$, 0.1 μCi/well of $^{14}$C-thymidine is added. 24 h later (total 96 h of treatment), the incorporation of $^{14}$C-thymidine is recorded on a suitable scintillation counter (MicroBeta radioactivity counting, Perkin-Elmer Life Sciences, Boston, Mass., USA). The mean values obtained in the experimental groups are divided by the mean values obtained in the control groups in order to obtain percentages relative to the controls.

For the non-adherent CCRF-CEM cells, the cell viability is measured by the luminescence test CellTiter-Glo® Luminescent Cell Viability Assay (Promega, Madison, Wis., USA). When it is added to the cells, the reagent produces a luminescence in the presence of the ATP of the living cells. The results are evaluated on a suitable reader (Envision, Perkin-Elmer Life Sciences, Boston, Mass., USA).

The CCRF-CEM cells are cultured in RPMI1640 medium containing 10% foetal calf serum, 2 mM L-glutamine, 100 units/ml of penicillin and 100 mg/ml of streptomycin, at 37° C. in a 95% air/5% $CO_2$ atmosphere. The cells, at the exponential growth phase, are introduced into the wells of a 96-well plate at the density of $5 \times 10^3$ cells per well in an opaque plate (Greiner), in a volume of 150 μl. After incubating for 4 h at 37° C. in a 95% air/5% $CO_2$ atmosphere, the compounds (concentrated 20-fold) are added in a volume of 8 μl. The compounds are prepared beforehand as a stock solution at the concentration of 10 mM in DMSO. A serial dilution is performed before the compounds are brought into contact with the cells. After incubating for 96 h at 37° C., 100 μl of agents (CellTiter-Glo) are added. After lysing the cells, the release of ATP is evaluated on the Envision reader.

The $IC_{50}$ values are evaluated from curves presenting the percentage viability as a function of the concentration of the test compound, using the Biostat speed software. The $IC_{50}$ is defined as the concentration of the compound which inhibits 50% of the cell proliferation or 50% of the cell viability.

The cell viability may also be evaluated by the "Titer 96 assay" kit (Promega, Madison, Wis., USA), which uses 3-(4, 5-dimethylthiazol-2-yl)-5-(3-carboxymethoxyphenyl)-2-(4-sulphophenyl)-2H-tetrazolium] (MTS) (Cancer Commun. 1991; 3:207-212), regardless of the cell type. This test is one of those most commonly used in the literature. It uses a colorimetric absorption method based on the capacity of the dehydrogenase enzymes of living cells to produce formazan, a brownish compound which is detectable at 490 nm. For that, after incubation, 20 μl of MTS reagent are added to the culture wells and the plate is incubated for a further 1-3 hours. A measurement of the background signal is evaluated from wells containing the cells to which 20 µl of Triton X100 were added at the end of the incubation. The cell survival is evaluated by measuring the absorbance at 490 nm using a suitable counter (Victor2 Wallac plate reader, Perkin Elmer, Boston, Mass., USA).

The inhibitory activity towards these strains is given by the concentration which inhibits 50% of the activity of each of them.

The $IC_{50}$ values of some of the compounds according to the invention are between 1 µM and 5 µM on strains sensitive to cisplatin or oxaliplatin.

The table below shows the results obtained with the examples described above:

| Example | CEM $IC_{50}$ µM | H460 $IC_{50}$ µM | A2780 $IC_{50}$ µM | A2780/ DDP $IC_{50}$ µM | CH1 $IC_{50}$ µM | CH1/ DDP $IC_{50}$ µM | SKOV3 $IC_{50}$ µM |
|---|---|---|---|---|---|---|---|
| Cisplatin | 3 | 2.4 | 9 | >10 | 8 | >10 | 6.1 |
| Carboplatin | 3.3 | 9.7 | >10 | >10 | >10 | >10 | >10 |
| Oxaliplatin | 0.9 | 4 | 3.9 | 17.3 | 4.2 | 6.2 | >10 |
| 1 | 2.8 | 5.4 | nd | nd | nd | nd | nd |
|   | 1.9 | 3.0 |    |    |    |    |    |
| 2 | 1.5 | 2.5 | nd | nd | nd | nd | nd |
| 3 | 2.0 | 3.8 | 1.0 | 1.2 | 2.3 | 2.0 | 5.3 |
| 4 | 1.5 | 2.3 | nd | nd | nd | nd | nd |
| 5 | 1.2 | 1.7 | 0.9 | 1.8 | 2.4 | 2.4 | 6.5 |
|   | 1.4 | 2.7 |    |    |    |    |    |
| 6 | 1.7 | 2.8 | nd | nd | nd | nd | nd |
| 7 | 1.3 | 1.9 | 0.4 | 1.8 | 2.5 | 2.4 | 7.0 |
| 8 | 3.1 | 1.9 | nd | nd | nd | nd | nd |
| 9 | 2.7 | 1.6 | 1.8 | 1.4 | 2.2 | 2.1 | >10 |
| 10 | 1.6 | 3.8 | 1.6 | 2.3 | nd | nd | 5.2 |
| 11 | 1.0 | 1.5 | 0.8 | 1.1 | nd | nd | 2.6 |
| 12 | 1.3 | 3.4 | 0.7 | 1.2 | nd | nd | 2.8 |
| 13 | 1.7 | 3.0 | nd | nd | nd | nd | nd |
| 14 | 1.7 | 2.6 | nd | nd | nd | nd | nd |
| 15 | 2.1 | 3.8 | nd | nd | nd | nd | nd |
| 16 | 1.4 | 4.1 | 1.1 | 2.7 | nd | nd | 4.1 |
| 17 | 1.8 | 1.1 | 1.1 | 2.2 | nd | nd | 5.0 |
| 18 | 1.4 | 2.7 | nd | nd | nd | nd | nd |
| 19 | 1.0 | 2.3 | nd | nd | nd | nd | nd |
| 20 | 2.1 | 4.4 | nd | nd | nd | nd | nd |
| 21 | 0.9 | 1.9 | nd | nd | nd | nd | nd |
| 22 | 1.2 | 1.8 | nd | nd | nd | nd | nd |
| 23 | 1.6 | 2.3 | nd | nd | nd | nd | nd |
| 24 | 0.9 | 2.1 | nd | nd | nd | nd | nd |
| 25 | 1.0 | 1.5 | nd | nd | nd | nd | nd |
| 26 | 1.2 | 2.9 | nd | nd | nd | nd | nd |
| 27 | 1.6 | 1.7 | nd | nd | nd | nd | nd |
| 28 | 1.4 | 1.6 | nd | nd | nd | nd | nd |
| 39 | 0.5 | 0.9 | nd | nd | nd | nd | nd |
| 30 | 1.1 | 1.3 | nd | nd | nd | nd | nd |
| 31 | 0.7 | 0.9 | nd | nd | nd | nd | nd |
| 32 | 1.2 | 1.4 | nd | nd | nd | nd | nd |
| 33 | 0.7 | 0.8 | nd | nd | nd | nd | nd |
| 34 | 1.4 | 3.1 | nd | nd | nd | nd | nd |
| 35 | 1.3 | 2.7 | nd | nd | nd | nd | nd |
| 36 | 0.6 | 0.9 | nd | nd | nd | nd | nd |
| 37 | 0.9 | 1.4 | nd | nd | nd | nd | nd |
| 38 | 2.2 | 3 | nd | nd | nd | nd | nd |
| Reference product | 3.9 | 4.4 | nd | nd | nd | nd | nd |

Other trials were performed which consisted in measuring the in vivo activity of the compounds of the invention, especially on the leukaemias L1210 and L1210/DDP.

The compounds according to the invention may therefore be used for the preparation of medicaments, in particular of medicaments inhibiting the growth of solid tumours or leukaemias in humans, in particular of solid or liquid tumours which do not satisfactorily respond to a chemotherapy based on cisplatin, carboplatin or oxaliplatin.

Thus, according to another of its aspects, the subject of the invention is medicaments which comprise a compound of formula (I), or a hydrate or a solvate of the compound of formula (I).

These medicaments find use in therapy, in particular in the treatment of cancers. They are particularly active in the treatment of solid cancers such as for example cancers of the digestive tube such as gastric or colorectal cancers, lung, breast or prostate cancers, or liquid tumours such as leukaemias.

According to another of its aspects, the present invention relates to pharmaceutical compositions comprising, as active ingredient, a compound according to the invention. These pharmaceutical compositions contain an effective dose of at least one compound according to the invention, a hydrate or a solvate of the said compound, and at least one pharmaceutically acceptable excipient.

The said excipients are chosen, according to the pharmaceutical dosage form and the desired mode of administration, from the customary excipients which are known to persons skilled in the art.

In the pharmaceutical compositions of the present invention for subcutaneous, intramuscular or intravenous administration, the active ingredient of formula (I) above, or its possible solvate or hydrate, may be administered in unit dosage form, mixed with conventional pharmaceutical excipients, to animals and to human beings for the treatment of cancer diseases or disorders.

The appropriate unit dosage forms comprise the forms for parenteral, in particular subcutaneous, intramuscular or intravenous administration.

By way of example, a unit dosage form for a compound according to the invention in the form of a solution may comprise the following components:

| Compound according to the invention | 10 to 100 mg |
|---|---|
| Water for injection | 2 to 20 ml |

According to another embodiment of the invention, the compound may be provided in the form of a lyophilisate.

It is preferable to use the compounds according to the invention intravenously at doses of between 10 and 200 mg/m². There may be special cases where higher or lower dosages are appropriate; such dosages do not depart from the scope of the invention. According to the usual practice, the dosage appropriate for each patient is determined by the doctor according to the mode of administration, the weight and the response of the said patient.

The present invention, according to another of its aspects, also relates to a method for treating the pathologies indicated above, which comprises the administration, to a patient, of an effective dose of a compound according to the invention, or hydrates or solvates.

The invention claimed is:

1. A method of treating leukemia, ovarian cancer, or non-small cell lung cancer in a patient in need thereof, said method comprising administering to said patient an effective amount of an N-heterocyclic carbene-platinum complex bearing in trans of the carbine a nitrogen-containing ligand and corresponding to the general formula (I):

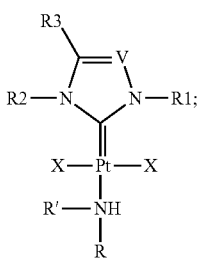

(I)

or a pharmaceutically acceptable salt thereof,
wherein:
  $R_1$ and $R_2$ each represents, independently of each other, an aryl or aralkyl group, each optionally substituted; a linear or branched C1-C6 alkyl group; a monocyclic C3-C7 cycloalkyl group; or a linear or branched C2-C6 alkenyl group;
  R' represents a hydrogen atom;
  R represents a group chosen from C3-C8 mono- or bicyclic cycloalkyl or heterocycloalkyl groups or an optionally substituted benzyl group;
  or R and R' form together with NH a C3-C8 mono- or bicyclic heterocycloalkyl;
  V represents a nitrogen atom or a C—$R_4$ radical;
  $R_3$ and $R_4$ each represents, independently of each other, hydrogen or a phenyl group,
  or $R_3$ and $R_4$ form together a C3-C6 alkylene or C3-C6 heteroalkylene radical with one or more nitrogen-based heteroatoms, it being possible for the carbon atoms of the heteroalkylene radical to be modified in the form of a carbonyl radical; and
  X represents iodine, bromine, chlorine or a nitrato (—$ONO_2$) group.

2. The method according to claim 1, wherein said N-Heterocyclic carbene-platinum complex is:
  trans-diiodo(N-cyclohexylamine)(1,3-dimethylimidazol-2-ylidene)platinum(II);
  trans-dibromo(N-cyclohexylamine)(1,3-dimethylimidazol-2-ylidene)platinum(II);
  trans-dichloro(N-cyclohexylamine)(1,3-dimethylimidazol-2-ylidene)platinum(II);
  trans-dinitrato(N-cyclohexylamine)(1,3-dimethylimidazol-2-ylidene)platinum(II);
  trans-diiodo(N-cyclohexylamine)(1,4-dimethyl-1,2,4-triazol-3-ylidene)platinum(II);
  trans-dibromo(N-cyclohexylamine)(1,4-dimethyl-1,2,4-triazol-3-ylidene)platinum(II);
  trans-dichloro(N-cyclohexylamine)(1,4-dimethyl-1,2,4-triazol-3-ylidene)platinum(II);
  trans-dinitrato(N-cyclohexylamine)(1,4-dimethyl-1,2,4-triazol-3-ylidene)platinum(II);
  trans-diiodo(N-cyclohexylamine)(1-methyl-3-(cyclohexylmethyl)imidazol-2-ylidene)platinum(II);
  trans-dibromo(N-cyclohexylamine)(1-methyl-3-(cyclohexylmethyl)imidazol-2-ylidene)platinum(II);
  trans-dichloro(N-cyclohexylamine)(1-methyl-3-(cyclohexylmethyl)imidazol-2-ylidene)platinum(II);
  trans-dinitrato(N-cyclohexylamine)(1-methyl-3-(cyclohexylmethyl)imidazol-2-ylidene)platinum(II);
  trans-diiodo(N-cyclohexylamine)(1-methyl-3-phenylimidazol-2-ylidene)platinum(II);
  trans-dibromo(N-cyclohexylamine)(1-methyl-3-phenylimidazol-2-ylidene)platinum(II);
  trans-dichloro(N-cyclohexylamine)(1-methyl-3-phenylimidazol-2-ylidene)platinum(II);
  trans-dinitrato(N-cyclohexylamine)(1-methyl-3-phenylimidazol-2-ylidene)platinum(II);
  trans-diiodo(N-tetrahydropyranyl-4-amine)(1,3-dimethylimidazol-2-ylidene)platinum(II);
  trans-dibromo(N-tetrahydropyranyl-4-amine)(1,3-dimethylimidazol-2-ylidene)platinum(II);
  trans-dichloro(N-tetrahydropyranyl-4-amine)(1,3-dimethylimidazol-2-ylidene)platinum(II);
  trans-dinitrato(N-tetrahydropyranyl-4-amine)(1,3-dimethylimidazol-2-ylidene)platinum(II);
  trans-diiodo(N-tetrahydropyranyl-4-amine)(1,4-dimethyl-1,2,4-triazol-3-ylidene)platinum(II);
  trans-dibromo(N-tetrahydropyranyl-4-amine)(1,4-dimethyl-1,2,4-triazol-3-ylidene)platinum(II);
  trans-dichloro(N-tetrahydropyranyl-4-amine)(1,4-dimethyl-1,2,4-triazol-3-ylidene)platinum(II);
  trans-dinitrato(N-tetrahydropyranyl-4-amine)(1,4-dimethyl-1,2,4-triazol-3-ylidene)platinum(II);
  trans-diiodo(N-tetrahydropyranyl-4-amine)(1-methyl-3-(cyclohexylmethyl)imidazol-2-ylidene)platinum(II);
  trans-dibromo(N-tetrahydropyranyl-4-amine)(1-methyl-3-(cyclohexylmethyl)imidazol-2-ylidene)platinum(II);
  trans-dichloro(N-tetrahydropyranyl-4-amine)(1-methyl-3-(cyclohexylmethyl)imidazol-2-ylidene)platinum(II);
  trans-dinitrato(N-tetrahydropyranyl-4-amine)(1-methyl-3-(cyclohexylmethyl)imidazol-2-ylidene)platinum(II);
  trans-diiodo(N-tetrahydropyranyl-4-amine)(1-methyl-3-phenylimidazol-2-ylidene)platinum(II);
  trans-dibromo(N-tetrahydropyranyl-4-amine)(1-methyl-3-phenylimidazol-2-ylidene)platinum(II);
  trans-dichloro(N-tetrahydropyranyl-4-amine)(1-methyl-3-phenylimidazol-2-ylidene)platinum(II);
  trans-dinitrato(N-tetrahydropyranyl-4-amine)(1-methyl-3-phenylimidazol-2-ylidene)platinum(II);
  trans-diiodo(N-morpholine)(1,3-dimethylimidazol-2-ylidene)platinum(II);
  trans-dibromo(N-morpholine)(1,3-dimethylimidazol-2-ylidene)platinum(II);
  trans-dichloro(N-morpholine)(1,3-dimethylimidazol-2-ylidene)platinum(II);
  trans-dinitrato(N-morpholine)(1,3-dimethylimidazol-2-ylidene)platinum(II);
  trans-diiodo(N-morpholine)(1,4-dimethyl-1,2,4-triazol-3-ylidene)platinum(II);
  trans-dibromo(N-morpholine)(1,4-dimethyl-1,2,4-triazol-3-ylidene)platinum(II);
  trans-dichloro(N-4-amino-tetrahydropyran)(1,4-dimethyl-1,2,4-triazol-3-ylidene)platinum(II);
  trans-dinitrato(N-morpholine)(1,4-dimethyl-1,2,4-triazol-3-ylidene)platinum(II);
  trans-diiodo(N-morpholine)(1-methyl-3-(cyclohexylmethyl)imidazol-2-ylidene)platinum(II);
  trans-dibromo(N-morpholine)(1-methyl-3-(cyclohexylmethyl)imidazol-2-ylidene)platinum(II);
  trans-dichloro(N-morpholine)(1-methyl-3-(cyclohexylmethyl)imidazol-2-ylidene)platinum(II);
  trans-dinitrato(N-morpholine)(1-methyl-3-(cyclohexylmethyl)imidazol-2-ylidene)platinum(II);
  trans-diiodo(N-morpholine)(1-methyl-3-phenylimidazol-2-ylidene)platinum(II);
  trans-dibromo(N-morpholine)(1-methyl-3-phenylimidazol-2-ylidene)platinum(II);
  trans-dichloro(N-morpholine)(1-methyl-3-phenylimidazol-2-ylidene)platinum(II);

trans-dinitrato(N-morpholine)(1-methyl-3-phenylimidazol-2-ylidene)platinum(II);
trans-diiodo[N-(1-methylpiperidin-4-ylamine)](1,3-dimethylimidazol-2-ylidene)platinum(II);
trans-dibromo[N-(1-methylpiperidin-4-ylamine)](1,3-dimethylimidazol-2-ylidene)platinum(II);
trans-dichloro[N-(1-methylpiperidin-4-ylamine)](1,3-dimethylimidazol-2-ylidene)platinum(II);
trans-dinitrato[N-(1-methylpiperidin-4-ylamine)](1,3-dimethylimidazol-2-ylidene)platinum(II);
trans-diiodo[N-(1-methylpiperidin-4-ylamine)](1,4-dimethyl-1,2,4-triazol-3-ylidene)platinum(II);
trans-dibromo[N-(1-methylpiperidin-4-ylamine)](1,4-dimethyl-1,2,4-triazol-3-ylidene)platinum(II);
trans-dichloro[N-(1-methylpiperidin-4-ylamine)](1,4-dimethyl-1,2,4-triazol-3-ylidene)platinum(II);
trans-dinitrato[N-(1-methylpiperidin-4-ylamine)](1,4-dimethyl-1,2,4-triazol-3-ylidene)platinum(II);
trans-diiodo[N-(1-methylpiperidin-4-ylamine)](1-methyl-3-(cyclohexylmethyl)imidazol-2-ylidene)platinum(II);
trans-dibromo[N-(1-methylpiperidin-4-ylamine)](1-methyl-3-(cyclohexylmethyl)imidazol-2-ylidene)platinum(II);
trans-dichloro[N-(1-methylpiperidin-4-ylamine)](1-methyl-3-(cyclohexylmethyl)imidazol-2-ylidene)platinum(II);
trans-dinitrato[N-(1-methylpiperidin-4-ylamine)](1-methyl-3-(cyclohexylmethyl)-imidazol-2-ylidene)platinum(II);
trans-diiodo[N-(1-methylpiperidin-4-ylamine)](1-methyl-3-phenylimidazol-2-ylidene)platinum(II);
trans-dibromo[N-(1-methylpiperidin-4-ylamine)](1-methyl-3-phenylimidazol-2-ylidene)platinum(II);
trans-dichloro[N-(1-methylpiperidin-4-ylamine)](1-methyl-3-phenylimidazol-2-ylidene)platinum(II);
trans-dinitrato[N-(1-methylpiperidin-4-ylamine)] (1-methyl-3-phenylimidazol-2-ylidene)platinum(II);
trans-diiodo(N-exo(+/−)bicyclo[2.2.1]heptylamine)(1,3-dimethylimidazol-2-ylidene)platinum(II);
trans-dibromo(N-exo(+/−)bicyclo[2.2.1]heptylamine)(1,3-dimethylimidazol-2-ylidene)platinum(II);
trans-dichloro(N-exo(+/−)bicyclo[2.2.1]heptylamine)(1,3-dimethylimidazol-2-ylidene)platinum(II);
trans-dinitrato(N-exo(+/−)bicyclo[2.2.1]heptylamine)(1,3-dimethylimidazol-2-ylidene)platinum(II);
trans-diiodo(N-cyclohexylamine)(1,3-dimethylbenzimidazol-2-ylidene)platinum(II);
trans-dibromo(N-cyclohexylamine)(1,3-dimethylbenzimidazol-2-ylidene)platinum(II);
trans-dichloro(N-cyclohexylamine)(1,3-dimethylbenzimidazol-2-ylidene)platinum(II);
trans-dinitrato chloro(N-cyclohexylamine)(1,3-dimethylbenzimidazol-2-ylidene)platinum(II);
trans-diiodo(N-cyclohexylamine)(1,3,7,9-tetramethylxanthin-8-ylidene)platinum(II);
trans-dibromo(N-cyclohexylamine)(1,3,7,9-tetramethylxanthin-8-ylidene)platinum(II);
trans-dichloro(N-cyclohexylamine)(1,3,7,9-tetramethylxanthin-8-ylidene)platinum(II);
trans-dinitrato(N-cyclohexylamine)(1,3,7,9-tetramethylxanthin-8-ylidene)platinum(II);
trans-diiodo(N-cyclohexylamine)[1-methyl-3-(4-methoxybenzyl)imidazol-2-ylidene]platinum(II);
trans-dibromo(N-cyclohexylamine) [1-methyl-3-(4-methoxybenzyl)imidazol-2-ylidene]platinum(II);
trans-dichloro(N-cyclohexylamine)[1-methyl-3-(4-methoxybenzyl)imidazol-2-ylidene]platinum(II);
trans-dinitrato(N-cyclohexylamine) [1-methyl-3-(4-methoxybenzyl)imidazol-2-ylidene]platinum(II);
trans-diiodo(N-cyclohexylamine) [1-methyl-3-(4-trifluoromethylbenzyl)imidazol-2-ylidene]platinum(II);
trans-dibromo(N-cyclohexylamine) [1-methyl-3-(4-trifluoromethylbenzyl)imidazol-2-ylidene]platinum(II);
trans-dichloro(N-cyclohexylamine)[1-methyl-3-(4-trifluoromethylbenzyl)imidazol-2-ylidene]platinum(II);
trans-dinitrato(N-cyclohexylamine) [1-methyl-3-(4-trifluoromethylbenzyl)imidazol-2-ylidene]platinum(II);
trans-diiodo(N-cyclohexylamine) [1,3-dibenzylimidazol-2-ylidene]platinum(II);
trans-dibromo(N-cyclohexylamine) [1,3-dibenzylimidazol-2-ylidene]platinum(II);
trans-dichloro(N-cyclohexylamine) [1,3-dibenzylimidazol-2-ylidene]platinum(II);
trans-dinitrato(N-cyclohexylamine) [1,3-dibenzylimidazol-2-ylidene]platinum(II);
trans-diiodo(N-benzylamine)(1,3-dimethylimidazol-2-ylidene)platinum(II);
trans-dibromo(N-benzylamine)(1,3-dimethylimidazol-2-ylidene)platinum(II);
trans-dichloro(N-benzylamine)(1,3-dimethylimidazol-2-ylidene)platinum(II);
trans-dinitrato(N-benzylamine)(1,3-dimethylimidazol-2-ylidene)platinum(II);
trans-diiodo[N-4-(trifluoromethyl)benzylamine](1,3-dimethylimidazol-2-ylidene)platinum(II);
trans-dibromo[N-4-(trifluoromethyl)benzylamine](1,3-dimethylimidazol-2-ylidene)platinum(II);
trans-dichloro[N-4-(trifluoromethyl)benzylamine](1,3-dimethylimidazol-2-ylidene)platinum(II);
trans-dinitrato[N-4-(trifluoromethyl)benzylamine](1,3-dimethylimidazol-2-ylidene)platinum(II);
trans-diiodo(N-cyclohexylamine) [1-methyl-3-vinylimidazol-2-ylidene]platinum(II);
trans-dibromo(N-cyclohexylamine) [1-methyl-3-vinylimidazol-2-ylidene]platinum(II);
trans-dichloro(N-cyclohexylamine) [1-methyl-3-vinylimidazol-2-ylidene]platinum(II);
trans-dinitrato(N-cyclohexylamine) [1-methyl-3-vinylimidazol-2-ylidene]platinum(II);
trans-diiodo(N-exo(+)bicyclo[2.2.1]heptylamine)(1,3-dimethylbenzimidazol-2-ylidene)platinum(II);
trans-dibromo(N-exo(+)bicyclo[2.2.1]heptylamine)(1,3-dimethylbenzimidazol-2-ylidene)platinum(II);
trans-dichloro(N-exo(+)bicyclo[2.2.1]heptylamine)(1,3-dimethylbenzimidazol-2-ylidene)platinum(II);
trans-dinitrato(N-exo(+)bicyclo[2.2.1]heptylamine)(1,3-dimethylbenzimidazol-2-ylidene)platinum(II);
trans-diiodo(N-exo(−)bicyclo[2.2.1]heptylamine)(1,3-dimethylbenzimidazol-2-ylidene)platinum(II);
trans-dibromo(N-exo(−)bicyclo[2.2.1]heptylamine)(1,3-dimethylbenzimidazol-2-ylidene)platinum(II);
trans-dichloro(N-exo(−)bicyclo[2.2.1]heptylamine)(1,3-dimethylbenzimidazol-2-ylidene)platinum(II);
trans-dinitrato(N-exo(−)bicyclo[2.2.1]heptylamine)(1,3-dimethylbenzimidazol-2-ylidene)platinum(II);
trans-diiodo(N-cyclohexylamine)(1,3-dicyclohexylimidazol-2-ylidene)platinum(II);
trans-dibromo(N-cyclohexylamine)(1,3-dicyclohexylimidazol-2-ylidene)platinum(II);
trans-dichloro(N-cyclohexylamine)(1,3-dicyclohexylimidazol-2-ylidene)platinum(II);

trans-dinitrato(N-cyclohexylamine)(1,3-dicyclohexylimidazol-2-ylidene)platinum(II);
trans-diiodo(N-cyclohexylamine)(1-methyl-3-phenyl-1,2,4-triazol-3-ylidene)platinum(II);
trans-dibromo(N-cyclohexylamine)(1-methyl-3-phenyl-1,2,4-triazol-3-ylidene)platinum(II);
trans-dichloro(N-cyclohexylamine)(1-methyl-3-phenyl-1,2,4-triazol-3-ylidene)platinum(II);
trans-dinitrato(N-cyclohexylamine)(1-methyl-3-phenyl-1,2,4-triazol-3-ylidene)platinum(II);
trans-diiodo(N-cyclohexylamine) [1,3-dimethyl-4-phenylimidazol-2-ylidene]platinum(II);
trans-dibromo(N-cyclohexylamine) [1,3-dimethyl-4-phenylimidazol-2-ylidene]-platinum(II);
trans-dichloro(N-cyclohexylamine)[1,3-dimethyl-4-phenylimidazol-2-ylidene]-platinum(II);
trans-dinitrato(N-cyclohexylamine)[1,3-dimethyl-4-phenylimidazol-2-ylidene]-platinum(II);
trans-diiodo(N-cyclohexylamine)[3-benzyl-1-methyl-4-phenylimidazol-2-ylidene]-platinum(II);
trans-dibromo(N-cyclohexylamine)[3-benzyl-1-methyl-4-phenylimidazol-2-ylidene]-platinum(II);
trans-dichloro(N-cyclohexylamine)[3-benzyl-1-methyl-4-phenylimidazol-2-ylidene]-platinum(II);
trans-dinitrato(N-cyclohexylamine)[3-benzyl-1-methyl-4-phenylimidazol-2-ylidene]-platinum(II);
trans-diiodo(N-cyclohexylamine)[1,3-dimethyl-4,5-diphenylimidazol-2-ylidene]-platinum(II);
trans-dibromo(N-cyclohexylamine)[1,3-dimethyl-4,5-diphenylimidazol-2-ylidene]-platinum(II);
trans-dichloro(N-cyclohexylamine)[1,3-dimethyl-4,5-diphenylimidazol-2-ylidene]-platinum(II);
trans-dinitrato(N-cyclohexylamine)[1,3-dimethyl-4,5-diphenylimidazol-2-ylidene]-platinum(II);
trans-diiodo(N-exo(−)bicyclo[2.2.1]heptylamine)(1,3-dimethylimidazol-2-ylidene)platinum(II);
trans-dibromo(N-exo(−)bicyclo[2.2.1]heptylamine)(1,3-dimethylimidazol-2-ylidene)platinum(II);
trans-dichloro(N-exo(−)bicyclo[2.2.1]heptylamine)(1,3-dimethylimidazol-2-ylidene)platinum(II);
trans-dinitrato(N-exo(−)bicyclo[2.2.1]heptylamine)(1,3-dimethylimidazol-2-ylidene)platinum(II);
trans-diiodo(N-exo(+)bicyclo[2.2.1]heptylamine)(1,3-dimethylimidazol-2-ylidene)platinum(II);
trans-dibromo(N-exo(+)bicyclo[2.2.1]heptylamine)(1,3-dimethylimidazol-2-ylidene)platinum(II);
trans-dichloro(N-exo(+)bicyclo[2.2.1]heptylamine)(1,3-dimethylimidazol-2-ylidene)platinum(II);
trans-dinitrato(N-exo(+)bicyclo[2.2.1]heptylamine)(1,3-dimethylimidazol-2-ylidene)platinum(II);
trans-diiodo(N-exo(+/−)bicyclo[2.2.1]heptylamine)(1,3,7,9-tetramethylxanthin-8-ylidene)platinum(II);
trans-dibromo(N-exo(+/−)bicyclo[2.2.1]heptylamine)(1,3,7,9-tetramethylxanthin-8-ylidene)platinum(II);
trans-dichloro(N-exo(+/−)bicyclo[2.2.1]heptylamine)(1,3,7,9-tetramethylxanthin-8-ylidene)platinum(II);
trans-dinitrato(N-exo(+/−)bicyclo[2.2.1]heptylamine)(1,3,7,9-tetramethylxanthin-8-ylidene)platinum(II);
trans-diiodo(N-cyclopropylamine)(1,3-dimethylimidazol-2-ylidene)platinum(II);
trans-diiodo(N-cyclobutylamine)(1,3-dimethylimidazol-2-ylidene)platinum(II);
trans-diiodo(N-cyclopentylamine)(1,3-dimethylimidazol-2-ylidene)platinum(II);
trans-diiodo(N-cycloheptylamine)(1,3-dimethylimidazol-2-ylidene)platinum(II);
trans-diiodo(N-bicyclo[2.2.2]octylamine)(1,3-dimethylimidazol-2-ylidene)platinum(II);
trans-diiodo(N-endo(+/−)bicyclo[2.2.1]heptylamine)(1,3-dimethylimidazol-2-ylidene)platinum(II);
trans-diiodo(N-exo(+/−)bicyclo[3.2.1]octylamine)(1,3-dimethylimidazol-2-ylidene)platinum(II);
trans-diiodo(N-benzylamine)(1,3-dimethylimidazol-2-ylidene)platinum(II);
trans-diiodo(N-4-methoxybenzylamine)(1,3-dimethylimidazol-2-ylidene)platinum(II);
trans-diiodo(N-4-trifluoromethylbenzylamine)(1,3-dimethylimidazol-2-ylidene)platinum(II);
trans-diiodo(N-4-chlorobenzylamine)(1,3-dimethylimidazol-2-ylidene)platinum(II);
trans-diiodo(N-4-fluorobenzylamine)(1,3-dimethylimidazol-2-ylidene)platinum(II);
trans-diiodo(N-4-bromobenzylamine)(1,3-dimethylimidazol-2-ylidene)platinum(II);
trans-diiodo(N-4-methylbenzylamine)(1,3-dimethylimidazol-2-ylidene)platinum(II);
trans-diiodo(N-3,4-dichlorobenzylamine)(1,3-dimethylimidazol-2-ylidene)platinum(II);
trans-diiodo(N-3,4-dimethoxybenzylamine)(1,3-dimethylimidazol-2-ylidene)platinum(II);
trans-diiodo(N-3,4-dimethylbenzylamine)(1,3-dimethylimidazol-2-ylidene)platinum(II);
trans-diiodo(N-cyclopropylamine)(1,4-dimethyl-1,2,4-triazol-3-ylidene)platinum(II);
trans-diiodo(N-cyclobutylamine)(1,4-dimethyl-1,2,4-triazol-3-ylidene)platinum(II);
trans-diiodo(N-cyclopentylamine)(1,4-dimethyl-1,2,4-triazol-3-ylidene)platinum(II);
trans-diiodo(N-cycloheptylamine)(1,4-dimethyl-1,2,4-triazol-3-ylidene)platinum(II);
trans-diiodo(N-bicyclo[2.2.2]octylamine)(1,4-dimethyl-1,2,4-triazol-3-ylidene)platinum(II);
trans-diiodo(N-endo(+/−)bicyclo[2.2.1]heptylamine)(1,4-dimethyl-1,2,4-triazol-3-ylidene)platinum(II);
trans-diiodo(N-exo(+/−)bicyclo[3.2.1]octylamine)(1,4-dimethyl-1,2,4-triazol-3-ylidene)platinum(II);
trans-diiodo(N-benzylamine)(1,4-dimethyl-1,2,4-triazol-3-ylidene)platinum(II);
trans-diiodo(N-4-methoxybenzylamine)(1,4-dimethyl-1,2,4-triazol-3-ylidene)platinum(II);
trans-diiodo(N-4-trifluoromethylbenzylamine)(1,4-dimethyl-1,2,4-triazol-3-ylidene)platinum(II);
trans-diiodo(N-4-chlorobenzylamine)(1,4-dimethyl-1,2,4-triazol-3-ylidene)platinum(II);
trans-diiodo(N-4-fluorobenzylamine)(1,4-dimethyl-1,2,4-triazol-3-ylidene)platinum(II);
trans-diiodo(N-4-bromobenzylamine)(1,4-dimethyl-1,2,4-triazol-3-ylidene)platinum(II);
trans-diiodo(N-4-methylbenzylamine)(1,4-dimethyl-1,2,4-triazol-3-ylidene)platinum(II);
trans-diiodo(N-3,4-dichlorobenzylamine)(1,4-dimethyl-1,2,4-triazol-3-ylidene)platinum(II);
trans-diiodo(N-3,4-dimethoxybenzylamine)(1,4-dimethyl-1,2,4-triazol-3-ylidene)platinum(II);
trans-diiodo(N-3,4-dimethylbenzylamine)(1,4-dimethyl-1,2,4-triazol-3-ylidene)platinum(II);
trans-diiodo(N-cyclopropylamine)(1-methyl-3-(cyclohexylmethyl)imidazol-2-ylidene)platinum(II);
trans-diiodo(N-cyclobutylamine)(1-methyl-3-(cyclohexylmethyl)imidazol-2-ylidene)platinum(II);
trans-diiodo(N-cyclopentylamine)(1-methyl-3-(cyclohexylmethyl)imidazol-2-ylidene)platinum(II);

trans-diiodo(N-cycloheptylamine)(1-methyl-3-(cyclohexylmethyl)imidazol-2-ylidene)platinum(II);
trans-diiodo(N-bicyclo[2.2.2]octylamine)(1-methyl-3-(cyclohexylmethyl)imidazol-2-ylidene)platinum(II);
trans-diiodo(N-endo(+/−)bicyclo[2.2.1]heptylamine)(1-methyl-3-(cyclohexylmethyl)imidazol-2-ylidene)platinum(II);
trans-diiodo(N-exo(+/−)bicyclo[3.2.1]octylamine)(1-methyl-3-(cyclohexylmethyl)imidazol-2-ylidene)platinum(II);
trans-diiodo(N-benzylamine)(1-methyl-3-(cyclohexylmethyl)imidazol-2-ylidene)platinum(II);
trans-diiodo(N-4-methoxybenzylamine)(1-methyl-3-(cyclohexylmethyl)imidazol-2-ylidene)platinum(II);
trans-diiodo(N-4-trifluoromethylbenzylamine)(1-methyl-3-(cyclohexylmethyl)imidazol-2-ylidene)platinum(II);
trans-diiodo(N-4-chlorobenzylamine)(1-methyl-3-(cyclohexylmethyl)imidazol-2-ylidene)platinum(II);
trans-diiodo(N-4-fluorobenzylamine)(1-methyl-3-(cyclohexylmethyl)imidazol-2-ylidene)platinum(II);
trans-diiodo(N-4-bromobenzylamine)(1-methyl-3-(cyclohexylmethyl)imidazol-2-ylidene)platinum(II);
trans-diiodo(N-4-methylbenzylamine)(1-methyl-3-(cyclohexylmethyl)imidazol-2-ylidene)platinum(II);
trans-diiodo(N-3,4-dichlorobenzylamine)(1-methyl-3-(cyclohexylmethyl)imidazol-2-ylidene)platinum(II);
trans-diiodo(N-3,4-dimethoxybenzylamine)(1-methyl-3-(cyclohexylmethyl)imidazol-2-ylidene)platinum(II);
trans-diiodo(N-3,4-dimethylbenzylamine)(1-methyl-3-(cyclohexylmethyl)imidazol-2-ylidene)platinum(II);
trans-diiodo(N-cyclopropylamine)(1-methyl-3-phenylimidazol-2-ylidene)platinum(II);
trans-diiodo(N-cyclobutylamine)(1-methyl-3-phenylimidazol-2-ylidene)platinum(II);
trans-diiodo(N-cyclopentylamine)(1-methyl-3-phenylimidazol-2-ylidene)platinum(II);
trans-diiodo(N-cycloheptylamine)(1-methyl-3-phenylimidazol-2-ylidene)platinum(II);
trans-diiodo(N-bicyclo[2.2.2]octylamine)(1-methyl-3-phenylimidazol-2-ylidene)platinum(II);
trans-diiodo(N-endo(+/−)bicyclo[2.2.1]heptylamine)(1-methyl-3-phenylimidazol-2-ylidene)platinum(II);
trans-diiodo(N-exo(+/−)bicyclo[3.2.1]octylamine)(1-methyl-3-phenylimidazol-2-ylidene)platinum(II);
trans-diiodo(N-benzylamine)(1-methyl-3-phenylimidazol-2-ylidene)platinum(II);
trans-diiodo(N-4-methoxybenzylamine)(1-methyl-3-phenylimidazol-2-ylidene)platinum(II);
trans-diiodo(N-4-trifluoromethylbenzylamine)(1-methyl-3-phenylimidazol-2-ylidene)platinum(II);
trans-diiodo(N-4-chlorobenzylamine)(1-methyl-3-phenylimidazol-2-ylidene)platinum(II);
trans-diiodo(N-4-fluorobenzylamine)(1-methyl-3-phenylimidazol-2-ylidene)platinum(II);
trans-diiodo(N-4-bromobenzylamine)(1-methyl-3-phenylimidazol-2-ylidene)platinum(II);
trans-diiodo(N-4-methylbenzylamine)(1-methyl-3-phenylimidazol-2-ylidene)platinum(II);
trans-diiodo(N-3,4-dichlorobenzylamine)(1-methyl-3-phenylimidazol-2-ylidene)platinum(II);
trans-diiodo(N-3,4-dimethoxybenzylamine)(1-methyl-3-phenylimidazol-2-ylidene)platinum(II);
trans-diiodo(N-3,4-dimethylbenzylamine)(1-methyl-3-phenylimidazol-2-ylidene)platinum(II);
trans-diiodo(N-cyclopropylamine)(1,3-dimethylbenzimidazol-2-ylidene)platinum(II);
trans-diiodo(N-cyclobutylamine)(1,3-dimethylbenzimidazol-2-ylidene)platinum(II);
trans-diiodo(N-cyclopentylamine)(1,3-dimethylbenzimidazol-2-ylidene)platinum(II);
trans-diiodo(N-cycloheptylamine)(1,3-dimethylbenzimidazol-2-ylidene)platinum(II);
trans-diiodo(N-bicyclo[2.2.2]octylamine)(1,3-dimethylbenzimidazol-2-ylidene)platinum(II);
trans-diiodo(N-endo(+/−)bicyclo[2.2.1]heptylamine)(1,3-dimethylbenzimidazol-2-ylidene)platinum(II);
trans-diiodo(N-exo(+/−)bicyclo[3.2.1]octylamine)(1,3-dimethylbenzimidazol-2-ylidene)platinum(II);
trans-diiodo(N-benzylamine)(1,3-dimethylbenzimidazol-2-ylidene)platinum(II);
trans-diiodo(N-4-methoxybenzylamine)(1,3-dimethylbenzimidazol-2-ylidene)platinum(II);
trans-diiodo(N-4-trifluoromethylbenzylamine)(1,3-dimethylbenzimidazol-2-ylidene)platinum(II);
trans-diiodo(N-4-chlorobenzylamine)(1,3-dimethylbenzimidazol-2-ylidene)platinum(II);
trans-diiodo(N-4-fluorobenzylamine)(1,3-dimethylbenzimidazol-2-ylidene)platinum(II);
trans-diiodo(N-4-bromobenzylamine)(1,3-dimethylbenzimidazol-2-ylidene)platinum(II);
trans-diiodo(N-4-methylbenzylamine)(1,3-dimethylbenzimidazol-2-ylidene)platinum(II);
trans-diiodo(N-3,4-dichlorobenzylamine)(1,3-dimethylbenzimidazol-2-ylidene)platinum(II);
trans-diiodo(N-3,4-dimethoxybenzylamine)(1,3-dimethylbenzimidazol-2-ylidene)platinum(II);
trans-diiodo(N-3,4-dimethylbenzylamine)(1,3-dimethylbenzimidazol-2-ylidene)platinum(II);
trans-diiodo(N-cyclopropylamine)(1,3,7,9-tetramethylxanthin-8-ylidene)platinum(II);
trans-diiodo(N-cyclobutylamine)(1,3,7,9-tetramethylxanthin-8-ylidene)platinum(II);
trans-diiodo(N-cyclopentylamine)(1,3,7,9-tetramethylxanthin-8-ylidene)platinum(II);
trans-diiodo(N-cycloheptylamine)(1,3,7,9-tetramethylxanthin-8-ylidene)platinum(II);
trans-diiodo(N-bicyclo[2.2.2]octylamine)(1,3,7,9-tetramethylxanthin-8-ylidene)platinum(II);
trans-diiodo(N-endo(+/−)bicyclo[2.2.1]heptylamine)(1,3,7,9-tetramethylxanthin-8-ylidene)platinum(II);
trans-diiodo(N-exo(+/−)bicyclo[3.2.1]octylamine)(1,3,7,9-tetramethylxanthin-8-ylidene)platinum(II);
trans-diiodo(N-benzylamine)(1,3,7,9-tetramethylxanthin-8-ylidene)platinum(II);
trans-diiodo(N-4-methoxybenzylamine)(1,3,7,9-tetramethylxanthin-8-ylidene)platinum(II);
trans-diiodo(N-4-trifluoromethylbenzylamine)(1,3,7,9-tetramethylxanthin-8-ylidene)platinum(II);
trans-diiodo(N-4-chlorobenzylamine)(1,3,7,9-tetramethylxanthin-8-ylidene)platinum(II);
trans-diiodo(N-4-fluorobenzylamine)(1,3,7,9-tetramethylxanthin-8-ylidene)platinum(II);
trans-diiodo(N-4-bromobenzylamine)(1,3,7,9-tetramethylxanthin-8-ylidene)platinum(II);
trans-diiodo(N-4-methylbenzylamine)(1,3,7,9-tetramethylxanthin-8-ylidene)platinum(II);
trans-diiodo(N-3,4-dichlorobenzylamine)(1,3,7,9-tetramethylxanthin-8-ylidene)platinum(II);
trans-diiodo(N-3,4-dimethoxybenzylamine)(1,3,7,9-tetramethylxanthin-8-ylidene)platinum(II);
trans-diiodo(N-3,4-dimethylbenzylamine)(1,3,7,9-tetramethylxanthin-8-ylidene)platinum(II);

trans-diiodo(N-cyclopropylamine)[1-methyl-3-(4-methoxybenzyl)imidazol-2-ylidene]platinum(II);
trans-diiodo(N-cyclobutylamine)[1-methyl-3-(4-methoxybenzyl)imidazol-2-ylidene]-platinum(II);
trans-diiodo(N-cyclopentylamine)[1-methyl-3-(4-methoxybenzyl)imidazol-2-ylidene]platinum(II);
trans-diiodo(N-cycloheptylamine)[1-methyl-3-(4-methoxybenzyl)imidazol-2-ylidene]platinum(II);
trans-diiodo(N-bicyclo[2.2.2]octylamine)[1-methyl-3-(4-methoxybenzyl)imidazol-2-ylidene]platinum(II);
trans-diiodo(N-endo(+/−)bicyclo[2.2.1]heptylamine)[1-methyl-3-(4-methoxybenzyl)imidazol-2-ylidene]platinum(II);
trans-diiodo(N-exo(+/−)bicyclo[3.2.1]octylamine)[1-methyl-3-(4-methoxybenzyl)imidazol-2-ylidene]platinum(II);
trans-diiodo(N-benzylamine)[1-methyl-3-(4-methoxybenzyl)imidazol-2-ylidene]-platinum(II);
trans-diiodo(N-4-methoxybenzylamine)[1-methyl-3-(4-methoxybenzyl)imidazol-2-ylidene]platinum(II);
trans-diiodo(N-4-trifluoromethylbenzylamine)[1-methyl-3-(4-methoxybenzyl)imidazol-2-ylidene]platinum(II);
trans-diiodo(N-4-chlorobenzylamine)[1-methyl-3-(4-methoxybenzyl)imidazol-2-ylidene]platinum(II);
trans-diiodo(N-4-fluorobenzylamine)[1-methyl-3-(4-methoxybenzyl)imidazol-2-ylidene]platinum(II);
trans-diiodo(N-4-bromobenzylamine)[1-methyl-3-(4-methoxybenzyl)imidazol-2-ylidene]platinum(II);
trans-diiodo(N-4-methylbenzylamine)[1-methyl-3-(4-methoxybenzyl)imidazol-2-ylidene]platinum(II);
trans-diiodo(N-3,4-dichlorobenzylamine)[1-methyl-3-(4-methoxybenzyl)imidazol-2-ylidene]platinum(II);
trans-diiodo(N-3,4-dimethoxybenzylamine)[1-methyl-3-(4-methoxybenzyl)imidazol-2-ylidene]platinum(II);
trans-diiodo(N-3,4-dimethylbenzylamine)[1-methyl-3-(4-methoxybenzyl)imidazol-2-ylidene]platinum(II);
trans-diiodo(N-cyclopropylamine)[1-methyl-3-(4-trifluoromethylbenzyl)imidazol-2-ylidene]platinum(II);
trans-diiodo(N-cyclobutylamine)[1-methyl-3-(4-trifluoromethylbenzyl)imidazol-2-ylidene]platinum(II);
trans-diiodo(N-cyclopentylamine)[1-methyl-3-(4-trifluoromethylbenzyl)imidazol-2-ylidene]platinum(II);
trans-diiodo(N-cycloheptylamine)[1-methyl-3-(4-trifluoromethylbenzyl)imidazol-2-ylidene]platinum(II);
trans-diiodo(N-bicyclo[2.2.2]octylamine)[1-methyl-3-(4-trifluoromethylbenzyl)imidazol-2-ylidene]platinum(II);
trans-diiodo(N-endo(+/−)bicyclo[2.2.1]heptylamine)[1-methyl-3-(4-trifluoromethylbenzyl)imidazol-2-ylidene]platinum(II);
trans-diiodo(N-exo(+/−)bicyclo[3.2.1]octylamine)[1-methyl-3-(4-trifluoromethylbenzyl)imidazol-2-ylidene]platinum(II);
trans-diiodo(N-benzylamine)[1-methyl-3-(4-trifluoromethylbenzyl)imidazol-2-ylidene]platinum(II);
trans-diiodo(N-4-methoxybenzylamine)[1-methyl-3-(4-trifluoromethylbenzyl)imidazol-2-ylidene]platinum(II);
trans-diiodo(N-4-trifluoromethylbenzylamine)[1-methyl-3-(4-trifluoromethylbenzyl)imidazol-2-ylidene]platinum(II);
trans-diiodo(N-4-chlorobenzylamine)[1-methyl-3-(4-trifluoromethylbenzyl)imidazol-2-ylidene]platinum(II);
trans-diiodo(N-4-fluorobenzylamine)[1-methyl-3-(4-trifluoromethylbenzyl)imidazol-2-ylidene]platinum(II);
trans-diiodo(N-4-bromobenzylamine)[1-methyl-3-(4-trifluoromethylbenzyl)imidazol-2-ylidene]platinum(II);
trans-diiodo(N-4-methylbenzylamine)[1-methyl-3-(4-trifluoromethylbenzyl)imidazol-2-ylidene]platinum(II);
trans-diiodo(N-3,4-dichlorobenzylamine)[1-methyl-3-(4-trifluoromethylbenzyl)imidazol-2-ylidene]platinum(II);
trans-diiodo(N-3,4-dimethoxybenzylamine)[1-methyl-3-(4-trifluoromethylbenzyl)imidazol-2-ylidene]platinum(II);
trans-diiodo(N-3,4-dimethylbenzylamine)[1-methyl-3-(4-trifluoromethylbenzyl)imidazol-2-ylidene]platinum(II);
trans-diiodo(N-cyclopropylamine)[1-methyl-3-(3-methoxybenzyl)imidazol-2-ylidene]platinum(II);
trans-diiodo(N-cyclobutylamine)[1-methyl-3-(3-methoxybenzyl)imidazol-2-ylidene]-platinum(II);
trans-diiodo(N-cyclopentylamine)[1-methyl-3-(3-methoxybenzyl)imidazol-2-ylidene]-platinum(II);
trans-diiodo(N-cycloheptylamine)[1-methyl-3-(3-methoxybenzyl)imidazol-2-ylidene]platinum(II);
trans-diiodo(N-bicyclo[2.2.2]octylamine)[1-methyl-3-(3-methoxybenzyl)imidazol-2-ylidene]platinum(II);
trans-diiodo(N-endo(+/−)bicyclo[2.2.1]heptylamine)[1-methyl-3-(3-methoxybenzyl)imidazol-2-ylidene]platinum(II);
trans-diiodo(N-exo(+/−)bicyclo[3.2.1]octylamine)[1-methyl-3-(3-methoxybenzyl)imidazol-2-ylidene]platinum(II);
trans-diiodo(N-benzylamine)[1-methyl-3-(3-methoxybenzyl)imidazol-2-ylidene]-platinum(II);
trans-diiodo(N-4-methoxybenzylamine)[1-methyl-3-(3-methoxybenzyl)imidazol-2-ylidene]platinum(II);
trans-diiodo(N-4-trifluoromethylbenzylamine) [1-methyl-3-(3-methoxybenzyl)imidazol-2-ylidene]platinum(II);
trans-diiodo(N-4-chlorobenzylamine)[1-methyl-3-(3-methoxybenzyl)imidazol-2-ylidene]platinum(II);
trans-diiodo(N-4-fluorobenzylamine)[1-methyl-3-(3-methoxybenzyl)imidazol-2-ylidene]platinum(II);
trans-diiodo(N-4-bromobenzylamine)[1-methyl-3-(3-methoxybenzyl)imidazol-2-ylidene]platinum(II);
trans-diiodo(N-4-methylbenzylamine)[1-methyl-3-(3-methoxybenzyl)imidazol-2-ylidene]platinum(II);
trans-diiodo(N-3,4-dichlorobenzylamine)[1-methyl-3-(3-methoxybenzyl)imidazol-2-ylidene]platinum(II);
trans-diiodo(N-3,4-dimethoxybenzylamine)[1-methyl-3-(3-methoxybenzyl)imidazol-2-ylidene]platinum(II);
trans-diiodo(N-3,4-dimethylbenzylamine)[1-methyl-3-(3-methoxybenzyl)imidazol-2-ylidene]platinum(II);
trans-diiodo(N-cyclopropylamine)[1-methyl-3-(3-trifluoromethylbenzyl)imidazol-2-ylidene]platinum(II);
trans-diiodo(N-cyclobutylamine)[1-methyl-3-(3-trifluoromethylbenzyl)imidazol-2-ylidene]platinum(II);
trans-diiodo(N-cyclopentylamine)[1-methyl-3-(3-trifluoromethylbenzyl)imidazol-2-ylidene]platinum(II);
trans-diiodo(N-cycloheptylamine)[1-methyl-3-(3-trifluoromethylbenzyl)imidazol-2-ylidene]platinum(II);
trans-diiodo(N-bicyclo[2.2.2]octylamine)[1-methyl-3-(3-trifluoromethylbenzyl)imidazol-2-ylidene]platinum(II);
trans-diiodo(N-endo(+/−)bicyclo[2.2.1]heptylamine)[1-methyl-3-(3-trifluoromethylbenzyl)imidazol-2-ylidene]platinum(II);
trans-diiodo(N-exo(+/−)bicyclo[3.2.1]octylamine)[1-methyl-3-(3-trifluoromethylbenzyl)imidazol-2-ylidene]platinum(II);
trans-diiodo(N-benzylamine)[1-methyl-3-(3-trifluoromethylbenzyl)imidazol-2-ylidene]platinum(II);

trans-diiodo(N-4-methoxybenzylamine) [1-methyl-3-(3-trifluoromethylbenzyl)imidazol-2-ylidene]platinum(II);
trans-diiodo(N-4-trifluoromethylbenzylamine)[1-methyl-3-(3-trifluoromethylbenzyl)imidazol-2-ylidene]platinum(II);
trans-diiodo(N-4-chlorobenzylamine)[1-methyl-3-(3-trifluoromethylbenzyl)imidazol-2-ylidene]platinum(II);
trans-diiodo(N-4-fluorobenzylamine)[1-methyl-3-(3-trifluoromethylbenzyl)imidazol-2-ylidene]platinum(II);
trans-diiodo(N-4-bromobenzylamine)[1-methyl-3-(3-trifluoromethylbenzyl)imidazol-2-ylidene]platinum(II);
trans-diiodo(N-4-methylbenzylamine)[1-methyl-3-(3-trifluoromethylbenzyl)imidazol-2-ylidene]platinum(II);
trans-diiodo(N-3,4-dichlorobenzylamine)[1-methyl-3-(3-trifluoromethylbenzyl)imidazol-2-ylidene]platinum(II);
trans-diiodo(N-3,4-dimethoxybenzylamine) [1-methyl-3-(3-trifluoromethylbenzyl)imidazol-2-ylidene]platinum(II);
trans-diiodo(N-3,4-dimethylbenzylamine) [1-methyl-3-(3-trifluoromethylbenzyl)imidazol-2-ylidene]platinum(II);
trans-diiodo(N-cyclopropylamine) [1-methyl-3-(3,4-dimethoxybenzyl)imidazol-2-ylidene]platinum(II);
trans-diiodo(N-cyclobutylamine) [1-methyl-3-(3,4-dimethoxybenzyl)imidazol-2-ylidene]platinum(II);
trans-diiodo(N-cyclopentylamine) [1-methyl-3-(3,4-dimethoxybenzyl)imidazol-2-ylidene]platinum(II);
trans-diiodo(N-cycloheptylamine) [1-methyl-3-(3,4-dimethoxybenzyl)imidazol-2-ylidene]platinum(II);
trans-diiodo(N-bicyclo[2.2.2]octylamine)[1-methyl-3-(3,4-dimethoxybenzyl)imidazol-2-ylidene]platinum(II);
trans-diiodo(N-endo(+/−)bicyclo[2.2.1]heptylamine) [1-methyl-3-(3,4-dimethoxybenzyl)imidazol-2-ylidene]platinum(II);
trans-diiodo(N-exo(+/−)bicyclo[3.2.1]octylamine)[1-methyl-3-(3,4-dimethoxybenzyl)imidazol-2-ylidene]platinum(II);
trans-diiodo(N-benzylamine) [1-methyl-3-(3,4-dimethoxybenzyl)imidazol-2-ylidene]platinum(II);
trans-diiodo(N-4-methoxybenzylamine) [1-methyl-3-(3,4-dimethoxybenzyl)imidazol-2-ylidene]platinum(II);
trans-diiodo(N-4-trifluoromethylbenzylamine)[1-methyl-3-(3,4-dimethoxybenzyl)imidazol-2-ylidene]platinum(II);
trans-diiodo(N-4-chlorobenzylamine) [1-methyl-3-(3,4-dimethoxybenzyl)imidazol-2-ylidene]platinum(II);
trans-diiodo(N-4-fluorobenzylamine) [1-methyl-3-(3,4-dimethoxybenzyl)imidazol-2-ylidene]platinum(II);
trans-diiodo(N-4-bromobenzylamine) [1-methyl-3-(3,4-dimethoxybenzyl)imidazol-2-ylidene]platinum(II);
trans-diiodo(N-4-methylbenzylamine)[1-methyl-3-(3,4-dimethoxybenzyl)imidazol-2-ylidene]platinum(II);
trans-diiodo(N-3,4-dichlorobenzylamine)[1-methyl-3-(3,4-dimethoxybenzyl)imidazol-2-ylidene]platinum(II);
trans-diiodo(N-3,4-dimethoxybenzylamine) [1-methyl-3-(3,4-dimethoxybenzyl)imidazol-2-ylidene]platinum(II);
trans-diiodo(N-3,4-dimethylbenzylamine)[1-methyl-3-(3,4-dimethoxybenzyl)imidazol-2-ylidene]platinum(II);
trans-diiodo(N-cyclopropylamine)(1,3-dibenzylimidazol-2-ylidene)platinum(II);
trans-diiodo(N-cyclobutylamine)(1,3-dibenzylimidazol-2-ylidene)platinum(II);
trans-diiodo(N-cyclopentylamine)(1,3-dibenzylimidazol-2-ylidene)platinum(II);
trans-diiodo(N-cycloheptylamine)(1,3-dibenzylimidazol-2-ylidene)platinum(II);
trans-diiodo(N-bicyclo[2.2.2]octylamine)(1,3-dibenzylimidazol-2-ylidene)platinum(II);
trans-diiodo(N-endo(+/−)bicyclo[2.2.1]heptylamine)(1,3-dibenzylimidazol-2-ylidene)platinum(II);
trans-diiodo(N-exo(+/−)bicyclo[3.2.1]octylamine)(1,3-dibenzylimidazol-2-ylidene)platinum(II);
trans-diiodo(N-benzylamine)(1,3-dibenzylimidazol-2-ylidene)platinum(II);
trans-diiodo(N-4-methoxybenzylamine)(1,3-dibenzylimidazol-2-ylidene)platinum(II);
trans-diiodo(N-4-trifluoromethylbenzylamine)(1,3-dibenzylimidazol-2-ylidene)platinum(II);
trans-diiodo(N-4-chlorobenzylamine)(1,3-dibenzylimidazol-2-ylidene)platinum(II);
trans-diiodo(N-4-fluorobenzylamine)(1,3-dibenzylimidazol-2-ylidene)platinum(II);
trans-diiodo(N-4-bromobenzylamine)(1,3-dibenzylimidazol-2-ylidene)platinum(II);
trans-diiodo(N-4-methylbenzylamine)(1,3-dibenzylimidazol-2-ylidene)platinum(II);
trans-diiodo(N-3,4-dichlorobenzylamine)(1,3-dibenzylimidazol-2-ylidene)platinum(II);
trans-diiodo(N-3,4-dimethoxybenzylamine)(1,3-dibenzylimidazol-2-ylidene)platinum(II);
trans-diiodo(N-3,4-dimethylbenzylamine)(1,3-dibenzylimidazol-2-ylidene)platinum(II);
trans-diiodo(N-cyclopropylamine)(1-methyl-3-vinylimidazol-2-ylidene)platinum(II);
trans-diiodo(N-cyclobutylamine)(1-methyl-3-vinylimidazol-2-ylidene)platinum(II);
trans-diiodo(N-cyclopentylamine)(1-methyl-3-vinylimidazol-2-ylidene)platinum(II);
trans-diiodo(N-cycloheptylamine)(1-methyl-3-vinylimidazol-2-ylidene)platinum(II);
trans-diiodo(N-bicyclo[2.2.2]octylamine)(1-methyl-3-vinylimidazol-2-ylidene)platinum(II);
trans-diiodo(N-endo(+/−)bicyclo[2.2.1]heptylamine)(1-methyl-3-vinylimidazol-2-ylidene)platinum(II);
trans-diiodo(N-exo(+/−)bicyclo[3.2.1]octylamine)(1-methyl-3-vinylimidazol-2-ylidene)platinum(II);
trans-diiodo(N-benzylamine)(1-methyl-3-vinylimidazol-2-ylidene)platinum(II);
trans-diiodo(N-4-methoxybenzylamine)(1-methyl-3-vinylimidazol-2-ylidene)platinum(II);
trans-diiodo(N-4-trifluoromethylbenzylamine)(1-methyl-3-vinylimidazol-2-ylidene)platinum(II);
trans-diiodo(N-4-chlorobenzylamine)(1-methyl-3-vinylimidazol-2-ylidene)platinum(II);
trans-diiodo(N-4-fluorobenzylamine)(1-methyl-3-vinylimidazol-2-ylidene)platinum(II);
trans-diiodo(N-4-bromobenzylamine)(1-methyl-3-vinylimidazol-2-ylidene)platinum(II);
trans-diiodo(N-4-methylbenzylamine)(1-methyl-3-vinylimidazol-2-ylidene)platinum(II);
trans-diiodo(N-3,4-dichlorobenzylamine)(1-methyl-3-vinylimidazol-2-ylidene)platinum(II);
trans-diiodo(N-3,4-dimethoxybenzylamine)(1-methyl-3-vinylimidazol-2-ylidene)platinum(II);
trans-diiodo(N-3,4-dimethylbenzylamine)(1-methyl-3-vinylimidazol-2-ylidene)platinum(II);
trans-diiodo(N-cyclopropylamine)(1-methyl-3-ethylimidazol-2-ylidene)platinum(II);
trans-diiodo(N-cyclobutylamine)(1-methyl-3-ethylimidazol-2-ylidene)platinum(II);

trans-diiodo(N-cyclopentylamine)(1-methyl-3-ethylimidazol-2-ylidene)platinum(II);
trans-diiodo(N-cycloheptylamine)(1-methyl-3-ethylimidazol-2-ylidene)platinum(II);
trans-diiodo(N-bicyclo[2.2.2]octylamine)(1-methyl-3-ethylimidazol-2-ylidene)platinum(II);
trans-diiodo(N-endo(+/−)bicyclo[2.2.1]heptylamine)(1-methyl-3-ethylimidazol-2-ylidene)platinum(II);
trans-diiodo(N-exo(+/−)bicyclo[3.2.1]octylamine)(1-methyl-3-ethylimidazol-2-ylidene)platinum(II);
trans-diiodo(N-benzylamine)(1-methyl-3-ethylimidazol-2-ylidene)platinum(II);
trans-diiodo(N-4-methoxybenzylamine)(1-methyl-3-ethylimidazol-2-ylidene)platinum(II);
trans-diiodo(N-4-trifluoromethylbenzylamine)(1-methyl-3-ethylimidazol-2-ylidene)platinum(II);
trans-diiodo(N-4-chlorobenzylamine)(1-methyl-3-ethylimidazol-2-ylidene)platinum(II);
trans-diiodo(N-4-fluorobenzylamine)(1-methyl-3-ethylimidazol-2-ylidene)platinum(II);
trans-diiodo(N-4-bromobenzylamine)(1-methyl-3-ethylimidazol-2-ylidene)platinum(II);
trans-diiodo(N-4-methylbenzylamine)(1-methyl-3-ethylimidazol-2-ylidene)platinum(II);
trans-diiodo(N-3,4-dichlorobenzylamine)(1-methyl-3-ethylimidazol-2-ylidene)platinum(II);
trans-diiodo(N-3,4-dimethoxybenzylamine)(1-methyl-3-ethylimidazol-2-ylidene)platinum(II);
trans-diiodo(N-3,4-dimethylbenzylamine)(1-methyl-3-ethylimidazol-2-ylidene)platinum(II);
trans-diiodo(N-cyclopropylamine)(1-methyl-3-isopropyl-2-ylidene)platinum(II);
trans-diiodo(N-cyclobutylamine)(1-methyl-3-isopropylimidazol-2-ylidene)platinum(II);
trans-diiodo(N-cyclopentylamine)(1-methyl-3-isopropylimidazol-2-ylidene)platinum(II);
trans-diiodo(N-cycloheptylamine)(1-methyl-3-isopropylimidazol-2-ylidene)platinum(II);
trans-diiodo(N-bicyclo[2.2.2]octylamine)(1-methyl-3-isopropylimidazol-2-ylidene)platinum(II);
trans-diiodo(N-endo(+/−)bicyclo[2.2.1]heptylamine)(1-methyl-3-isopropylimidazol-2-ylidene)platinum(II);
trans-diiodo(N-exo(+/−)bicyclo[3.2.1]octylamine)(1-methyl-3-isopropylimidazol-2-ylidene)platinum(II);
trans-diiodo(N-benzylamine)(1-methyl-3-isopropylimidazol-2-ylidene)platinum(II);
trans-diiodo(N-4-methoxybenzylamine)(1-methyl-3-isopropylimidazol-2-ylidene)platinum(II);
trans-diiodo(N-4-trifluoromethylbenzylamine)(1-methyl-3-isopropylimidazol-2-ylidene)platinum(II);
trans-diiodo(N-4-chlorobenzylamine)(1-methyl-3-isopropylimidazol-2-ylidene)platinum(II);
trans-diiodo(N-4-fluorobenzylamine)(1-methyl-3-isopropylimidazol-2-ylidene)platinum(II);
trans-diiodo(N-4-bromobenzylamine)(1-methyl-3-isopropylimidazol-2-ylidene)platinum(II);
trans-diiodo(N-4-methylbenzylamine)(1-methyl-3-isopropylimidazol-2-ylidene)platinum(II);
trans-diiodo(N-3,4-dichlorobenzylamine)(1-methyl-3-isopropylimidazol-2-ylidene)platinum(II);
trans-diiodo(N-3,4-dimethoxybenzylamine)(1-methyl-3-isopropylimidazol-2-ylidene)platinum(II);
trans-diiodo(N-3,4-dimethylbenzylamine)(1-methyl-3-isopropylimidazol-2-ylidene)platinum(II);
trans-diiodo(N-cyclopropylamine)(1-methyl-3-allylimidazol-2-ylidene)platinum(II);
trans-diiodo(N-cyclobutylamine)(1-methyl-3-allylimidazol-2-ylidene)platinum(II);
trans-diiodo(N-cyclopentylamine)(1-methyl-3-allylimidazol-2-ylidene)platinum(II);
trans-diiodo(N-cycloheptylamine)(1-methyl-3-allylimidazol-2-ylidene)platinum(II);
trans-diiodo(N-bicyclo[2.2.2]octylamine)(1-methyl-3-allylimidazol-2-ylidene)platinum(II);
trans-diiodo(N-endo(+/−)bicyclo[2.2.1]heptylamine)(1-methyl-3-allylimidazol-2-ylidene)platinum(II);
trans-diiodo(N-exo(+/−)bicyclo[3.2.1]octylamine)(1-methyl-3-allylimidazol-2-ylidene)platinum(II);
trans-diiodo(N-benzylamine)(1-methyl-3-allylimidazol-2-ylidene)platinum(II);
trans-diiodo(N-4-methoxybenzylamine)(1-methyl-3-allylimidazol-2-ylidene)platinum(II);
trans-diiodo(N-4-trifluoromethylbenzylamine)(1-methyl-3-allylimidazol-2-ylidene)platinum(II);
trans-diiodo(N-4-chlorobenzylamine)(1-methyl-3-allylimidazol-2-ylidene)platinum(II);
trans-diiodo(N-4-fluorobenzylamine)(1-methyl-3-allylimidazol-2-ylidene)platinum(II);
trans-diiodo(N-4-bromobenzylamine)(1-methyl-3-vinylimidazol-2-ylidene)platinum(II);
trans-diiodo(N-4-methylbenzylamine)(1-methyl-3-allylimidazol-2-ylidene)platinum(II);
trans-diiodo(N-3,4-dichlorobenzylamine)(1-methyl-3-allylimidazol-2-ylidene)platinum(II);
trans-diiodo(N-3,4-dimethoxybenzylamine)(1-methyl-3-allylimidazol-2-ylidene)platinum(II);
trans-diiodo(N-3,4-dimethylbenzylamine)(1-methyl-3-allylimidazol-2-ylidene)platinum(II);
trans-diiodo(N-cyclopropylamine)(1-methyl-3-tert-butylimidazol-2-ylidene)platinum(II);
trans-diiodo(N-cyclobutylamine)(1-methyl-3-tert-butylimidazol-2-ylidene)platinum(II);
trans-diiodo(N-cyclopentylamine)(1-methyl-3-tert-butylimidazol-2-ylidene)platinum(II);
trans-diiodo(N-cycloheptylamine)(1-methyl-3-tert-butylimidazol-2-ylidene)platinum(II);
trans-diiodo(N-bicyclo[2.2.2]octylamine)(1-methyl-3-tert-butylimidazol-2-ylidene)platinum(II);
trans-diiodo(N-endo(+/−)bicyclo[2.2.1]heptylamine)(1-methyl-3-tert-butylimidazol-2-ylidene)platinum(II);
trans-diiodo(N-exo(+/−)bicyclo[3.2.1]octylamine)(1-methyl-3-tert-butylimidazol-2-ylidene)platinum(II);
trans-diiodo(N-benzylamine)(1-methyl-3-tert-butylimidazol-2-ylidene)platinum(II);
trans-diiodo(N-4-methoxybenzylamine)(1-methyl-3-tert-butylimidazol-2-ylidene)platinum(II);
trans-diiodo(N-4-trifluoromethylbenzylamine)(1-methyl-3-tert-butylimidazol-2-ylidene)platinum(II);
trans-diiodo(N-4-chlorobenzylamine)(1-methyl-3-tert-butylimidazol-2-ylidene)platinum(II);
trans-diiodo(N-4-fluorobenzylamine)(1-methyl-3-tert-butylimidazol-2-ylidene)platinum(II);
trans-diiodo(N-4-bromobenzylamine)(1-methyl-3-tert-butylimidazol-2-ylidene)platinum(II);
trans-diiodo(N-4-methylbenzylamine)(1-methyl-3-tert-butylimidazol-2-ylidene)platinum(II);
trans-diiodo(N-3,4-dichlorobenzylamine)(1-methyl-3-tert-butylimidazol-2-ylidene)platinum(II);
trans-diiodo(N-3,4-dimethoxybenzylamine)(1-methyl-3-tert-butylimidazol-2-ylidene)platinum(II);
trans-diiodo(N-3,4-dimethylbenzylamine)(1-methyl-3-tert-butylimidazol-2-ylidene)platinum(II);

trans-diiodo(N-cyclopropylamine)(1-methyl-3-cyclohexylimidazol-2-ylidene)platinum(II);
trans-diiodo(N-cyclobutylamine)(1-methyl-3-cyclohexylimidazol-2-ylidene)platinum(II);
trans-diiodo(N-cyclopentylamine)(1-methyl-3-cyclohexylimidazol-2-ylidene)platinum(II);
trans-diiodo(N-cycloheptylamine)(1-methyl-3-cyclohexylimidazol-2-ylidene)platinum(II);
trans-diiodo(N-bicyclo[2.2.2]octylamine)(1-methyl-3-cyclohexylimidazol-2-ylidene)platinum(II);
trans-diiodo(N-endo(+/−)bicyclo[2.2.1]heptylamine)(1-methyl-3-cyclohexylimidazol-2-ylidene)platinum(II);
trans-diiodo(N-exo(+/−)bicyclo[3.2.1]octylamine)(1-methyl-3-cyclohexylimidazol-2-ylidene)platinum(II);
trans-diiodo(N-benzylamine)(1-methyl-3-cyclohexylimidazol-2-ylidene)platinum(II);
trans-diiodo(N-4-methoxybenzylamine)(1-methyl-3-cyclohexylimidazol-2-ylidene)platinum(II);
trans-diiodo(N-4-trifluoromethylbenzylamine)(1-methyl-3-cyclohexylimidazol-2-ylidene)platinum(II);
trans-diiodo(N-4-chlorobenzylamine)(1-methyl-3-cyclohexylimidazol-2-ylidene)platinum(II);
trans-diiodo(N-4-fluorobenzylamine)(1-methyl-3-cyclohexylimidazol-2-ylidene)platinum(II);
trans-diiodo(N-4-bromobenzylamine)(1-methyl-3-cyclohexylimidazol-2-ylidene)platinum(II);
trans-diiodo(N-4-methylbenzylamine)(1-methyl-3-cyclohexylimidazol-2-ylidene)platinum(II);
trans-diiodo(N-3,4-dichlorobenzylamine)(1-methyl-3-cyclohexylimidazol-2-ylidene)platinum(II);
trans-diiodo(N-3,4-dimethoxybenzylamine)(1-methyl-3-cyclohexylimidazol-2-ylidene)platinum(II);
trans-diiodo(N-3,4-dimethylbenzylamine)(1-methyl-3-cyclohexylimidazol-2-ylidene)platinum(II);
trans-diiodo(N-cyclopropylamine)(1-methyl-3-cyclohexylmethylimidazol-2-ylidene)platinum(II);
trans-diiodo(N-cyclobutylamine)(1-methyl-3-cyclohexylmethylimidazol-2-ylidene)platinum(II);
trans-diiodo(N-cyclopentylamine)(1-methyl-3-cyclohexylmethylimidazol-2-ylidene)platinum(II);
trans-diiodo(N-cycloheptylamine)(1-methyl-3-cyclohexylmethylimidazol-2-ylidene)platinum(II);
trans-diiodo(N-bicyclo[2.2.2]octylamine)(1-methyl-3-cyclohexylmethylimidazol-2-ylidene)platinum(II);
trans-diiodo(N-endo(+/−)bicyclo[2.2.1]heptylamine)(1-methyl-3-cyclohexylmethylimidazol-2-ylidene)platinum(II);
trans-diiodo(N-exo(+/−)bicyclo[3.2.1]octylamine)(1-methyl-3-cyclohexylmethylimidazol-2-ylidene)platinum(II);
trans-diiodo(N-benzylamine)(1-methyl-3-cyclohexylmethylimidazol-2-ylidene)platinum(II);
trans-diiodo(N-4-methoxybenzylamine)(1-methyl-3-cyclohexylmethylimidazol-2-ylidene)platinum(II);
trans-diiodo(N-4-trifluoromethylbenzylamine)(1-methyl-3-cyclohexylmethylimidazol-2-ylidene)platinum(II);
trans-diiodo(N-4-chlorobenzylamine)(1-methyl-3-cyclohexylmethylimidazol-2-ylidene)platinum(II);
trans-diiodo(N-4-fluorobenzylamine)(1-methyl-3-cyclohexylmethylimidazol-2-ylidene)platinum(II);
trans-diiodo(N-4-bromobenzylamine)(1-methyl-3-cyclohexylmethylimidazol-2-ylidene)platinum(II);
trans-diiodo(N-4-methylbenzylamine)(1-methyl-3-cyclohexylmethylimidazol-2-ylidene)platinum(II);
trans-diiodo(N-3,4-dichlorobenzylamine)(1-methyl-3-cyclohexylmethylimidazol-2-ylidene)platinum(II);
trans-diiodo(N-3,4-dimethoxybenzylamine)(1-methyl-3-cyclohexylmethylimidazol-2-ylidene)platinum(II);
trans-diiodo(N-3,4-dimethylbenzylamine)(1-methyl-3-cyclohexylmethylimidazol-2-ylidene)platinum(II);
trans-diiodo(N-cyclopropylamine)(1-methyl-3-cyclopropylimidazol-2-ylidene)platinum(II);
trans-diiodo(N-cyclobutylamine)(1-methyl-3-cyclopropylimidazol-2-ylidene)platinum(II);
trans-diiodo(N-cyclopentylamine)(1-methyl-3-cyclopropylimidazol-2-ylidene)platinum(II);
trans-diiodo(N-cycloheptylamine)(1-methyl-3-cyclopropylimidazol-2-ylidene)platinum(II);
trans-diiodo(N-bicyclo[2.2.2]octylamine)(1-methyl-3-cyclopropylimidazol-2-ylidene)platinum(II);
trans-diiodo(N-endo(+/−)bicyclo[2.2.1]heptylamine)(1-methyl-3-cyclopropylimidazol-2-ylidene)platinum(II);
trans-diiodo(N-exo(+/−)bicyclo[3.2.1]octylamine)(1-methyl-3-cyclopropylimidazol-2-ylidene)platinum(II);
trans-diiodo(N-benzylamine)(1-methyl-3-cyclopropylimidazol-2-ylidene)platinum(II);
trans-diiodo(N-4-methoxybenzylamine)(1-methyl-3-cyclopropylimidazol-2-ylidene)platinum(II);
trans-diiodo(N-4-trifluoromethylbenzylamine)(1-methyl-3-cyclopropylimidazol-2-ylidene)platinum(II);
trans-diiodo(N-4-chlorobenzylamine)(1-methyl-3-cyclopropylimidazol-2-ylidene)platinum(II);
trans-diiodo(N-4-fluorobenzylamine)(1-methyl-3-cyclopropylimidazol-2-ylidene)platinum(II);
trans-diiodo(N-4-bromobenzylamine)(1-methyl-3-cyclopropylimidazol-2-ylidene)platinum(II);
trans-diiodo(N-4-methylbenzylamine)(1-methyl-3-cyclopropylimidazol-2-ylidene)platinum(II);
trans-diiodo(N-3,4-dichlorobenzylamine)(1-methyl-3-cyclopropylimidazol-2-ylidene)platinum(II);
trans-diiodo(N-3,4-dimethoxybenzylamine)(1-methyl-3-cyclopropylimidazol-2-ylidene)platinum(II);
trans-diiodo(N-3,4-dimethylbenzylamine)(1-methyl-3-cyclopropylimidazol-2-ylidene)platinum(II);
trans-diiodo(N-cyclopropylamine)(1-methyl-3-cyclopropylmethylimidazol-2-ylidene)platinum(II);
trans-diiodo(N-cyclobutylamine)(1-methyl-3-cyclopropylmethylimidazol-2-ylidene)platinum(II);
trans-diiodo(N-cyclopentylamine)(1-methyl-3-cyclopropylmethylimidazol-2-ylidene)platinum(II);
trans-diiodo(N-cycloheptylamine)(1-methyl-3-cyclopropylmethylimidazol-2-ylidene)platinum(II);
trans-diiodo(N-bicyclo[2.2.2]octylamine)(1-methyl-3-cyclopropylmethylimidazol-2-ylidene)platinum(II);
trans-diiodo(N-endo(+/−)bicyclo[2.2.1]heptylamine)(1-methyl-3-cyclopropylmethylimidazol-2-ylidene)platinum(II);
trans-diiodo(N-exo(+/−)bicyclo[3.2.1]octylamine)(1-methyl-3-cyclopropylmethylimidazol-2-ylidene)platinum(II);
trans-diiodo(N-benzylamine)(1-methyl-3-cyclopropylmethylimidazol-2-ylidene)platinum(II);
trans-diiodo(N-4-methoxybenzylamine)(1-methyl-3-cyclopropylmethylimidazol-2-ylidene)platinum(II);
trans-diiodo(N-4-trifluoromethylbenzylamine)(1-methyl-3-cyclopropylmethylimidazol-2-ylidene)platinum(II);
trans-diiodo(N-4-chlorobenzylamine)(1-methyl-3-cyclopropylmethylimidazol-2-ylidene)platinum(II);
trans-diiodo(N-4-fluorobenzylamine)(1-methyl-3-cyclopropylmethylimidazol-2-ylidene)platinum(II);
trans-diiodo(N-4-bromobenzylamine)(1-methyl-3-cyclopropylmethylimidazol-2-ylidene)platinum(II);

trans-diiodo(N-4-methylbenzylamine)(1-methyl-3-cyclopropylmethylimidazol-2-ylidene)platinum(II);
trans-diiodo(N-3,4-dichlorobenzylamine)(1-methyl-3-cyclopropylmethylimidazol-2-ylidene)platinum(II);
trans-diiodo(N-3,4-dimethoxybenzylamine)(1-methyl-3-cyclopropylmethylimidazol-2-ylidene)platinum(II);
trans-diiodo(N-3,4-dimethylbenzylamine)(1-methyl-3-cyclopropylmethylimidazol-2-ylidene)platinum(II);
trans-diiodo(N-cyclopropylamine)(1,3-dicyclohexylimidazol-2-ylidene)platinum(II);
trans-diiodo(N-cyclobutylamine)(1,3-dicyclohexylimidazol-2-ylidene)platinum(II);
trans-diiodo(N-cyclopentylamine)(1,3-dicyclohexylimidazol-2-ylidene)platinum(II);
trans-diiodo(N-cycloheptylamine)(1,3-dicyclohexylimidazol-2-ylidene)platinum(II);
trans-diiodo(N-bicyclo[2.2.2]octylamine)(1,3-dicyclohexylimidazol-2-ylidene)platinum(II);
trans-diiodo(N-endo(+/−)bicyclo[2.2.1]heptylamine)(1,3-dicyclohexylimidazol-2-ylidene)platinum(II);
trans-diiodo(N-exo(+/−)bicyclo[3.2.1]octylamine)(1,3-dicyclohexylimidazol-2-ylidene)platinum(II);
trans-diiodo(N-benzylamine)(1,3-dicyclohexylimidazol-2-ylidene)platinum(II);
trans-diiodo(N-4-methoxybenzylamine)(1,3-dicyclohexylimidazol-2-ylidene)platinum(II);
trans-diiodo(N-4-trifluoromethylbenzylamine)(1,3-dicyclohexylimidazol-2-ylidene)platinum(II);
trans-diiodo(N-4-chlorobenzylamine)(1,3-dicyclohexylimidazol-2-ylidene)platinum(II);
trans-diiodo(N-4-fluorobenzylamine)(1,3-dicyclohexylimidazol-2-ylidene)platinum(II);
trans-diiodo(N-4-bromobenzylamine)(1,3-dicyclohexylimidazol-2-ylidene)platinum(II);
trans-diiodo(N-4-methylbenzylamine)(1,3-dicyclohexylimidazol-2-ylidene)platinum(II);
trans-diiodo(N-3,4-dichlorobenzylamine)(1,3-dicyclohexylimidazol-2-ylidene)platinum(II);
trans-diiodo(N-3,4-dimethoxybenzylamine)(1,3-dicyclohexylimidazol-2-ylidene)platinum(II);
trans-diiodo(N-3,4-dimethylbenzylamine)(1,3-dicyclohexylimidazol-2-ylidene)platinum(II);
trans-diiodo(N-cyclopropylamine)(1,3-dicyclohexylmethylimidazol-2-ylidene)platinum(II);
trans-diiodo(N-cyclobutylamine)(1,3-dicyclohexylmethylimidazol-2-ylidene)platinum(II);
trans-diiodo(N-cyclopentylamine)(1,3-dicyclohexylmethylimidazol-2-ylidene)platinum(II);
trans-diiodo(N-cycloheptylamine)(1,3-dicyclohexylmethylimidazol-2-ylidene)platinum(II);
trans-diiodo(N-bicyclo[2.2.2]octylamine)(1,3-dicyclohexylmethylimidazol-2-ylidene)platinum(II);
trans-diiodo(N-endo(+/−)bicyclo[2.2.1]heptylamine)(1,3-dicyclohexylmethylimidazol-2-ylidene)platinum(II);
trans-diiodo(N-exo(+/−)bicyclo[3.2.1]octylamine)(1,3-dicyclohexylmethylimidazol-2-ylidene)platinum(II);
trans-diiodo(N-benzylamine)(1,3-dicyclohexylmethylimidazol-2-ylidene)platinum(II);
trans-diiodo(N-4-methoxybenzylamine)(1,3-dicyclohexylmethylimidazol-2-ylidene)platinum(II);
trans-diiodo(N-4-trifluoromethylbenzylamine)(1,3-dicyclohexylmethylimidazol-2-ylidene)platinum(II);
trans-diiodo(N-4-chlorobenzylamine)(1,3-dicyclohexylmethylimidazol-2-ylidene)platinum(II);
trans-diiodo(N-4-fluorobenzylamine)(1,3-dicyclohexylmethylimidazol-2-ylidene)platinum(II);
trans-diiodo(N-4-bromobenzylamine)(1,3-dicyclohexylmethylimidazol-2-ylidene)platinum(II);
trans-diiodo(N-4-methylbenzylamine)(1,3-dicyclohexylmethylimidazol-2-ylidene)platinum(II);
trans-diiodo(N-3,4-dichlorobenzylamine)(1,3-dicyclohexylmethylimidazol-2-ylidene)platinum(II);
trans-diiodo(N-3,4-dimethoxybenzylamine)(1,3-dicyclohexylmethylimidazol-2-ylidene)platinum(II);
trans-diiodo(N-3,4-dimethylbenzylamine)(1,3-dicyclohexylmethylimidazol-2-ylidene)platinum(II);
trans-diiodo(N-cyclopropylamine)(1,3-dicyclopropylmethylimidazol-2-ylidene)platinum(II);
trans-diiodo(N-cyclobutylamine)(1,3-dicyclopropylmethylimidazol-2-ylidene)platinum(II);
trans-diiodo(N-cyclopentylamine)(1,3-dicyclopropylmethylimidazol-2-ylidene)platinum(II);
trans-diiodo(N-cycloheptylamine)(1,3-dicyclopropylmethylimidazol-2-ylidene)platinum(II);
trans-diiodo(N-bicyclo[2.2.2]octylamine)(1,3-dicyclopropylmethylimidazol-2-ylidene)platinum(II);
trans-diiodo(N-endo(+/−)bicyclo[2.2.1]heptylamine)(1,3-dicyclopropylmethylimidazol-2-ylidene)platinum(II);
trans-diiodo(N-exo(+/−)bicyclo[3.2.1]octylamine)(1,3-dicyclopropylmethylimidazol-2-ylidene)platinum(II);
trans-diiodo(N-benzylamine)(1,3-dicyclopropylmethylimidazol-2-ylidene)platinum(II);
trans-diiodo(N-4-methoxybenzylamine)(1,3-dicyclopropylimidazol-2-ylidene)platinum(II);
trans-diiodo(N-4-trifluoromethylbenzylamine)(1,3-dicyclopropylmethylimidazol-2-ylidene)platinum(II);
trans-diiodo(N-4-chlorobenzylamine)(1,3-dicyclopropylmethylimidazol-2-ylidene)platinum(II);
trans-diiodo(N-4-fluorobenzylamine)(1,3-dicyclopropylmethylimidazol-2-ylidene)platinum(II);
trans-diiodo(N-4-bromobenzylamine)(1,3-dicyclopropylmethylimidazol-2-ylidene)platinum(II);
trans-diiodo(N-4-methylbenzylamine)(1,3-dicyclohexylmethylimidazol-2-ylidene)platinum(II);
trans-diiodo(N-3,4-dichlorobenzylamine)(1,3-dicyclohexylmethylimidazol-2-ylidene)platinum(II);
trans-diiodo(N-3,4-dimethoxybenzylamine)(1,3-dicyclohexylmethylimidazol-2-ylidene)platinum(II);
trans-diiodo(N-3,4-dimethylbenzylamine)(1,3-dicyclohexylmethylimidazol-2-ylidene)platinum(II);
trans-diiodo(N-cyclopropylamine)(1-methyl-3-phenyl-1,2,4-triazol-5-ylidene)platinum(II);
trans-diiodo(N-cyclobutylamine)(1-methyl-3-phenyl-1,2,4-triazol-5-ylidene)platinum(II);
trans-diiodo(N-cyclopentylamine)(1-methyl-3-phenyl-1,2,4-triazol-5-ylidene)platinum(II);
trans-diiodo(N-cycloheptylamine)(1-methyl-3-phenyl-1,2,4-triazol-5-ylidene)platinum(II);
trans-diiodo(N-bicyclo[2.2.2]octylamine)(1-methyl-3-phenyl-1,2,4-triazol-5-ylidene)platinum(II);
trans-diiodo(N-endo(+/−)bicyclo[2.2.1]heptylamine)(1-methyl-3-phenyl-1,2,4-triazol-5-ylidene)platinum(II);
trans-diiodo(N-exo(+/−)bicyclo[3.2.1]octylamine)(1-methyl-3-phenyl-1,2,4-triazol-5-ylidene)platinum(II);
trans-diiodo(N-benzylamine)(1-methyl-3-phenyl-1,2,4-triazol-5-ylidene)platinum(II);
trans-diiodo(N-4-methoxybenzylamine)(1-methyl-3-phenyl-1,2,4-triazol-5-ylidene)platinum(II);
trans-diiodo(N-4-trifluoromethylbenzylamine)(1-methyl-3-phenyl-1,2,4-triazol-5-ylidene)platinum(II);
trans-diiodo(N-4-chlorobenzylamine)(1-methyl-3-phenyl-1,2,4-triazol-5-ylidene)platinum(II);

trans-diiodo(N-4-fluorobenzylamine)(1-methyl-3-phenyl-1,2,4-triazol-5-ylidene)platinum(II);
trans-diiodo(N-4-bromobenzylamine)(1-methyl-3-phenyl-1,2,4-triazol-5-ylidene)platinum(II);
trans-diiodo(N-4-methylbenzylamine)(1-methyl-3-phenyl-1,2,4-triazol-5-ylidene)platinum(II);
trans-diiodo(N-3,4-dichlorobenzylamine)(1-methyl-3-phenyl-1,2,4-triazol-5-ylidene)platinum(II);
trans-diiodo(N-3,4-dimethoxybenzylamine)(1-methyl-3-phenyl-1,2,4-triazol-5-ylidene)platinum(II);
trans-diiodo(N-3,4-dimethylbenzylamine)(1-methyl-3-phenyl-1,2,4-triazol-5-ylidene)platinum(II);
trans-diiodo(N-cyclopropylamine)(1-methyl-3-cyclohexyl-1,2,4-triazol-5-ylidene)platinum(II);
trans-diiodo(N-cyclobutylamine)(1-methyl-3-cyclohexyl-1,2,4-triazol-5-ylidene)platinum(II);
trans-diiodo(N-cyclopentylamine)(1-methyl-3-cyclohexyl-1,2,4-triazol-5-ylidene)platinum(II);
trans-diiodo(N-cycloheptylamine(1-methyl-3-cyclohexyl-1,2,4-triazol-5-ylidene)platinum(II);
trans-diiodo(N-bicyclo[2.2.2]octylamine)(1-methyl-3-cyclohexyl-1,2,4-triazol-5-ylidene)platinum(II);
trans-diiodo(N-endo(+/−)bicyclo[2.2.1]heptylamine)(1-methyl-3-cyclohexyl-1,2,4-triazol-5-ylidene)platinum(II);
trans-diiodo(N-exo(+/−)bicyclo[3.2.1]octylamine)(1-methyl-3-cyclohexyl-1,2,4-triazol-5-ylidene)platinum(II);
trans-diiodo(N-benzylamine)(1-methyl-3-cyclohexyl-1,2,4-triazol-5-ylidene)platinum(II);
trans-diiodo(N-4-methoxybenzylamine)(1-methyl-3-cyclohexyl-1,2,4-triazol-5-ylidene)platinum(II);
trans-diiodo(N-4-trifluoromethylbenzylamine)(1-methyl-3-cyclohexyl-1,2,4-triazol-5-ylidene)platinum(II);
trans-diiodo(N-4-chlorobenzylamine)(1-methyl-3-cyclohexyl-1,2,4-triazol-5-ylidene)platinum(II);
trans-diiodo(N-4-fluorobenzylamine)(1-methyl-3-cyclohexyl-1,2,4-triazol-5-ylidene)platinum(II);
trans-diiodo(N-4-bromobenzylamine)(1-methyl-3-cyclohexyl-1,2,4-triazol-5-ylidene)platinum(II);
trans-diiodo(N-4-methylbenzylamine)(1-methyl-3-cyclohexyl-1,2,4-triazol-5-ylidene)platinum(II);
trans-diiodo(N-3,4-dichlorobenzylamine)(1-methyl-3-cyclohexyl-1,2,4-triazol-5-ylidene)platinum(II);
trans-diiodo(N-3,4-dimethoxybenzylamine)(1-methyl-3-cyclohexyl-1,2,4-triazol-5-ylidene)platinum(II);
trans-diiodo(N-cyclopropylamine)(1-methyl-3-benzyl-1,2,4-triazol-5-ylidene)platinum(II);
trans-diiodo(N-cyclobutylamine)(1-methyl-3-benzyl-1,2,4-triazol-5-ylidene)platinum(II);
trans-diiodo(N-cyclopentylamine)(1-methyl-3-benzyl-1,2,4-triazol-5-ylidene)platinum(II);
trans-diiodo(N-cycloheptylamine)(1-methyl-3-benzyl-1,2,4-triazol-5-ylidene)platinum(II);
trans-diiodo(N-bicyclo[2.2.2]octylamine)(1-methyl-3-benzyl-1,2,4-triazol-5-ylidene)platinum(II);
trans-diiodo(N-endo(+/−)bicyclo[2.2.1]heptylamine)(1-methyl-3-benzyl-1,2,4-triazol-5-ylidene)platinum(II);
trans-diiodo(N-exo(+/−)bicyclo[3.2.1]octylamine)(1-methyl-3-benzyl-1,2,4-triazol-5-ylidene)platinum(II);
trans-diiodo(N-benzylamine)(1-methyl-3-benzyl-1,2,4-triazol-5-ylidene)platinum(II);
trans-diiodo(N-4-methoxybenzylamine)(1-methyl-3-benzyl-1,2,4-triazol-5-ylidene)platinum(II);
trans-diiodo(N-4-trifluoromethylbenzylamine)(1-methyl-3-benzyl-1,2,4-triazol-5-ylidene)platinum(II);
trans-diiodo(N-4-chlorobenzylamine)(1-methyl-3-benzyl-1,2,4-triazol-5-ylidene)platinum(II);
trans-diiodo(N-4-fluorobenzylamine)(1-methyl-3-benzyl-1,2,4-triazol-5-ylidene)platinum(II);
trans-diiodo(N-4-bromobenzylamine)(1-methyl-3-benzyl-1,2,4-triazol-5-ylidene)platinum(II);
trans-diiodo(N-4-methylbenzylamine)(1-methyl-3-benzyl-1,2,4-triazol-5-ylidene)platinum(II);
trans-diiodo(N-3,4-dichlorobenzylamine)(1-methyl-3-benzyl-1,2,4-triazol-5-ylidene)platinum(II);
trans-diiodo(N-3,4-dimethoxybenzylamine)(1-methyl-3-benzyl-1,2,4-triazol-5-ylidene)platinum(II);
trans-diiodo(N-cyclopropylamine)[1-methyl-3-(4-trifluoromethylbenzyl)-1,2,4-triazol-5-ylidene]platinum(II);
trans-diiodo(N-cyclobutylamine)[1-methyl-3-(4-trifluoromethylbenzyl)-1,2,4-triazol-5-ylidene]platinum(II);
trans-diiodo(N-cyclopentylamine)[1-methyl-3-(4-trifluoromethylbenzyl)-1,2,4-triazol-5-ylidene]platinum(II);
trans-diiodo(N-cycloheptylamine)[1-methyl-3-(4-trifluoromethylbenzyl)-1,2,4-triazol-5-ylidene]platinum(II);
trans-diiodo(N-bicyclo[2.2.2]octylamine)[1-methyl-3-(4-trifluoromethylbenzyl)-1,2,4-triazol-5-ylidene]platinum(II);
trans-diiodo(N-endo(+/−)bicyclo[2.2.1]heptylamine)[1-methyl-3-(4-trifluoromethylbenzyl)-1,2,4-triazol-5-ylidene]platinum(II);
trans-diiodo(N-exo(+/−)bicyclo[3.2.1]octylamine)[1-methyl-3-(4-trifluoromethylbenzyl)-1,2,4-triazol-5-ylidene]platinum(II);
trans-diiodo(N-benzylamine)[1-methyl-3-(4-trifluoromethylbenzyl)-1,2,4-triazol-5-ylidene]platinum(II);
trans-diiodo(N-4-methoxybenzylamine)[1-methyl-3-(4-trifluoromethylbenzyl)-1,2,4-triazol-5-ylidene]platinum(II);
trans-diiodo(N-4-trifluoromethylbenzylamine)[1-methyl-3-(4-trifluoromethylbenzyl)-1,2,4-triazol-5-ylidene]platinum(II);
trans-diiodo(N-4-chlorobenzylamine)[1-methyl-3-(4-trifluoromethylbenzyl)-1,2,4-triazol-5-ylidene]platinum(II);
trans-diiodo(N-4-fluorobenzylamine)[1-methyl-3-(4-trifluoromethylbenzyl)-1,2,4-triazol-5-ylidene]platinum(II);
trans-diiodo(N-4-bromobenzylamine)[1-methyl-3-(4-trifluoromethylbenzyl)-1,2,4-triazol-5-ylidene]platinum(II);
trans-diiodo(N-4-methylbenzylamine)[1-methyl-3-(4-trifluoromethylbenzyl)-1,2,4-triazol-5-ylidene]platinum(II);
trans-diiodo(N-3,4-dichlorobenzylamine)[1-methyl-3-(4-trifluoromethylbenzyl)-1,2,4-triazol-5-ylidene]platinum(II);
trans-diiodo(N-3,4-dimethoxybenzylamine)[1-methyl-3-(4-trifluoromethylbenzyl)-1,2,4-triazol-5-ylidene]platinum(II);
trans-diiodo(N-cyclopropylamine)(1,3-dibenzyl-1,2,4-triazol-5-ylidene)platinum(II);
trans-diiodo(N-cyclobutylamine)(1,3-dibenzyl-1,2,4-triazol-5-ylidene)platinum(II);
trans-diiodo(N-cyclopentylamine)(1,3-dibenzyl-1,2,4-triazol-5-ylidene)platinum(II);
trans-diiodo(N-cycloheptylamine)(1,3-dibenzyl-1,2,4-triazol-5-ylidene)platinum(II);
trans-diiodo(N-bicyclo[2.2.2]octylamine)(1,3-dibenzyl-1,2,4-triazol-5-ylidene)platinum(II);
trans-diiodo(N-endo(+/−)bicyclo[2.2.1]heptylamine)(1,3-dibenzyl-1,2,4-triazol-5-ylidene)platinum(II);
trans-diiodo(N-exo(+/−)bicyclo[3.2.1]octylamine)(1,3-dibenzyl-1,2,4-triazol-5-ylidene)platinum(II);

trans-diiodo(N-benzylamine)(1,3-dibenzyl-1,2,4-triazol-5-ylidene)platinum(II);
trans-diiodo(N-4-methoxybenzylamine)(1,3-dibenzyl-1,2,4-triazol-5-ylidene)platinum(II);
trans-diiodo(N-4-trifluoromethylbenzylamine)(1,3-dibenzyl-1,2,4-triazol-5-ylidene)platinum(II);
trans-diiodo(N-4-chlorobenzylamine)(1,3-dibenzyl-1,2,4-triazol-5-ylidene)platinum(II);
trans-diiodo(N-4-fluorobenzylamine)(1,3-dibenzyl-1,2,4-triazol-5-ylidene)platinum(II);
trans-diiodo(N-4-bromobenzylamine)(1,3-dibenzyl-1,2,4-triazol-5-ylidene)platinum(II);
trans-diiodo(N-4-methylbenzylamine)(1,3-dibenzyl-1,2,4-triazol-5-ylidene)platinum(II);
trans-diiodo(N-3,4-dichlorobenzylamine)(1,3-dibenzyl-1,2,4-triazol-5-ylidene)platinum(II);
trans-diiodo(N-3,4-dimethoxybenzylamine)(1,3-dibenzyl-1,2,4-triazol-5-ylidene)platinum(II);
trans-diiodo(N-cyclopropylamine)[1,3-dimethyl-4-phenylimidazol-2-ylidene]-platinum(II);
trans-diiodo(N-cyclobutylamine)[1,3-dimethyl-4-phenylimidazol-2-ylidene]platinum(II);
trans-diiodo(N-cyclopentylamine)[1,3-dimethyl-4-phenylimidazol-2-ylidene]-platinum(II);
trans-diiodo(N-cycloheptylamine)[1,3-dimethyl-4-phenylimidazol-2-ylidene]-platinum(II);
trans-diiodo(N-bicyclo[2.2.2]octylamine)[1,3-dimethyl-4-phenylimidazol-2-ylidene]-platinum(II);
trans-diiodo(N-endo(+/−)bicyclo[2.2.1]heptylamine)[1,3-dimethyl-4-phenylimidazol-2-ylidene]platinum(II);
trans-diiodo(N-exo(+/−)bicyclo[3.2.1]octylamine)[1,3-dimethyl-4-phenylimidazol-2-ylidene]platinum(II);
trans-diiodo(N-benzylamine)[1,3-dimethyl-4-phenylimidazol-2-ylidene]platinum(II);
trans-diiodo(N-4-methoxybenzylamine)[1,3-dimethyl-4-phenylimidazol-2-ylidene]-platinum(II);
trans-diiodo(N-4-trifluoromethylbenzylamine)[1,3-dimethyl-4-phenylimidazol-2-ylidene]platinum(II);
trans-diiodo(N-4-chlorobenzylamine)[1,3-dimethyl-4-phenylimidazol-2-ylidene]-platinum(II);
trans-diiodo(N-4-fluorobenzylamine)[1,3-dimethyl-4-phenylimidazol-2-ylidene]-platinum(II);
trans-diiodo(N-4-bromobenzylamine)[1,3-dimethyl-4-phenylimidazol-2-ylidene]-platinum(II);
trans-diiodo(N-4-methylbenzylamine)[1,3-dimethyl-4-phenylimidazol-2-ylidene]-platinum(II);
trans-diiodo(N-3,4-dichlorobenzylamine)[1,3-dimethyl-4-phenylimidazol-2-ylidene]-platinum(II);
trans-diiodo(N-3,4-dimethoxybenzylamine)[1,3-dimethyl-4-phenylimidazol-2-ylidene]platinum(II);
trans-diiodo(N-3,4-dimethylbenzylamine)[1,3-dimethyl-4-phenylimidazol-2-ylidene]-platinum(II);
trans-diiodo(N-cyclopropylamine)[3-benzyl-1-methyl-4-phenylimidazol-2-ylidene]-platinum(II);
trans-diiodo(N-cyclobutylamine)[3-benzyl-1-methyl-4-phenylimidazol-2-ylidene]-platinum(II);
trans-diiodo(N-cyclopentylamine)[3-benzyl-1-methyl-4-phenylimidazol-2-ylidene]-platinum(II);
trans-diiodo(N-cycloheptylamine)[3-benzyl-1-methyl-4-phenylimidazol-2-ylidene]-platinum(II);
trans-diiodo(N-bicyclo[2.2.2]octylamine)[3-benzyl-1-methyl-4-phenylimidazol-2-ylidene]platinum(II);
trans-diiodo(N-endo(+/−)bicyclo[2.2.1]heptylamine)[3-benzyl-1-methyl-4-phenylimidazol-2-ylidene]platinum(II);
trans-diiodo(N-exo(+/−)bicyclo[3.2.1]octylamine)[3-benzyl-1-methyl-4-phenylimidazol-2-ylidene]platinum(II);
trans-diiodo(N-benzylamine)[3-benzyl-1-methyl-4-phenylimidazol-2-ylidene]-platinum(II);
trans-diiodo(N-4-methoxybenzylamine)[3-benzyl-1-methyl-4-phenylimidazol-2-ylidene]platinum(II);
trans-diiodo(N-4-trifluoromethylbenzylamine)[3-benzyl-1-methyl-4-phenylimidazol-2-ylidene]platinum(II);
trans-diiodo(N-4-chlorobenzylamine)[3-benzyl-1-methyl-4-phenylimidazol-2-ylidene]platinum(II);
trans-diiodo(N-4-fluorobenzylamine)[3-benzyl-1-methyl-4-phenylimidazol-2-ylidene]platinum(II);
trans-diiodo(N-4-bromobenzylamine)[3-benzyl-1-methyl-4-phenylimidazol-2-ylidene]platinum(II);
trans-diiodo(N-4-methylbenzylamine)[3-benzyl-1-methyl-4-phenylimidazol-2-ylidene]platinum(II);
trans-diiodo(N-3,4-dichlorobenzylamine)[3-benzyl-1-methyl-4-phenylimidazol-2-ylidene]platinum(II);
trans-diiodo(N-3,4-dimethoxybenzylamine)[3-benzyl-1-methyl-4-phenylimidazol-2-ylidene]platinum(II);
trans-diiodo(N-3,4-dimethylbenzylamine)[3-benzyl-1-methyl-4-phenylimidazol-2-ylidene]platinum(II);
trans-diiodo(N-cyclopropylamine)[1,3-dimethyl-4,5-diphenylimidazol-2-ylidene]-platinum(II);
trans-diiodo(N-cyclobutylamine)[1,3-dimethyl-4,5-diphenylimidazol-2-ylidene]-platinum(II);
trans-diiodo(N-cyclopentylamine)[1,3-dimethyl-4,5-diphenylimidazol-2-ylidene]-platinum(II);
trans-diiodo(N-cycloheptylamine)[1,3-dimethyl-4,5-diphenylimidazol-2-ylidene]-platinum(II);
trans-diiodo(N-bicyclo[2.2.2]octylamine)[1,3-dimethyl-4,5-diphenylimidazol-2-ylidene]-platinum(II);
trans-diiodo(N-endo(+/−)bicyclo[2.2.1]heptylamine)[1,3-dimethyl-4,5-diphenylimidazol-2-ylidene]platinum(II);
trans-diiodo(N-exo(+/−)bicyclo[3.2.1]octylamine)[1,3-dimethyl-4,5-diphenylimidazol-2-ylidene]platinum(II);
trans-diiodo(N-benzylamine)[1,3-dimethyl-4,5-diphenylimidazol-2-ylidene]platinum(II);
trans-diiodo(N-4-methoxybenzylamine)[1,3-dimethyl-4,5-diphenylimidazol-2-ylidene]platinum(II);
trans-diiodo(N-4-trifluoromethylbenzylamine)[1,3-dimethyl-4,5-diphenylimidazol-2-ylidene]platinum(II);
trans-diiodo(N-4-chlorobenzylamine)[1,3-dimethyl-4,5-diphenylimidazol-2-ylidene]-platinum(II);
trans-diiodo(N-4-fluorobenzylamine)[1,3-dimethyl-4,5-diphenylimidazol-2-ylidene]-platinum(II);
trans-diiodo(N-4-bromobenzylamine)[1,3-dimethyl-4,5-diphenylimidazol-2-ylidene]-platinum(II);
trans-diiodo(N-4-methylbenzylamine)[1,3-dimethyl-4,5-diphenylimidazol-2-ylidene]-platinum(II);
trans-diiodo(N-3,4-dichlorobenzylamine)[1,3-dimethyl-4,5-diphenylimidazol-2-ylidene]platinum(II);
trans-diiodo(N-3,4-dimethoxybenzylamine)[1,3-dimethyl-4,5-diphenylimidazol-2-ylidene]platinum(II); or
trans-diiodo(N-3,4-dimethylbenzylamine)[1,3-dimethyl-4,5-diphenylimidazol-2-ylidene]platinum(II);

or a pharmaceutically acceptable salt thereof.

\* \* \* \* \*